(12) United States Patent
Tsai et al.

(10) Patent No.: US 10,497,747 B2
(45) Date of Patent: Dec. 3, 2019

(54) INTEGRATED PIEZOELECTRIC MICROELECTROMECHANICAL ULTRASOUND TRANSDUCER (PMUT) ON INTEGRATED CIRCUIT (IC) FOR FINGERPRINT SENSING

(71) Applicant: INVENSENSE, INC., San Jose, CA (US)

(72) Inventors: Julius Ming-Lin Tsai, San Jose, CA (US); Michael Daneman, Campbell, CA (US)

(73) Assignee: INVENSENSE, INC., San Jose, CA (US)

( * ) Notice: Subject to any disclaimer, the term of this patent is extended or adjusted under 35 U.S.C. 154(b) by 0 days.

(21) Appl. No.: 14/829,404

(22) Filed: Aug. 18, 2015

(65) Prior Publication Data

US 2015/0357375 A1 Dec. 10, 2015

Related U.S. Application Data

(63) Continuation-in-part of application No. 14/480,051, filed on Sep. 8, 2014, now Pat. No. 9,511,994, and a
(Continued)

(51) Int. Cl.
*H01L 41/113* (2006.01)
*H01L 41/31* (2013.01)
(Continued)

(52) U.S. Cl.
CPC .......... *H01L 27/20* (2013.01); *B81C 1/00246* (2013.01); *G01N 29/2437* (2013.01); *G06K 9/00006* (2013.01); *H01L 41/1132* (2013.01); *H01L 41/31* (2013.01); *G01N 2291/023* (2013.01)

(58) Field of Classification Search
USPC ................................................. 257/254, 253
See application file for complete search history.

(56) References Cited

U.S. PATENT DOCUMENTS 3,748,502 A 7/1973 Bernstein
4,556,871 A 2/1985 Yoshikawa et al.
(Continued)

FOREIGN PATENT DOCUMENTS

CN 1848472 A 10/2006
CN 1975956 A 6/2007
(Continued)

OTHER PUBLICATIONS

Khuri-Yakub, et al. "Next-gen ultrasound," IEEE Spectrum, vol. 46, No. 5, pp. 44-54, May 2009.
(Continued)

*Primary Examiner* — Timor Karimy
(74) *Attorney, Agent, or Firm* — Amin, Turocy & Watson, LLP

(57) ABSTRACT

Microelectromechanical (MEMS) devices and associated methods are disclosed. Piezoelectric MEMS transducers (PMUTs) suitable for integration with complementary metal oxide semiconductor (CMOS) integrated circuit (IC), as well as PMUT arrays having high fill factor for fingerprint sensing, are described.

14 Claims, 53 Drawing Sheets

Related U.S. Application Data continuation-in-part of application No. 14/453,326, filed on Aug. 6, 2014, now Pat. No. 9,618,405, said application No. 14/480,051 is a continuation-in-part of application No. 13/687,304, filed on Nov. 28, 2012, now Pat. No. 9,114,977.

(60) Provisional application No. 62/153,480, filed on Apr. 27, 2015, provisional application No. 61/880,110, filed on Sep. 19, 2013.

(51) Int. Cl.
    *G06K 9/00*     (2006.01)
    *H01L 27/20*     (2006.01)
    *B81C 1/00*     (2006.01)
    *G01N 29/24*     (2006.01)

(56) References Cited

U.S. PATENT DOCUMENTS

| | | |
|---|---|---|
| 5,386,479 A | 1/1995 | Hersh |
| 5,963,679 A | 10/1999 | Setlak |
| 7,013,031 B2 | 3/2006 | Kim et al. |
| 7,053,529 B2 | 5/2006 | Knowles |
| 7,067,962 B2 | 6/2006 | Scott |
| 7,109,642 B2 | 9/2006 | Scott |
| 7,400,750 B2 | 7/2008 | Nam |
| 7,459,836 B2 | 12/2008 | Scott |
| 7,489,066 B2 | 2/2009 | Scott et al. |
| 7,739,912 B2 | 6/2010 | Schneider et al. |
| 8,139,827 B2 | 3/2012 | Schneider et al. |
| 8,335,356 B2 | 12/2012 | Schmitt |
| 8,433,110 B2 | 4/2013 | Kropp et al. |
| 8,508,103 B2 | 8/2013 | Schmitt et al. |
| 8,515,135 B2 | 8/2013 | Clarke et al. |
| 8,666,126 B2 | 3/2014 | Lee et al. |
| 8,703,040 B2 | 4/2014 | Liufu et al. |
| 8,723,399 B2 | 5/2014 | Sammoura et al. |
| 8,805,031 B2 | 8/2014 | Schmitt |
| 8,913,039 B2 | 12/2014 | Nikolovski et al. |
| 9,007,348 B2 | 4/2015 | Nikolovski |
| 9,056,082 B2 | 6/2015 | Liautaud et al. |
| 9,114,977 B2 * | 8/2015 | Daneman ............. B81C 3/001 |
| 9,182,853 B2 | 11/2015 | Wennemer et al. |
| 9,342,187 B2 | 5/2016 | Jakobsen et al. |
| 9,909,225 B2 | 3/2018 | Lee et al. |
| 2001/0022488 A1 | 9/2001 | Kawauchi et al. |
| 2004/0094815 A1 | 5/2004 | Park et al. |
| 2004/0251781 A1 | 12/2004 | Bouche et al. |
| 2005/0146401 A1 | 7/2005 | Tilmans et al. |
| 2006/0012583 A1 | 1/2006 | Knowles et al. |
| 2007/0230754 A1 | 3/2007 | Jain et al. |
| 2007/0096300 A1 | 5/2007 | Wang et al. |
| 2007/0096605 A1 | 5/2007 | Fujii et al. |
| 2008/0198145 A1 | 8/2008 | Knowles et al. |
| 2008/0296708 A1 * | 12/2008 | Wodnicki ............. B06B 1/0292 257/414 |
| 2009/0274343 A1 | 11/2009 | Clarke |
| 2010/0251824 A1 | 6/2010 | Schneider et al. |
| 2010/0239751 A1 | 9/2010 | Regniere |
| 2010/0256498 A1 | 10/2010 | Tanaka |
| 2011/0049652 A1 | 3/2011 | Wu et al. |
| 2011/0210554 A1 | 9/2011 | Boysel |
| 2011/0285244 A1 | 11/2011 | Lewis et al. |
| 2012/0016604 A1 | 1/2012 | Irving et al. |
| 2012/0049299 A1 | 3/2012 | Chou |
| 2012/0074554 A1 | 3/2012 | Cheng et al. |
| 2012/0092026 A1 | 4/2012 | Liautaud et al. |
| 2012/0147698 A1 | 6/2012 | Wong et al. |
| 2012/0167823 A1 | 7/2012 | Gardner et al. |
| 2012/0279865 A1 | 11/2012 | Regniere et al. |
| 2012/0288641 A1 | 11/2012 | Diatezua et al. |
| 2012/0319220 A1 | 12/2012 | Noda et al. |
| 2013/0032906 A1 * | 2/2013 | Ogawa ............. B81C 1/00658 257/420 |
| 2013/0099355 A1 | 4/2013 | Liu et al. |
| 2013/0127592 A1 | 5/2013 | Fyke et al. |
| 2013/0133428 A1 | 5/2013 | Lee et al. |
| 2013/0201134 A1 | 8/2013 | Schneider et al. |
| 2013/0210175 A1 | 8/2013 | Hoisington et al. |
| 2014/0145244 A1 | 5/2014 | Daneman et al. |
| 2014/0176332 A1 | 6/2014 | Alameh et al. |
| 2014/0219063 A1 | 8/2014 | Hajati et al. |
| 2014/0219521 A1 | 8/2014 | Schmitt et al. |
| 2014/0355387 A1 | 12/2014 | Kitchens, II et al. |
| 2015/0035375 A1 | 2/2015 | Mayer et al. |
| 2015/0036065 A1 | 2/2015 | Yousefpor et al. |
| 2015/0076963 A1 | 3/2015 | Sipp |
| 2015/0169136 A1 | 6/2015 | Ganti et al. |
| 2015/0189136 A1 | 7/2015 | Chung et al. |
| 2015/0220767 A1 | 8/2015 | Yoon et al. |
| 2015/0261261 A1 | 9/2015 | Bhagavatula et al. |
| 2015/0286312 A1 | 10/2015 | Kang et al. |
| 2015/0298965 A1 * | 10/2015 | Tsai ............. B81C 1/00182 257/415 |
| 2016/0031702 A1 * | 2/2016 | Daneman ............. B81C 3/001 257/415 |
| 2016/0117541 A1 * | 4/2016 | Lu ............. G06K 9/0002 382/124 |

FOREIGN PATENT DOCUMENTS

| | | |
|---|---|---|
| CN | 101375236 | 2/2009 |
| CN | 101578573 | 11/2009 |
| CN | 102590555 A | 7/2012 |
| CN | 103026520 A | 4/2013 |
| EP | 1533743 A1 | 5/2005 |
| KR | 20090010357 A | 1/2009 |
| WO | 2009137106 A2 | 11/2009 |
| WO | 2015009635 A1 | 1/2015 |
| WO | 2015112453 A1 | 7/2015 |
| WO | 2015120132 A1 | 8/2015 |
| WO | 2015131083 A1 | 9/2015 |

OTHER PUBLICATIONS

Lamberti, et al. "A high frequency cMUT probe for ultrasound imaging of fingerprints," Sensors and Actuators A: Physical 172 (2), pp. 561-569. 2011.

Iula, et al. "Capacitive Microfabricated Ultrasonic Transducers for Biometric Applications"; Microelectronic Engineering, vol. 88, Issue 8, 2011, pp. 2278-2280.

Tang, et al. "Pulse-Echo Ultrasonic Fingerprint Sensor on a Chip," University of California, Berkeley, CA, USA, 2013.

Lu, et al. "High frequency piezoelectric micromachined ultrasonic transducer array for intravascular ultrasound imaging." Micro Electro Mechanical Systems (MEMS), 2014 IEEE 27th International Conference on. IEEE, 2014.

Olsson, III, et al. "Post-CMOS-Compatible Aluminum Nitride Resonant MEMS Accelerometers." Journal of Microelectromechanical Systems, vol. 18, No. 3, Jun. 2009.

Wojciechowski, et al. "Single-chip precision oscillators based on multi-frequency, high-Q aluminum nitride MEMS resonators." Solid-State Sensors, Actuators and Microsystems Conference, 2009. TRANSDUCERS 2009. International. IEEE, 2009.

Office Action dated Jan. 30, 2014 for U.S. Appl. No. 13/687,304, 15 pages.

Office Action dated May 28, 2014 for U.S. Appl. No. 13/687,304, 13 pages.

Office Action dated Sep. 16, 2014 for U.S. Appl. No. 13/687,304, 11 pages.

Office Action dated Oct. 20, 2015 for U.S. Appl. No. 14/480,051, 25 pages.

International Search Report and Written Opinion dated Nov. 2, 2015 for PCT Application Serial No. PCT/US2015/043329, 12 pages.

Taiwanese Office Action dated Dec. 8, 2015 for Taiwanese Patent Application Serial No. 103132242, 6 pages.

Partial International Search Report dated Jan. 4, 2016 for PCT Application Serial No. PCT/US2015/048964, 7 pages.

(56) References Cited

OTHER PUBLICATIONS

Savoia et al. "Design and Fabrication of a cMUT Probe for Ultrasound Imaging of Fingerprints" 2010 IEEE International Ultrasonics Symposium Proceedings; Publication [online] Oct. 2010 [retrieved Oct. 7, 2014] Retrieved from Internet: <http://ieeexplore.ieee.org/xpl/login.jsp?tp=&arnumber=5935836>; pp. 1877-1880.

Dausch et al. "Theory and Operation of 2-D Array Piezoelectric Micromachined Ultrasound Transducers" IEEE Transactions on Ultrasonics, Ferroelectrics, and Frequency Control, vol. 55, No. 11, Nov. 2008; Retrieved from Internet on [Dec. 8, 2014]: <https:llrti.org/pubs/dauschtuffcv55is11 p2484nov2008.pdf >.

Qiu et al. "Piezoelectric Micromachined Ultrasound Transducer (PMUT) Arrays for Integrated Sensing, Actuation and Imaging"; Sensors 2015, 15, 8020-8041; doi: 1 0.3390/s150408020; Retrieved from Internet [Dec. 8, 2015] : <http://www.mdpi.com/1424-8220/15/4/8020/pdf>.

Chinese Office Action dated Feb. 3, 2016 for Chinese Application Serial No. 201410483646.X, 12 pages.

International Search Report and Written Opinion dated Mar. 14, 2016 for PCT Application Serial No. PCT/US2015/048964, 16 pages.

Office Action dated Apr. 14, 2016 for U.S. Appl. No. 14/480,051, 29 pages.

Office Action dated Aug. 15, 2016 for U.S. Appl. No. 14/453,326, 57 pages.

Chinese Office Action dated Aug. 1, 2016 for Chinese Application Serial No. 201410483646.X, 4 pages.

Office Action dated Jan. 8, 2016 for U.S. Appl. No. 14/800,604, 9 pages.

Final Office Action dated Jul. 6, 2016 for U.S. Appl. No. 14/800,604, 10 pages.

Office Action dated Jul. 10, 2017 for U.S. Appl. No. 15/291,599, 14 pages.

Office Action dated Sep. 6, 2017 for U.S. Appl. No. 15/477,193, 35 pages.

Office Action dated Sep. 8, 2017 for U.S. Appl. No. 15/477,202, 33 pages.

Office Action dated Apr. 3, 2017 for U.S. Appl. No. 15/291,599, 33 pages.

Office Action dated Nov. 16, 2017 for U.S. Appl. No. 15/291,599, 16 pages.

Office Action dated Dec. 15, 2017 for U.S. Appl. No. 15/367,766, 46 pages.

Office Action dated Jan. 19, 2018 for U.S. Appl. No. 15/477,193, 13 pages.

Office Action dated Jan. 29, 2015 for U.S. Appl. No. 13/687,304, 11 pages.

Office Action dated Jun. 7, 2018 for U.S. Appl. No. 15/291,599, 18 pages.

Office Action dated Jul. 10, 2018 for U.S. Appl. No. 15/367,766, 21 pages.

Final Office Action dated Mar. 5, 2018 for U.S. Appl. No. 15/477,202, 14 pages.

Office Action dated May 31, 2018 for U.S. Appl. No. 15/477,193, 16 pages.

Wygant et al., "Integration of 2D CMUT Arrays with Front-End Electronics for Volumetric Ultrasound Imaging", IEEE Transactions on Ultrasonics, Ferroelectrics, And Frequency Control, Feb. 2008, 16 pages, vol. 55, No. 2.

Fesenko, Pavlo, "Capacitive Micromachined Ultrasonic Transducer (cMUT) for Biometric Applications", Thesis for the Degree of Erasmus Mundus Master of Nanoscience and Nanotechnology, 2012, 46 pages, Goteborg, Sweden.

Vanagas et al., "Study of the CMUT Operation in Microfluidic Application", Paper 10: 344—2012 IEEE International Ultrasonics Symposium, 2012, 4 pages.

Feng et al., "Touch Panel with Integrated Fingerprint Sensors Based User Identity Management", 7 pages.

Singh, Rahul, "Fingerprint Sensing Techniques, Devices and Applications", Apr. 30, 2003, 31 pages.

Wikipedia, "Capacitive Micromachined Ultrasonic Transducers", 2014, 4 pages.

Schmitt et al., "Surface Acoustic Impediography: A New Technology for Fingerprint Mapping and Biometric Identification: A Numerical Study", Proc. SPIE 5403, Sensors, and Command, Control, Communications, and Intelligence (C3I) Technologies for Homeland Security and Homeland Defense III, 309, Sep. 15, 2004, 7 pages.

Khuri-Yakub, "General Description and Advantages of CMUTs", 2014, 5 pages.

Final Office Action received for U.S. Appl. No. 15/477,193 dated Dec. 3, 2018, 18 pages.

MICROFAB, "CMUT Working Principle", 2014, 2 pages.

Non-Final Office Action received for U.S. Appl. No. 15/367,766 dated Feb. 8, 2019, 21 pages.

Official Communication for European Patent Application No. 15 767 646.1-1207 dated Feb. 26, 2019, 11pgs.

Tsai et al., "Versatile CMOS-Mems integrated piezoelectric platform" 2015 Transducers—2015 18th International Conference on Solid-State Sensors, Actuators and Microsystems (Transducers), IEEE, Jun. 21, 2015 (Jun. 21, 2015), pp. 2248-2251, XP033189793 DOI: 10.1109/TRANSDUCERS.2015.7181409.

Chinese Office Action and Search Report for Chinese Application Serial No. 201580054319.5 dated Feb. 27, 2019, 26 pages.

Office Action dated Jun. 18, 2019 for U.S. Appl. No. 15/477,193, 18 pages.

* cited by examiner

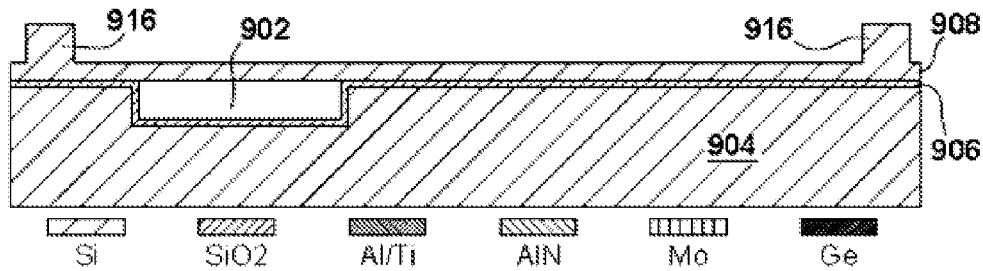
Fig. 12A(i)
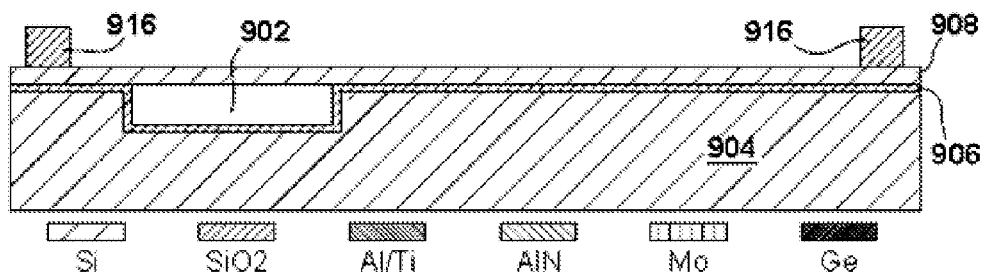
Fig. 12A(ii)
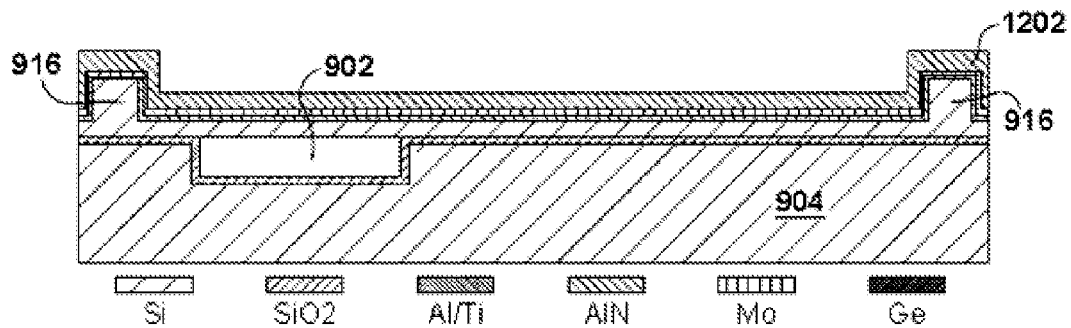
Fig. 12B(i)
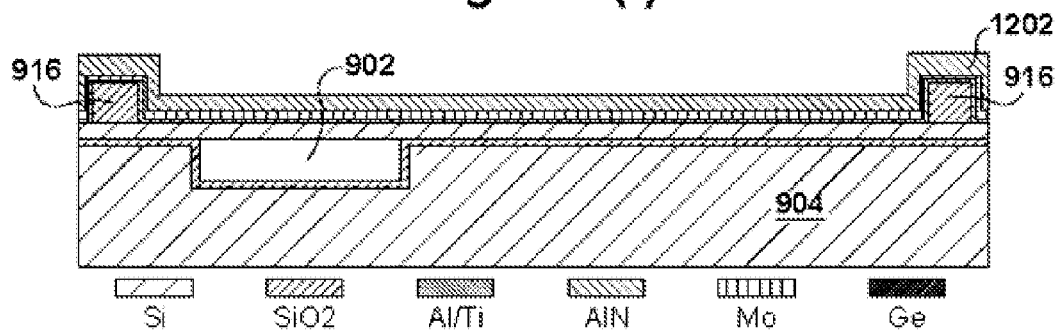
Fig. 12B(ii)

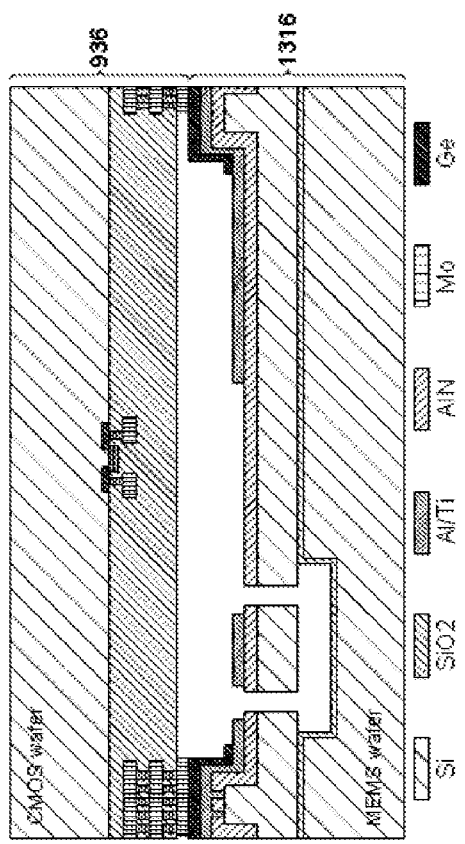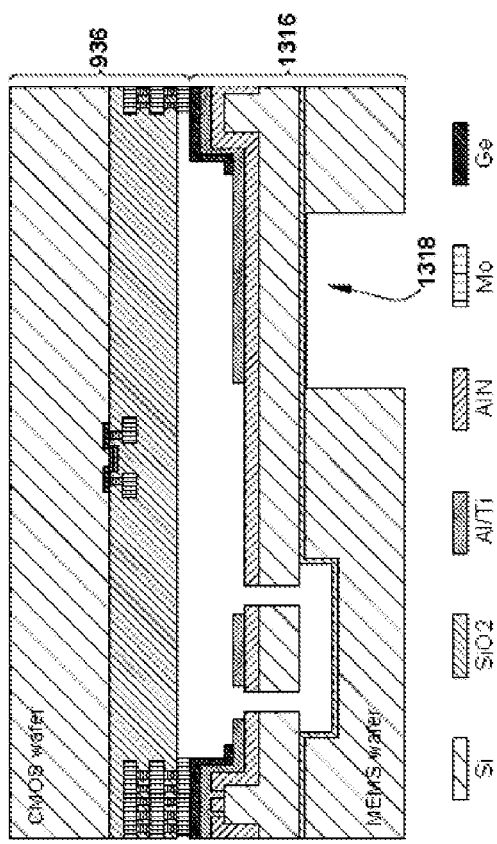

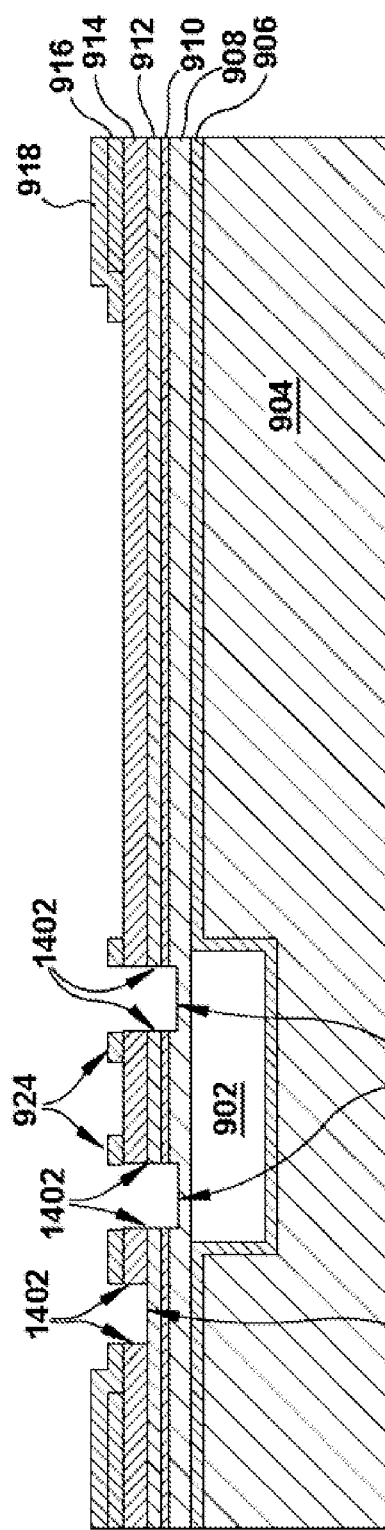
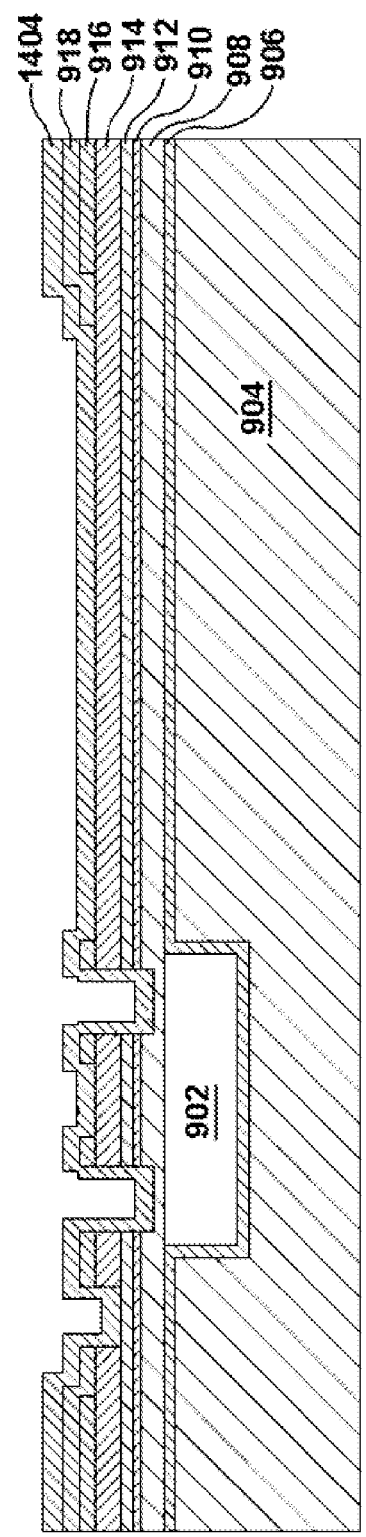

INTEGRATED PIEZOELECTRIC MICROELECTROMECHANICAL ULTRASOUND TRANSDUCER (PMUT) ON INTEGRATED CIRCUIT (IC) FOR FINGERPRINT SENSING

PRIORITY CLAIM

This patent application is a continuation-in-part application that claims priority to U.S. patent application Ser. No. 14/480,051, filed Sep. 8, 2014, entitled "ALUMINUM NITRIDE (AlN) DEVICES WITH INFRARED ABSORPTION STRUCTURAL LAYER," which is a non-provisional application of U.S. Provisional Patent Application Ser. No. 61/880,110, filed Sep. 19, 2013, entitled "ALUMINUM NITRIDE (AlN) DEVICES WITH IR ABSORPTION STRUCTURAL LAYER AND METHOD OF FABRICATING THE SAME," and which is a continuation-in-part application that claims priority to U.S. patent application Ser. No. 13/687,304, filed Nov. 28, 2012, entitled "MEMS DEVICE AND PROCESS FOR RF AND LOW RESISTANCE APPLICATIONS," this patent application is a continuation-in-part application that claims priority to U.S. patent application Ser. No. 14/453,326, filed Aug. 6, 2014, entitled "PIEZOELECTRIC ACOUSTIC RESONATOR BASED SENSOR," and this patent application is a non-provisional application of U.S. Provisional Patent Application Ser. No. 62/153,480, filed Apr. 27, 2015, entitled "INTEGRATED PMUT ON IC FOR FINGERPRINT SENSING." The entirety of the aforementioned applications are incorporated by reference herein.

TECHNICAL FIELD

The subject disclosure relates to microelectromechanical (MEMS) devices, to piezoelectric MEMS devices for fingerprint sensing, and more particularly to integrated piezoelectric MEMS transducers (PMUTs) on integrated circuit (IC) for fingerprint sensing.

BACKGROUND

Microelectromechanical systems enable integration of both microelectronic circuits and mechanical structures on a single chip or device, thereby significantly lowering fabrication costs and/or chip size. For instance, compared with their bulk piezoelectric counterparts, MEMS ultrasound transducers (MUT) can have applications not possible in conventional bulk piezoelectric devices, e.g., medical imaging, such as intravascular guiding and diagnosis, fingerprint detection, etc. For example, traditional manufacturing methods are ineffective in creating area array interconnection and reduced transducer sizes.

However, MUT devices, as an alternative method for fingerprint detection typically require MUT devices to be manufactured in the resolution of at least 300 dots per inch (dpi) or higher e.g., approximately 85 micrometer (μm) pixel size. Conventional manufacturing process flows, e.g., with traditional polishing and sawing from bulk piezoelectric materials have not been able to achieve required resolutions, whereas a capacitive MUT (CMUT) linear array can provide such resolution. However, CMUT linear arrays are subject to skin condition and sensor contamination, which can deteriorate the accuracy of fingerprint detection devices employing CMUT linear arrays.

It is thus desired to provide integrated piezoelectric MEMS transducers (PMUTs) on integrated circuit (IC) for fingerprint sensing that improve upon these and other deficiencies. The above-described deficiencies are merely intended to provide an overview of some of the problems of conventional implementations, and are not intended to be exhaustive. Other problems with conventional implementations and techniques, and corresponding benefits of the various aspects described herein, may become further apparent upon review of the following description.

SUMMARY

The following presents a simplified summary of the specification to provide a basic understanding of some aspects of the specification. This summary is not an extensive overview of the specification. It is intended to neither identify key or critical elements of the specification nor delineate any scope particular to any embodiments of the specification, or any scope of the claims. Its sole purpose is to present some concepts of the specification in a simplified form as a prelude to the more detailed description that is presented later.

In a non-limiting example, an exemplary MEMS device can comprise a MEMS ultrasound transducer (MUT) structure and a piezoelectric material disposed within the MEMS device comprising a piezoelectric MUT (PMUT) array of a fingerprint sensor adapted to sense a characteristic of a fingerprint placed adjacent to the MUT structure. An exemplary MEMS device can further comprise a first metal conductive layer disposed on the piezoelectric material and a plurality of metal electrodes configured to form electrical connections between the first metal conductive layer, the piezoelectric material, and a complementary metal oxide semiconductor (CMOS) structure, wherein the pMUT structure and the CMOS structure are vertically stacked.

In another non-limiting example, an exemplary MEMS device can comprise a CMOS device wafer associated with an integrated PMUT array of a fingerprint sensor and having a plurality of cavities configured in an array. An exemplary MEMS device can further comprise a first metal conductive layer disposed on the CMOS device wafer and over the plurality of cavities, a piezoelectric material disposed on the first metal conductive layer, and a second metal conductive layer, disposed on the piezoelectric material, electrically coupling the second metal conductive layer and at least one CMOS device wafer electrode, and electrically coupling the first metal conductive layer to at least one other CMOS device wafer electrode, wherein the plurality of cavities, the piezoelectric material, the first metal conductive layer, and the second metal conductive layer are configured as a plurality of PMUT structures.

In a further non-limiting example, exemplary methods are described directed to PMUTs suitable for integration with CMOS integrated circuits (ICs), as well as PMUT arrays having high fill factor for fingerprint sensing.

These and other embodiments are described in more detail below. The following description and the annexed drawings set forth certain illustrative aspects of the specification. These aspects are indicative, however, of but a few of the various ways in which the principles of the specification may be employed. Other advantages and novel features of the specification will become apparent from the following detailed description of the specification when considered in conjunction with the drawings.

BRIEF DESCRIPTION OF THE DRAWINGS

Various non-limiting embodiments are further described with reference to the accompanying drawings, in which

FIGS. 12(a)(i), 12(a)(ii), 12(b)(i), and 12(b)(ii) illustrate cross-section views of a MEMS structure in accordance with a twelfth embodiment;

FIGS. 13A-13H illustrate cross-section views of a MEMS structure in accordance with a thirteenth embodiment;

FIGS. 14A-14C illustrate cross-section views of a MEMS structure in accordance with a fourteenth embodiment;

DETAILED DESCRIPTION

Figure 1A:
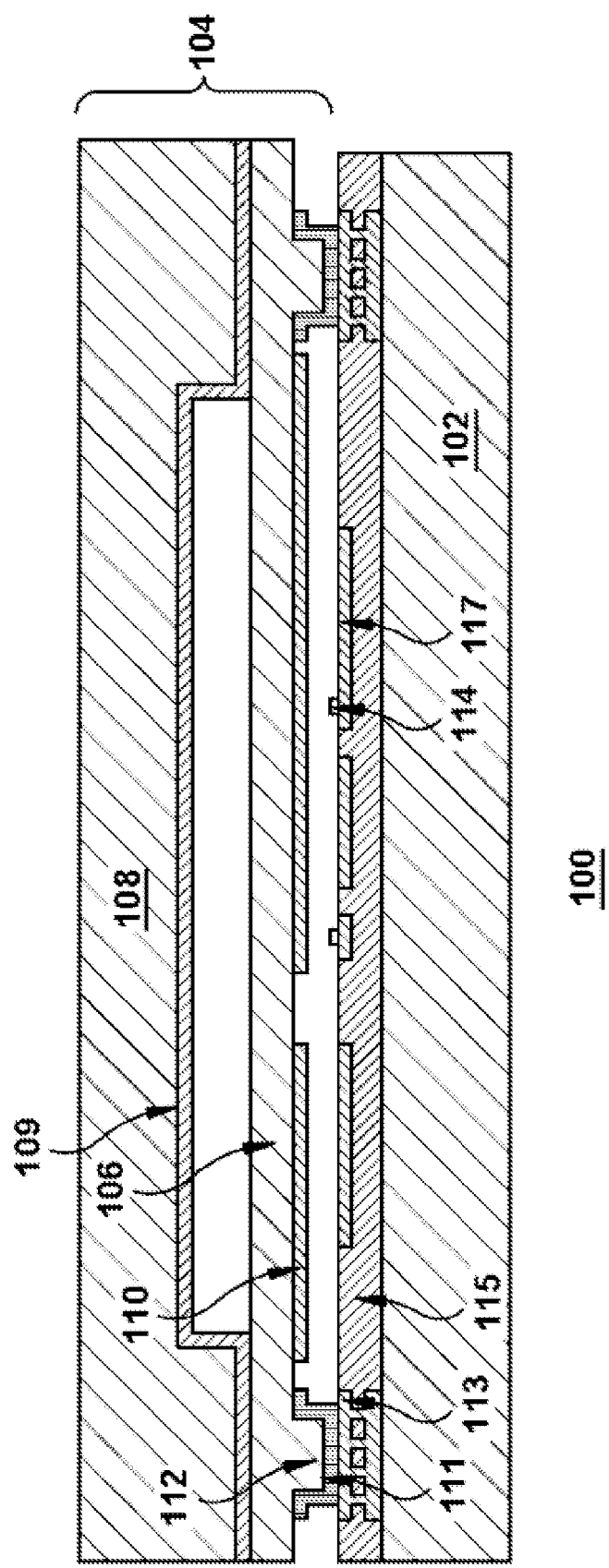
FIG. 1A illustrates a cross-section view of a MEMS structure in accordance with a first embodiment.

While a brief overview is provided, certain aspects of the subject disclosure are described or depicted herein for the purposes of illustration and not limitation. Thus, variations of the disclosed embodiments as suggested by the disclosed apparatuses, systems, and methodologies are intended to be encompassed within the scope of the subject matter disclosed herein.

One or more embodiments are now described with reference to the drawings, wherein like reference numerals are used to refer to like elements throughout. In the following description, for purposes of explanation, numerous specific details are set forth in order to provide a thorough understanding of the various embodiments. It may be evident, however, that the various embodiments can be practiced without these specific details, e.g., variations in configurations, processes, and/or materials. In other instances, well-known structures and devices are shown in block diagram form in order to facilitate describing the embodiments in additional detail.

In the described embodiments microelectromechanical systems (MEMS) refers to a class of structures or devices fabricated using semiconductor-like processes and exhibiting mechanical characteristics such as the ability to move or deform. MEMS often, but not always interact with electrical signals. MEMS devices include but are not limited to gyroscopes, accelerometers, magnetometers, pressure sensors, and radio-frequency components. Silicon wafers containing MEMS structures are referred to as MEMS wafers.

In the described embodiments, MEMS device may refer to a semiconductor device implemented as a microelectromechanical system. MEMS structure may refer to any feature that may be part of a larger MEMS device. An engineered silicon-on-insulator (ESOI) wafer may refer to a SOI wafer with cavities beneath the silicon device layer or substrate. Handle wafer typically refers to a thicker substrate used as a carrier for the thinner silicon device substrate in a silicon-on-insulator wafer. Handle substrate and handle wafer can be interchanged.

In the described embodiments, a cavity may refer to an opening or recession in a substrate wafer and enclosure may refer to a fully enclosed space. Bond chamber may be an enclosure in a piece of bonding equipment where the wafer bonding process takes place. The atmosphere in the bond chamber determines the atmosphere sealed in the bonded wafers.

Additionally, a system and method in accordance with the present invention describes a class of RF MEMS devices, sensors, and actuators including but not limited to switches, resonators and tunable capacitors that are hermetically sealed and bonded to integrated circuits that may use capacitive sensing and electrostatic, magnetic, or piezoelectric actuation.

FIG. 1A illustrates a cross-section view of a MEMS structure 100 in accordance with a first embodiment. FIG. 1A shows a MEMS structure with addition of metal on the silicon structural layer. The structure includes a CMOS wafer 102 bonded to a MEMS wafer 104. The MEMS wafer 104 comprises a silicon device layer 106 fusion bonded to a handle wafer 108 through an oxide layer 109. A MEMS aluminum 110 metal layer is added to the silicon device layer 106. Adding a metal layer lowers the resistivity of the MEMS structure over that of just the silicon device layer 106 making it more attractive for applications requiring low parasitics (ex. RF MEMS, Lorentz force sensors, etc.). In this embodiment, the connection between CMOS wafer 102 and MEMS wafer 104 is created through the silicon stand-offs 112 using an aluminum-germanium eutectic bond formed by germanium 111 and aluminum 113. Apart from the stand-offs 112 the bulk of the current is carried by the metal layers 117. In an embodiment, spacers 114 composed of an insulating material such as Silicon Oxide or Silicon Nitride may be placed on bottom metal layer 117 to reduce stiction and control the gap between the top metal layer 110 and the bottom metal layer 117.

Figure 1B:
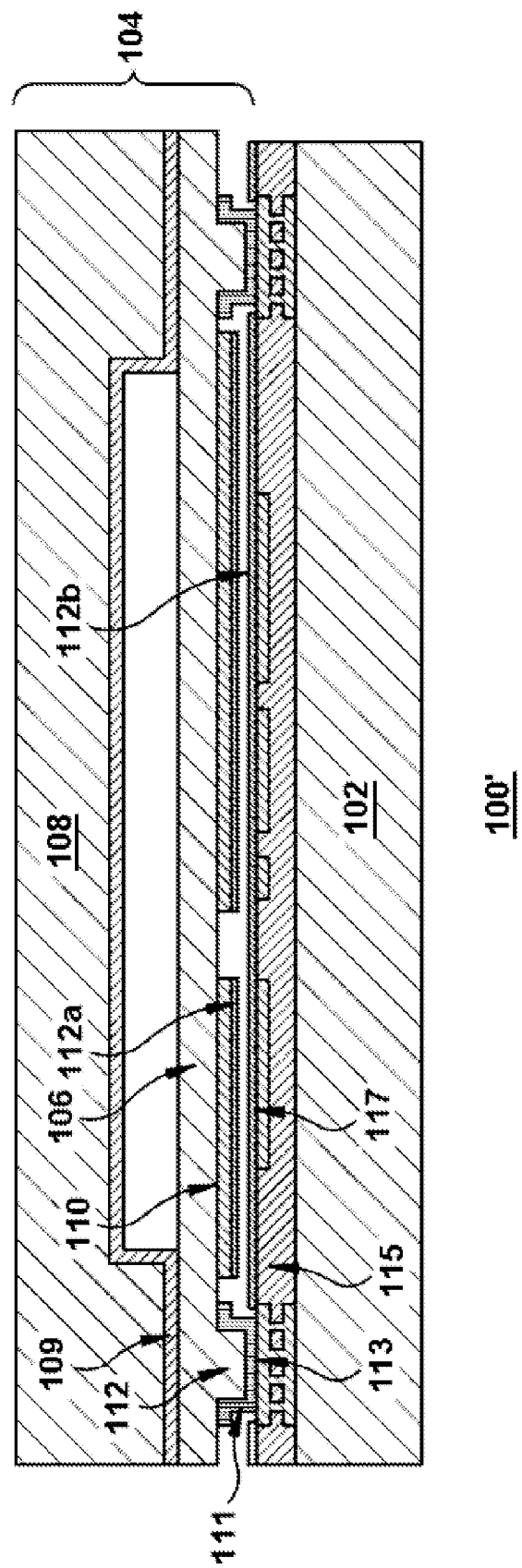
FIG. 1B illustrates a cross-section view of a MEMS structure in accordance with a second embodiment.

FIG. 1B illustrates a cross-section view of a MEMS structure 100' in accordance with a second embodiment. FIG. 1B shows a MEMS structure with additional insulating layer 112a deposited onto the MEMS aluminum 110 and insulating layer 112b deposited onto the bottom electrode 117 to prevent shorting and create a well-defined capacitive gap when the movable MEMS structure consisting of the silicon device layer 106, MEMS aluminum 110, and insulating layer 112a are brought into contact with the electrodes on the CMOS wafer 102.

Figure 2:
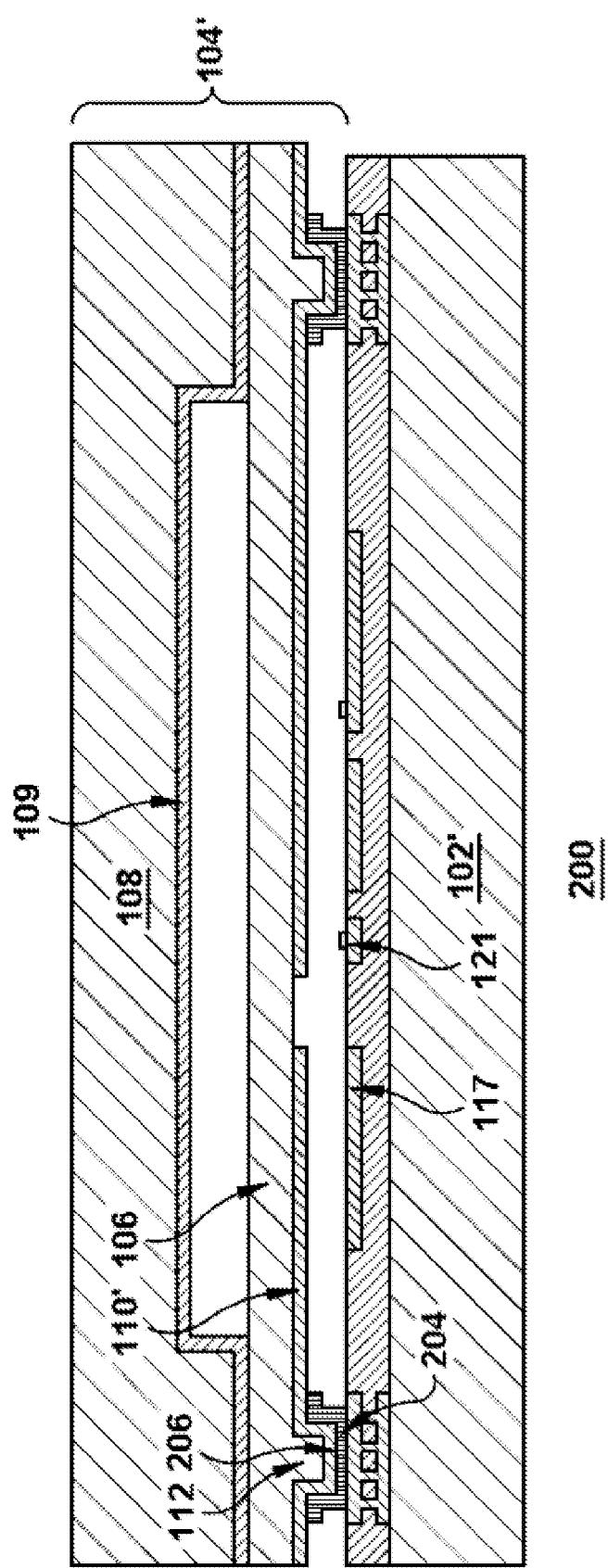
FIG. 2 illustrates a cross-section view of a MEMS structure in accordance with a third embodiment.

FIG. 2 illustrates a cross-section view of a MEMS structure 200 in accordance with a third embodiment. FIG. 2 shows a MEMS structure similar to FIG. 1A. However, in this embodiment the electrical connection between the CMOS wafer 102' and the MEMS wafer 104' occurs through physical contact between the CMOS aluminum 204 on the CMOS wafer 102' and the MEMS aluminum 110' on the MEMS wafer 104' connected by an Aluminum-Germanium layer created by the eutectic reaction between germanium 206 and CMOS aluminum 113' on the CMOS wafer 102' and the MEMS aluminum 110' on the MEMS wafer 104'. One possible risk of this embodiment is a preferential reaction of the germanium 206 with the MEMS aluminum 110' (since that is the layer it is directly deposited on) with a possibly insufficient reaction with the CMOS aluminum 113'. The insufficient reaction may lead to poor bonds and marginal electrical connections.

Figure 3:
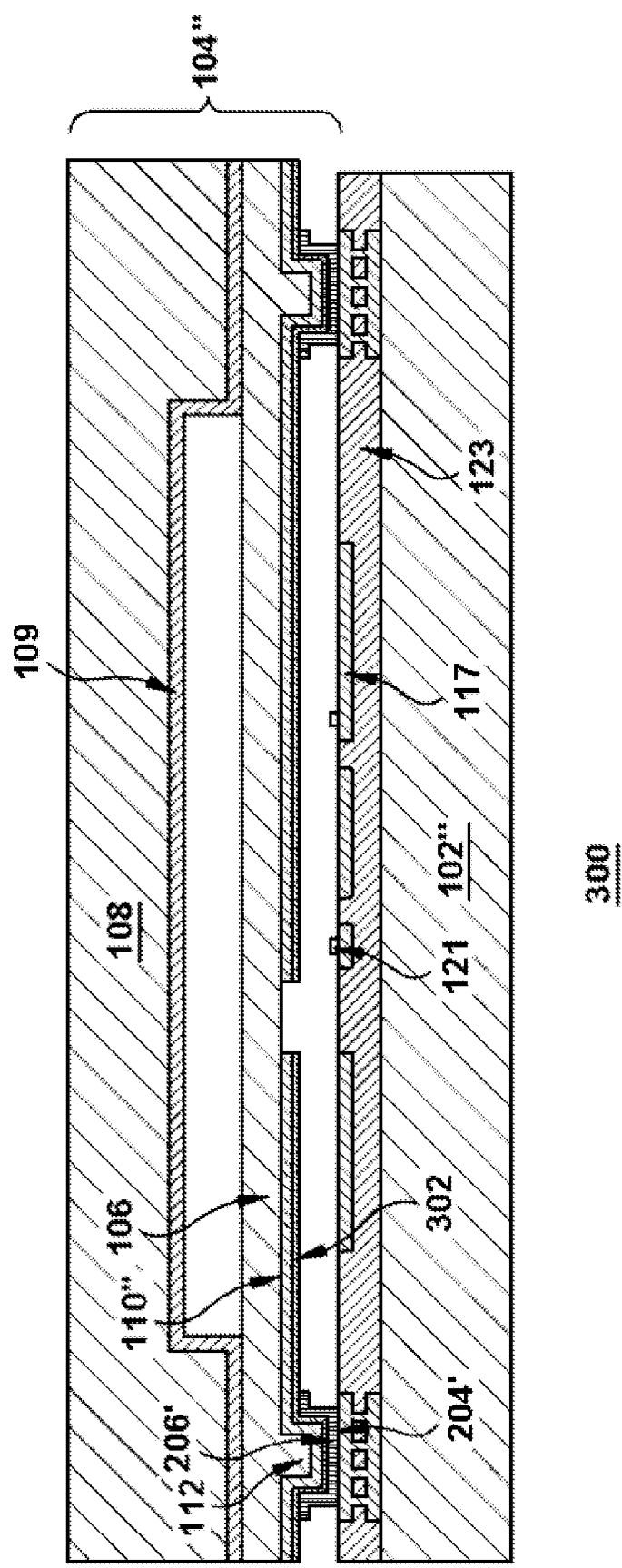
FIG. 3 illustrates a cross-section view of a MEMS structure in accordance with a fourth embodiment.

FIG. 3 illustrates a cross-section view of a MEMS structure 300 in accordance with a fourth embodiment. FIG. 3 shows a MEMS structure identical to FIG. 2 with the exception of a bather layer 302 deposited between the MEMS aluminum 110" and germanium 206'. The bather layer 302 is electrically conductive and makes an electrical contact with aluminum upon physical contact. The objective of the barrier layer 302 is to prevent a eutectic reaction between the MEMS aluminum 110" and germanium 206', leaving germanium 206' to eutectically react with the CMOS aluminum 113". One such barrier layer may be Titanium Nitride. During the eutectic reaction, the CMOS aluminum 113" will mix with germanium 206' creating an electrical contact and physical bond to the barrier layer 302 on the MEMS aluminum 110", thereby creating an electrical contact between the CMOS wafer 102" and MEMS wafer 104".

Figure 4:
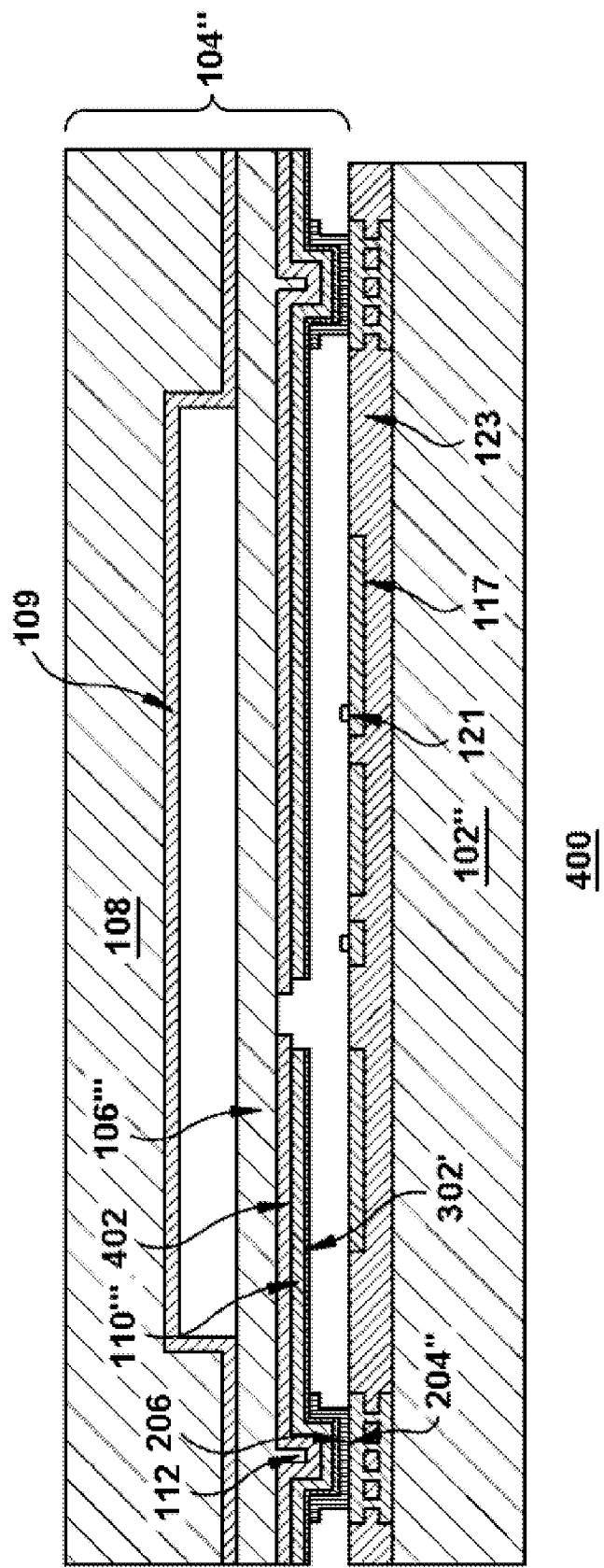
FIG. 4 illustrates a cross-section view of a MEMS structure in accordance with a fifth embodiment.

FIG. 4 illustrates a cross-section view of a MEMS structure 400 in accordance with a fifth embodiment. FIG. 4 shows a MEMS structure identical to FIG. 3, but with an insulating layer 402 deposited between the MEMS aluminum 110''' and silicon device layer 106''' thereby electrically insulating the silicon from the metal. The insulating layer 402 is needed in cases where it is not desirable to carry any electrical signal in the silicon layer (for example in RF applications where signal transmission in the silicon would produce a power loss). In this embodiment, at RF frequencies the MEMS aluminum 110''' is still capacitively coupled to the silicon device layer 106''' through the insulating layer 402. To achieve sufficient isolation the insulating layer must be sufficiently thick to minimize capacitance or the silicon must be sufficiently resistive so as to minimize electrical signal coupling into it.

Figure 5:
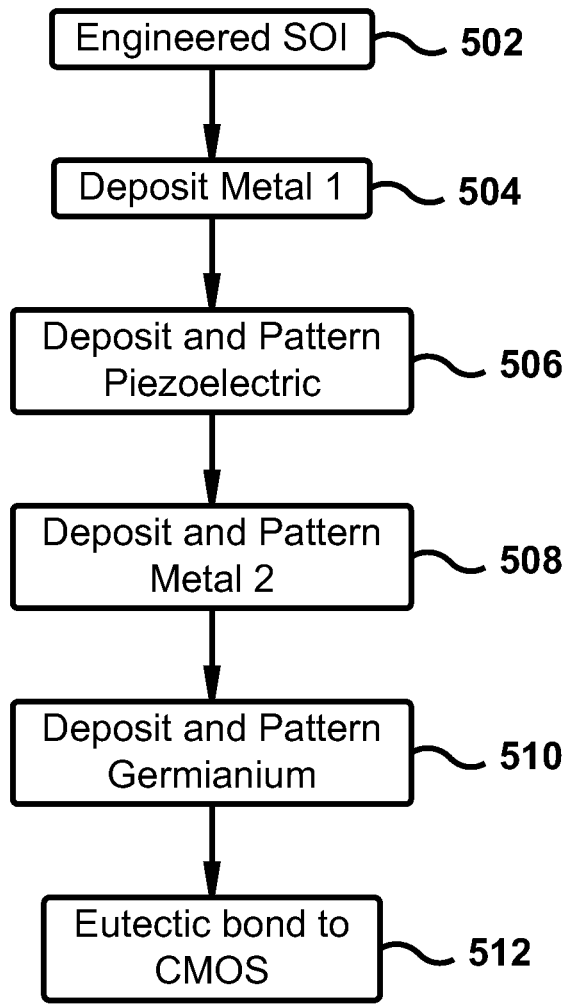
FIG. 5 is a flowchart of a process for adding a piezoelectric layer to a MEMS structure.

FIG. 5 is a flowchart of a process for adding metal and piezoelectric layers to a MEMS structure. The process starts with an Engineered SOI 502. A first metal layer (metal 1) is deposited onto the device silicon surface via step 504 followed by the piezoelectric layer deposition (e.g., Aluminum Nitride or PZT) pattern and etch via step 506. Next a second metal layer (Metal 2) deposited onto the wafer to serve as a top electrode for the piezoelectric layer as well as to provide electrical contact between Metal 1 and the CMOS substrate via step 508. A germanium layer is deposited onto Metal 1 and patterned to define germanium pads in regions where bonding to CMOS will take place via step 510. Next, the MEMS wafer is bonded to a CMOS wafer such that germanium pads eutectically react with aluminum pads on the CMOS creating electrical and physical contact between the CMOS aluminum and MEMS Metal 2 via step 512.

Figure 6:
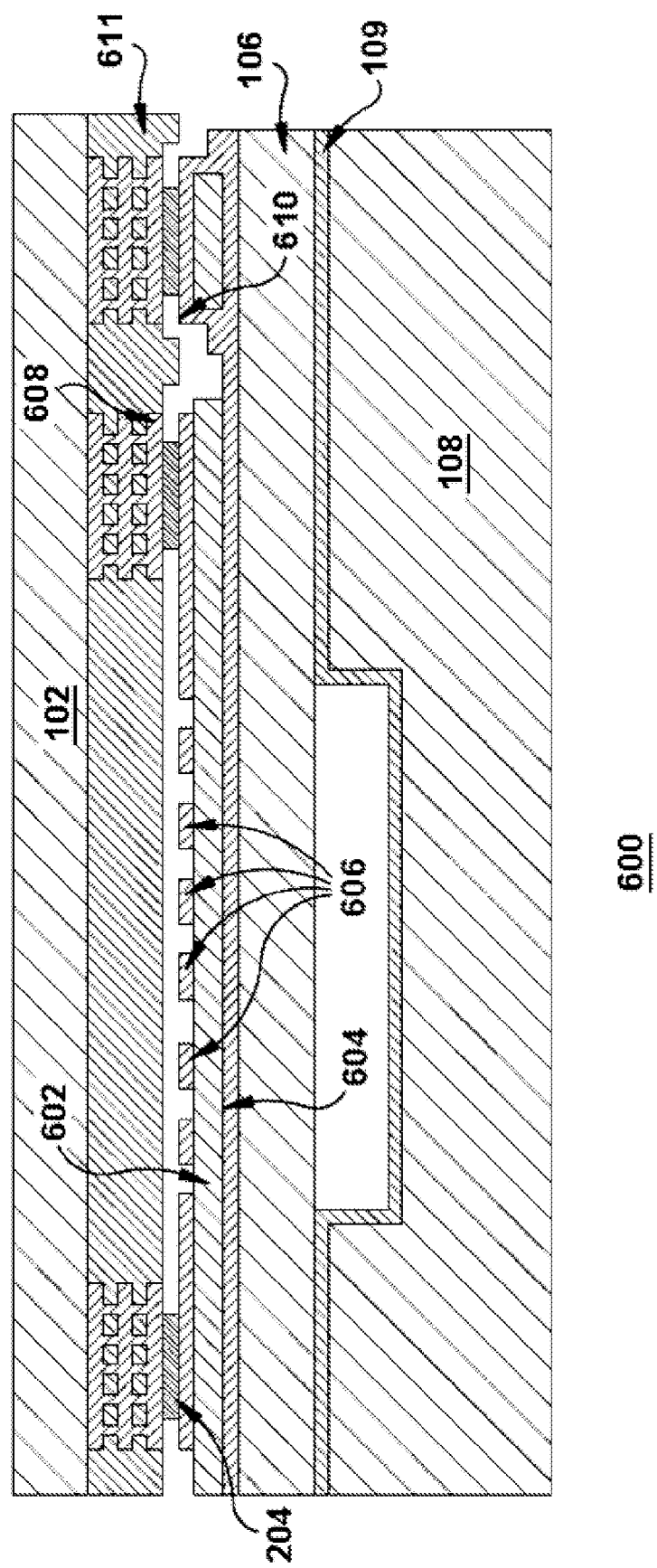
FIG. 6 illustrates a cross-section view of a MEMS structure in accordance with a sixth embodiment.

FIG. 6 illustrates a cross-section view of a MEMS structure 600 in accordance with a sixth embodiment that utilizes a piezoelectric layer. Adding a piezoelectric layer 602 enables a range of applications including acoustic resonators and filters and piezo-actuated devices. To operate, the piezoelectric layer 602 typically requires a bottom electrode 604 and top electrodes 606. The bottom electrode 604 may comprise a first metal layer (metal 1) (Ex. Aluminium, Ruthenium, Tungsten, Molybdenum or Platinum). In another embodiment, a silicon device layer can be used as a bottom electrode 604. The top electrode 606 and interconnect 610 are composed of a second metal layer (metal 2) (Ex. Aluminum). The top electrode 606 and interconnect 610 make physical and electrical contact to the CMOS aluminum pads 608 using an Aluminum Germanium bond. The bottom electrode 604 may make physical and electrical contact to the interconnect 610 thereby connecting to the CMOS wafer. Electrical potentials may be applied between top electrodes 606 and the bottom electrode 604 or between individual top electrodes 606. These potentials create electric fields to induce strains within the piezoelectric material.

Figure 7:
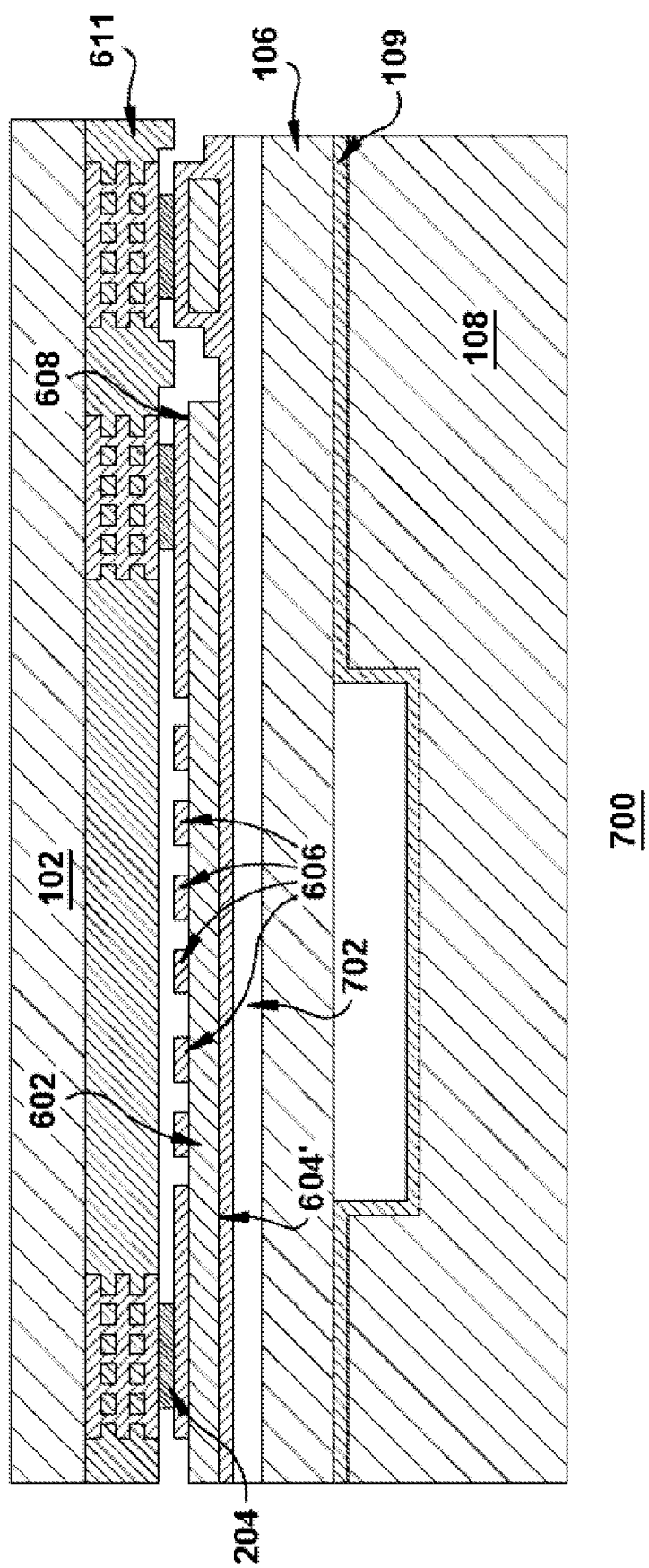
FIG. 7 illustrates a cross-section view of a MEMS structure in accordance with a seventh embodiment.

FIG. 7 illustrates a cross-section view of a MEMS structure 700 in accordance with a seventh embodiment. FIG. 7 shows the same structure as in FIG. 6 with an addition of a silicon dioxide layer 702 between the device layer silicon 106 and metal layer, 604". The silicon dioxide layer, 702 serves as a temperature stabilization layer that improves frequency stability of the resonator or filter over temperature by offsetting the positive Young's modulus temperature coefficient of silicon with the negative Young's modulus temperature coefficient of silicon oxide.

Figure 8:
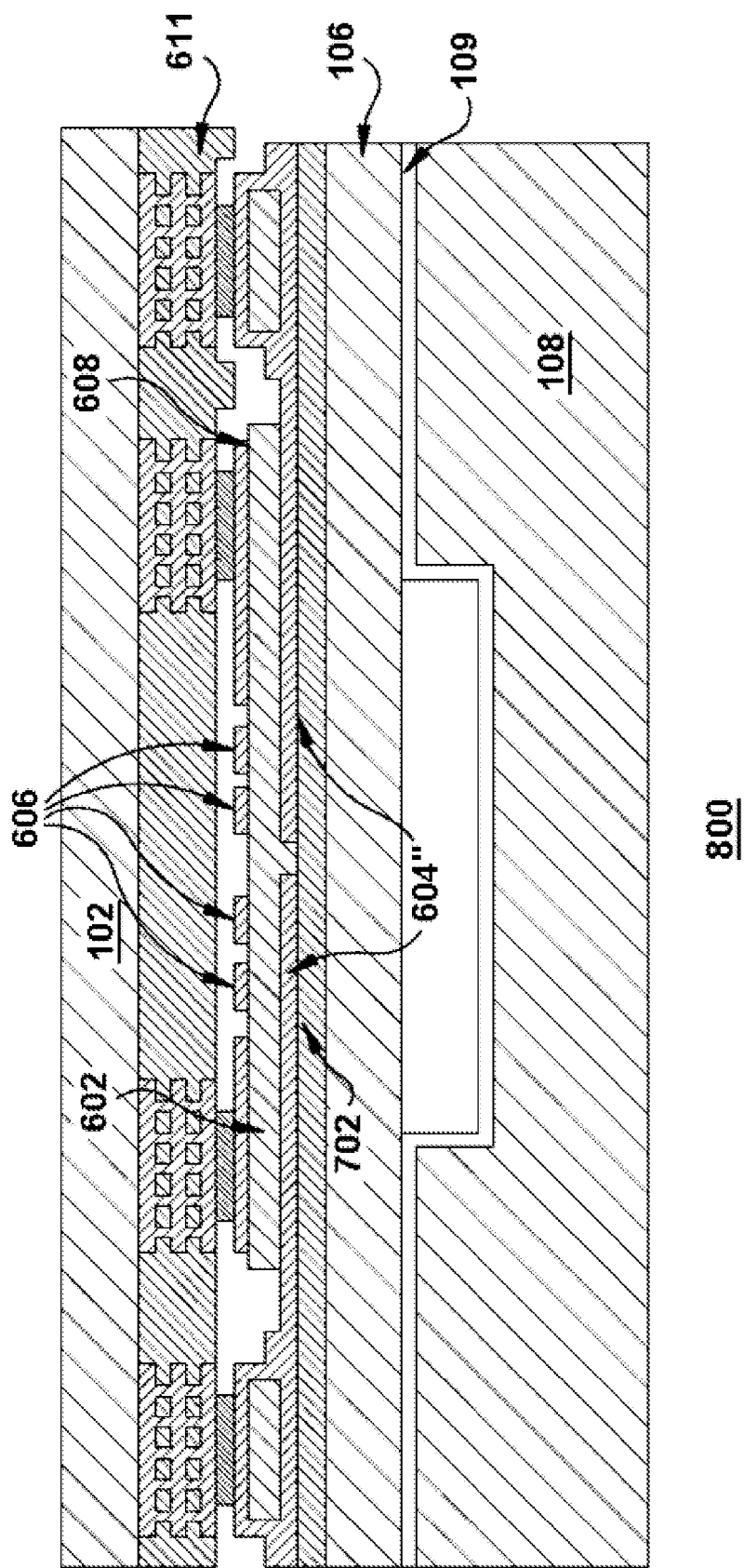
FIG. 8 illustrates a cross-section view of a MEMS structure in accordance with an eighth embodiment.

FIG. 8 illustrates a cross-section view of a MEMS structure 800 in accordance with a eighth embodiment. FIG. 8 shows the same structure as in FIG. 7 with an addition of a patterned bottom electrode 604". By patterning the bottom electrode 604", multiple potentials may be applied to different sections of the bottom surface of the piezoelectric material 602, leading to more design flexibility and potentially more efficient devices. For resonator applications, for example, the ability to input electrical signals on both the bottom and top of the piezoelectric structure can lead to higher coupling efficiency. In further embodiments, the subject application provides disclosure of a microelectromechanical system (MEMS) integration flow to incorporate aluminum nitride (AlN) on an engineering substrate and a top electrode layer combined with aluminum germanium (AlGe) with complementary metal-oxide-semiconductor (CMOS) wafers/layers/substrates.

In addition to the foregoing, the subject application further describes a MEMS integration flow that comprises starting wafers/layers/substrates (e.g., complementary metal-oxide-semiconductor (CMOS) wafers/layers/substrates, MEMS handle wafers/layers/substrates, and/or MEMS device wafers/layers/substrates) and a plurality of masking layers, for example, ten masking layers, though, as will be appreciated by those of ordinary skill, a fewer or a greater number of masking layers can be utilized without unduly departing from the generality and scope of the subject disclosure.

Typically, the MEMS handle wafers/layers/substrates can be patterned with back-side alignment mark layers used for front-to-back alignment after fusion bonding. Cavities that define suspended MEMS structures can also be etched in a front-side of the MEMS handle wafers/layers/substrates. The MEMS handle layers/wafers/substrates can then be oxidized and fusion-bonded to MEMS device layers/wafers/substrates.

The MEMS device layers/wafers/substrates can, for example, comprise silicon (Si) structural layers that can be ground and polished to target thicknesses, at which point aluminum nitride seed layers can be disposed over a surface of the silicon structural layers, molybdenum layers can be deposited over the aluminum nitride seed layers, aluminum nitride stacking layers can be deposited over the molybdenum layers, and/or silicon dioxide standoff layers can be disposed on the aluminum nitride stacking layers.

The silicon dioxide standoff layers can be etched on the MEMS device layers/wafers/substrates to provide separations between the MEMS structures and the complementary metal-oxide-semiconductor wafers/layers/substrates. The aluminum nitride (AlN) stacking layers can then be patterned through a silicon dioxide hard mask with structures, bottom contacts, and/or aluminum nitride top contact masks. Additionally, aluminum, titanium, and germanium can then be deposited in sequence from bottom to top and patterned with germanium pads and electrodes. The silicon device layer can then be patterned and etched using, for instance an anisotropic etch process used to create deep penetration, steep-sided holes and trenches in layers/wafers/substrates, typically with high aspect ratios, such as deep reactive-ion etching (DRIE), to define release structures. Generally, the combination of the structures and release layers that define the fully released structure are formed on the upper cavity.

A bottom cavity can be etched in the complementary metal-oxide-semiconductor layer/wafer to allow clearance for out-of-plane moving of the MEMS structures (e.g., combinations of silicon and aluminum nitride stacking layers) or damping control. The MEMS and complementary metal-oxide-semiconductor wafers/layers/substrates can then be bonded using aluminum-germanium (Al—Ge) eutectic bonding to create hermetic seals around the MEMS structures as well as electrical interconnects between the MEMS structures and complementary metal-oxide-semiconductor circuits. Thereafter, the bonded wafer/layer can be thinned on the MEMS side to a desired thickness and a port can be formed on the polished side of the MEMS wafer/layer to create access to the surrounding environment. Silicon tabs on the MEMS wafer/layer can thereafter be removed using, for example, a dicing process to expose the complementary metal-oxide-semiconductor wire-bond pads.

Figure 9A:
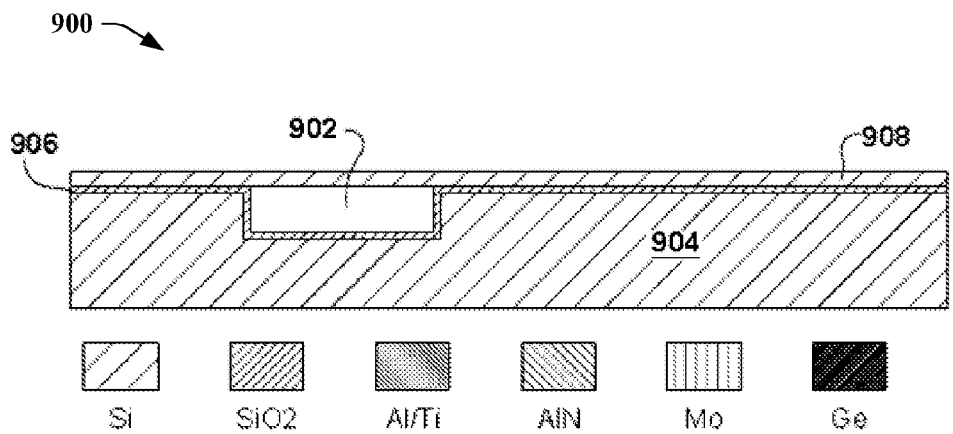
FIGS. 9A-9K illustrate cross-section views of a MEMS structure in accordance with a ninth embodiment.

In accordance with the foregoing and with reference to FIG. 9A, a cross-section of a MEMS device 900 is illustrated. The MEMS 900 can comprise a handle wafer/layer/substrate 904 that can have been patterned with back-side alignment mark layers to be employed for front-to-back alignment after fusion bonding. Further, a front side of handle wafer/layer/substrate 904 can have been etched to form cavities 902. As depicted handle wafer/layer/substrate 904 can be formed of a silicon layer/substrate into which cavities 902 can have been etched. To the handle wafer/layer/substrate 904 inclusive of cavities 902 a silicon dioxide layer/substrate 906 can be deposited on the silicon layer/substrate 904 thereby overlaying silicon layer/substrate 904 and cavities 902 formed therein. Disposed and/or deposited over silicon dioxide layer/substrate 906 and fusion bonded to the silicon dioxide layer/substrate 906 can be a substrate/layer formed of silicon 908. In accordance with an embodiment, the handle wafer/layer/substrate 904 inclusive of formed cavities 902 and silicon dioxide layer 906 can be referred to as an engineered substrate, and for purposes of this disclosure can be referred to a the MEMS handle layer.

Figure 9B:
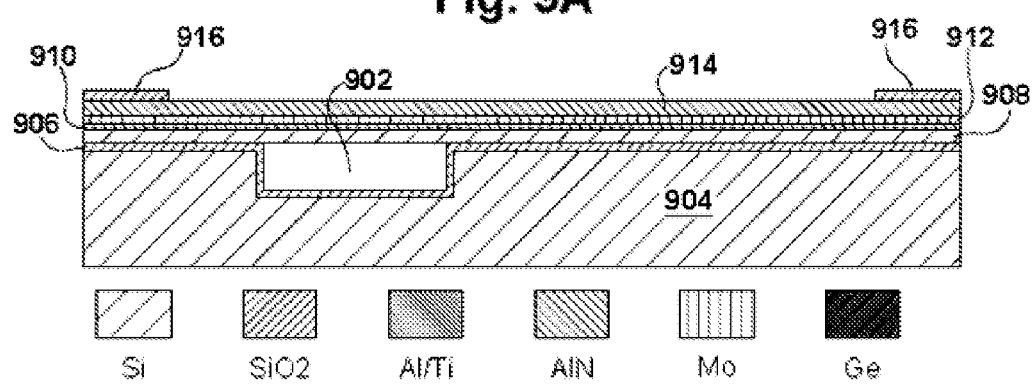

With reference to FIG. 9B that depicts a further cross-sectional view of MEMS device 900, in addition to the above noted silicon layer/substrate 904 inclusive of etched cavities 902, silicon dioxide layer/substrate 906 (silicon layer/substrate 904 inclusive of etched cavities 902 and silicon dioxide layer/substrate 906 can form and be referred to as the MEMS handle layer/wafer/substrate), and a substrate/layer 908 formed of silicon, silicon dioxide standoffs 916 can be formed on the MEMS handle layer/wafer/substrate by, for example, successively depositing aluminum nitride seed layers 910, molybdenum layers 912, and aluminum nitride stacking layers 914 over silicon substrate/layer 908, prior to etching and/or forming silicon dioxide standoffs 916. The additional deposited or disposed layers comprising the aluminum nitride seed layers 910, molybdenum layers 912, aluminum nitride stacking layers 914, and silicon dioxide standoffs 916 over silicon substrate/layer 908 can be referred to the MEMS device layer/wafer/substrate and/or piezoelectric layer/wafer/substrate.

Silicon substrate layer 908 can be the silicon structural layer of the MEMS device layer to which the MEMS handle layer (e.g., silicon layer/substrate 904 inclusive of etched cavities 902 and silicon dioxide layer/substrate 906) can have been fusion bonded to the MEMS device layer/wafer/substrate (e.g., silicon structural substrate/layer 908, aluminum nitride seed layers 910, molybdenum layers 912, aluminum nitride stacking layers 914, and standoffs 916). It should be noted that the MEMS handle layer, prior to fusion bonding of the MEMS handle layer to the MEMS device layer, can typically have been oxidized and the silicon structural layer/substrate 908 of the MEMS device layer can have been ground and polished to a target or defined thickness prior to deposition of the aluminum nitride seed layers 910, molybdenum layers 912, aluminum nitride stacking layers 914, and standoffs 916 formed of silicon dioxide. Standoffs 916 are typically formed on the MEMS device layer to provide separation between the MEMS structure and a CMOS wafer/layer/substrate.

Figure 9C:
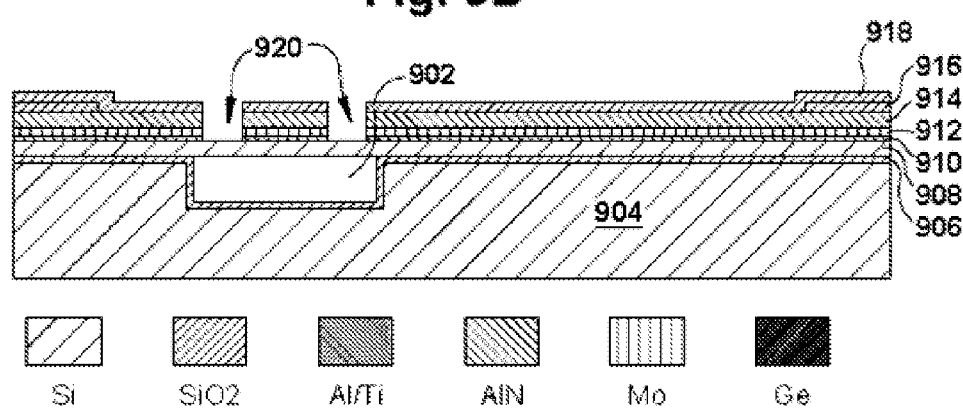
Figure 9D:
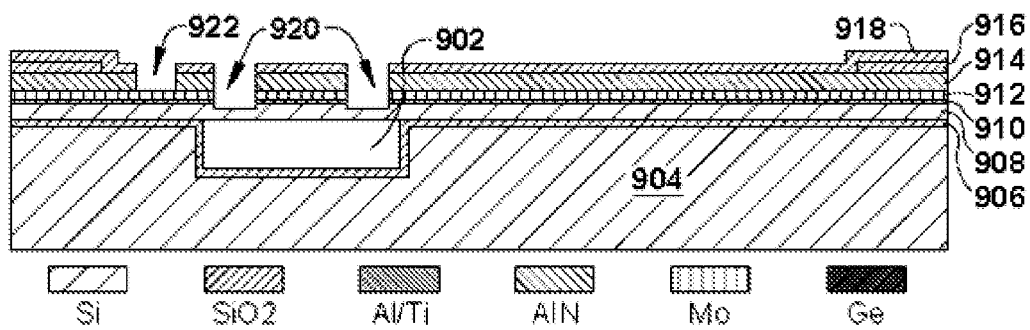
Figure 9E:
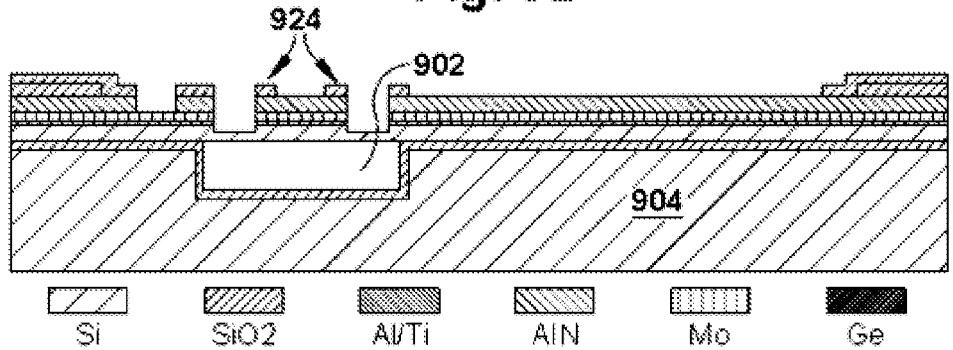

FIGS. 9C-9E provide illustration of a further cross-sectional view of MEMS device 900 including the layers described above in connection with FIGS. 9A-9B. In FIG. 9C, structure can be defined and separate bottom electrodes 920 can be carved out by first disposing or depositing a silicon dioxide hard mask 918 over the aluminum nitride stacking layers 914 and standoffs 916 and thereafter etching through silicon dioxide hard mask 918 to define the structure and carve out separate bottom electrodes 920. As will be observed, the etching process etches through layers/substrates respectively formed of silicon dioxide hard mask 918, aluminum nitride 914, molybdenum 912, and aluminum nitride seed layer 910, to the silicon structural layer/substrate 908. In FIG. 9D, a bottom electrodes contact 922 can be created. In FIG. 9E a opening etch on silicon dioxide layer 918 can be performed to define aluminum nitride top contacts 924 and avoids unnecessary HBAR resonance from the pad. Defining the structure and carving out the bottom electrodes 920, creating bottom electrode contacts 922, and defining aluminum nitride top contacts 924, as depicted in FIGS. 9C-9E, can be undertaken by patterning the aluminum nitride stacking layers through silicon dioxide hard mark 918.

Figure 9F:
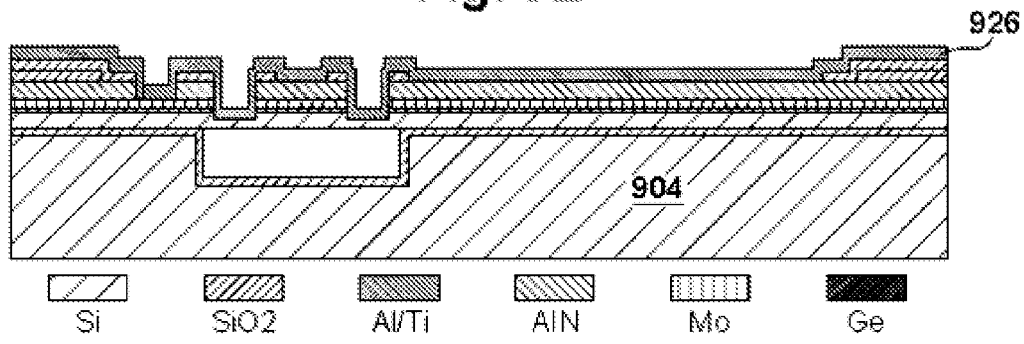
Figure 9G:
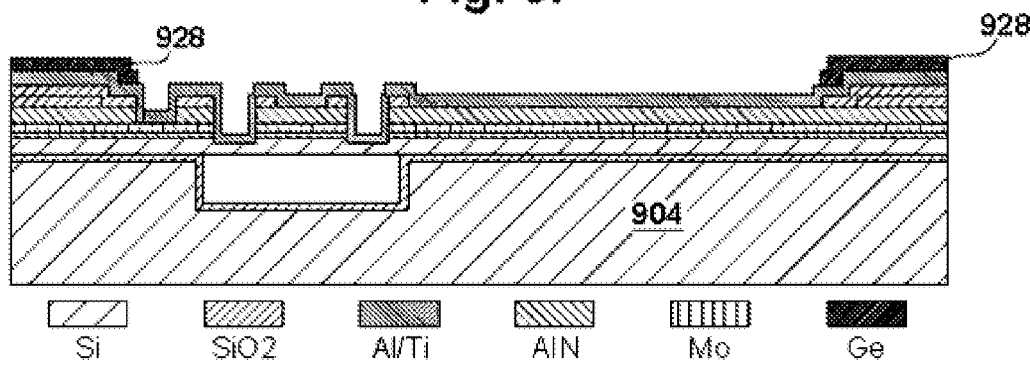
Figure 9H:
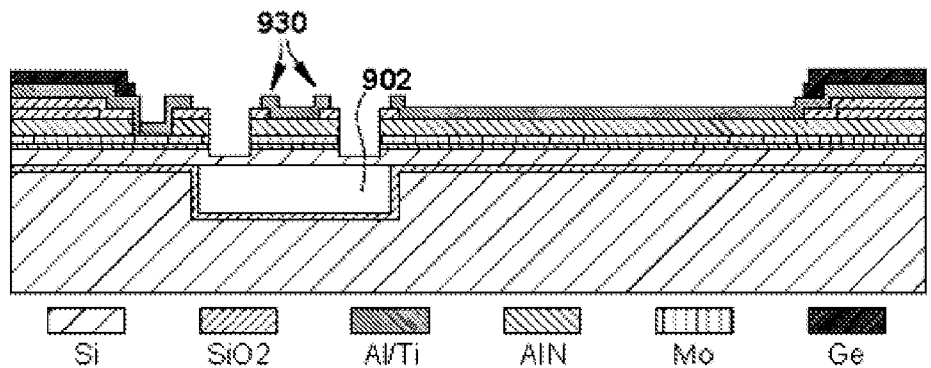
Figure 9I:
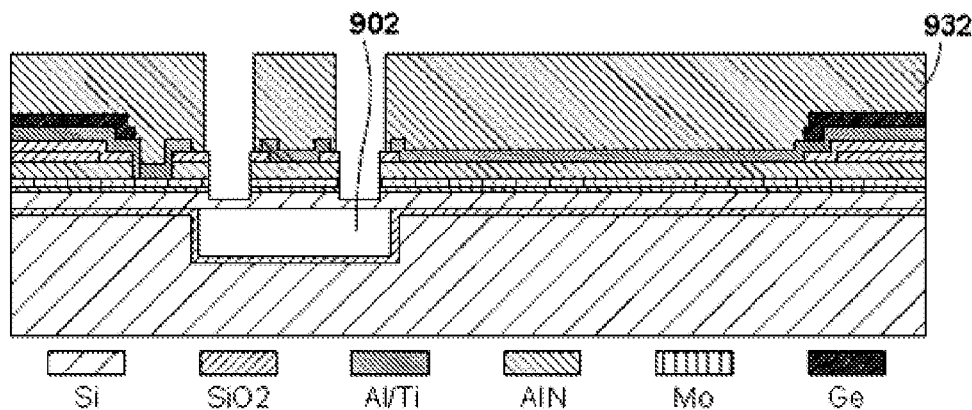

As illustrated in FIG. 9F aluminum and titanium layers 926 are deposited for the purposes of top electrode material deposition and then germanium layers 928 are deposited over the aluminum and titanium layers 926 so that germanium pads 928 and electrodes 930 can be patterned as depicted in FIGS. 9G-H. The device layer can be overlaid with a layer of photo-resist 932 and patterned and etched using deep reactive-ion etching (DRIE) to define release structures, as depicted in FIG. 9I. Only the combination of the structure and release layer can define the fully released structure 934 (See FIG. 9J) in the cavity 902.

Figure 9J:
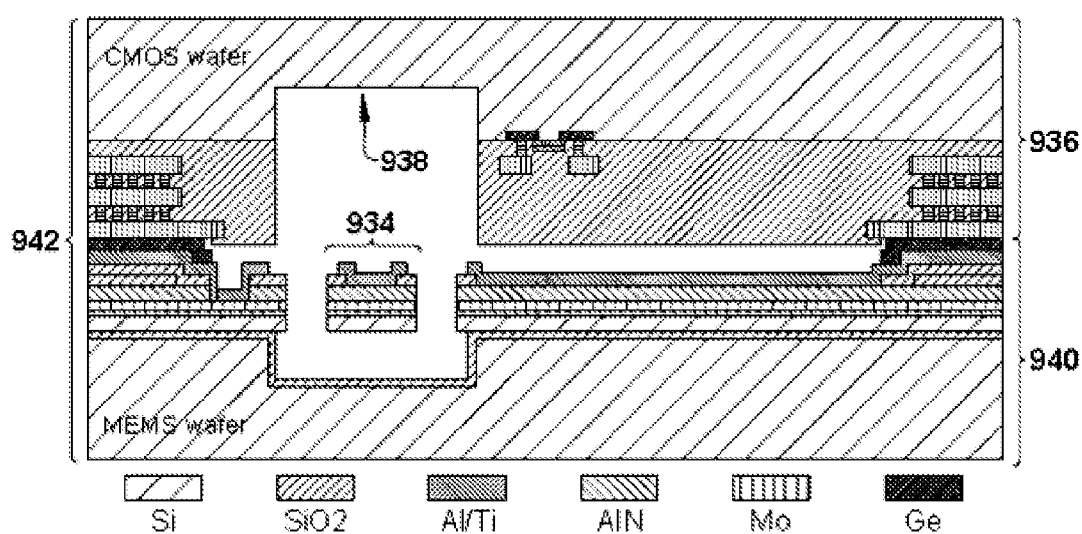
Figure 9K:
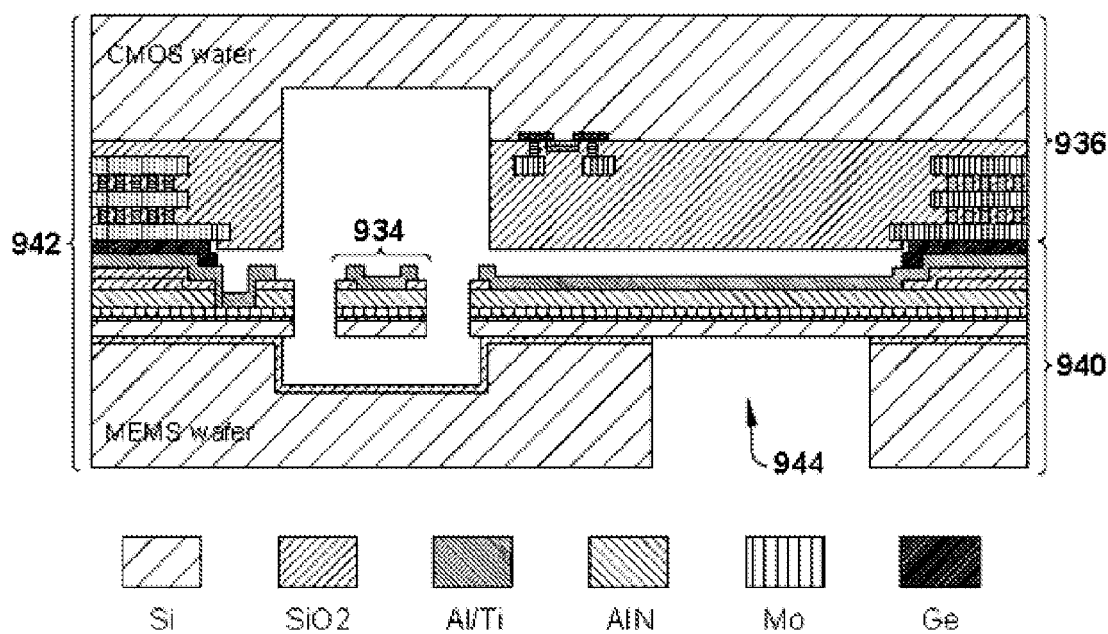

As depicted in FIG. 9J, a cavity 938 is etched into a CMOS wafer 936 to allow clearance for out-of-plane moving MEMS structures 934 and/or damping control, and thereafter the CMOS wafer 936 and MEMS device wafer 940 are bonded using an Aluminum-Germanium eutectic bond to create a hermetic seal around MEMS structure 934 and CMOS circuits and form a bonded wafer 942. The eutectically bonded wafer 942 can then be thinned, for instance, on the MEMS wafer side, to a defined or desired thickness and a port 944 can be formed on a polished side of the MEMS wafer 942 to create access to the surrounding environment, as illustrated in FIG. 9K. Additionally, silicon tabs on the MEMS wafer 942 can be removed using a dicing process to expose CMOS wire bond pads.

Figure 10:
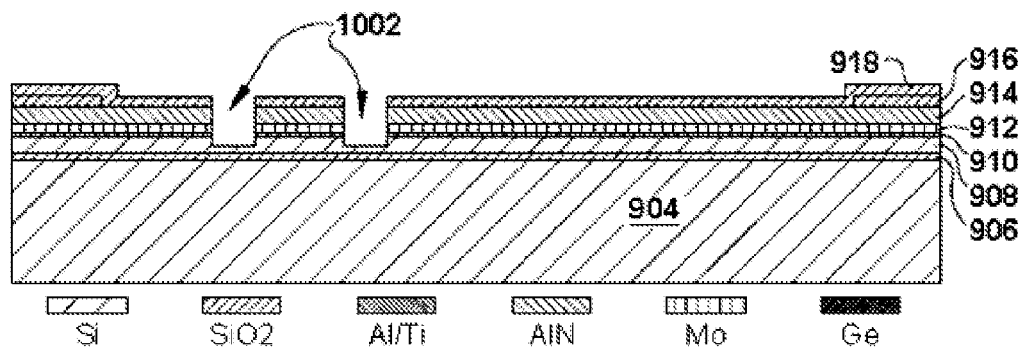
FIG. 10 illustrates a cross-section view of a MEMS structure in accordance with a tenth embodiment.

In accordance with the foregoing and in an additional embodiment as illustrated in FIG. 10, subsequent to defining structure and carving out separate bottom electrodes 920, as illustrated in FIG. 9C, but prior to creating bottom electrode contacts 922, as depicted in FIG. 9D, a partial silicon etch can be performed wherein structural silicon layer 908 (e.g., the structural silicon layer of the MEMS device wafer) can partially be further etched 1002. The partial etch 1002 can be performed to partially thin down the silicon device layer (e.g., structural silicon layer 908). The partial etch 1002 can be accomplished with a structure layer mask through silicon etch or silicon deep reactive-ion etching. It should be noted that the partial etch 1002 can be an additional etch to that previously performed to define structure and carve out separate bottom electrodes 920 as elucidated above in connection with FIG. 9C. Additionally and/or alternatively, partial etch 1002 and the etch performed to define structure and carve out separate bottom electrodes 920, as depicted in FIG. 9C, can be accomplished in a single act without unduly and/or unnecessarily departing from the intent and generality of the subject disclosure.

Figure 11:
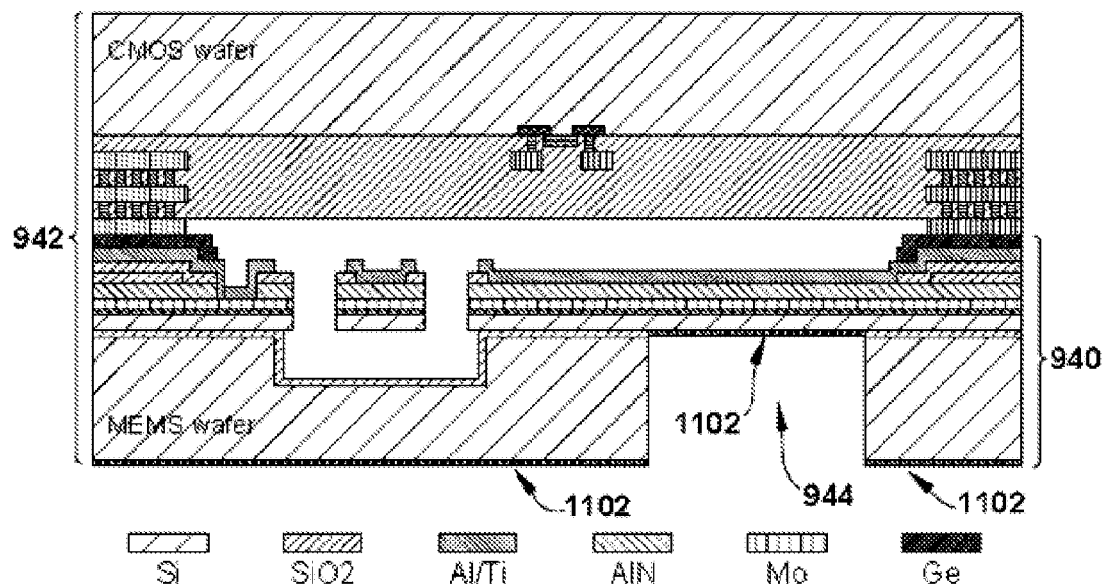
FIG. 11 illustrates a cross-section view of a MEMS structure in accordance with an eleventh embodiment.

In a further additional aspect or embodiment, as illustrated in FIG. 11, an additional act of can be performed subsequent to etching port 944 on a polished side of the MEMS wafer 942 (see e.g., FIG. 9K). In accordance with this aspect, an infra-red (IR) absorption layer 1102 can be deposited on the back of the MEMS handle wafer 940. The infra-red (IR) absorption layer 1102, as illustrated, can be disposed not only on the back of the MEMS handle wafer 940 but also in the previously etched port 944.

In accordance with a further disclosed aspect or embodiment, as illustrated in FIG. 12 additional and/or alternative standoff 916 formations techniques can be employed. As illustrated in FIG. 12(a)(i) a layer of silicon 908 can be deposited over the MEMS handle layer/wafer/substrate (e.g., silicon layer/wafer/substrate 904 inclusive of cavities 902 and silicon dioxide layer/substrate 906) and thereafter the deposited layer of silicon 908 can be partially etched to form standoffs 916, thus, referring back to FIG. 9A and as illustrated in FIG. 12(a)(i), standoffs 916 can have been formed from the structural silicon layer 908 of the MEMS device layer or piezoelectric layer/wafer/substrate. Alternatively, as depicted in FIG. 12(a)(ii) rather than partially etching into structural silicon layer 908, structural silicon layer 908 can be overlaid with a silicon dioxide layer and thereafter the deposited silicon dioxide layer can be patterned to create or form standoffs 916, as illustrated in FIG. 12(a)(ii).

Thereafter, and still with reference to FIG. 12, deposition of piezoelectric stacking layers 1202, as described and illustrated in connection with FIGS. 9C-9K, can be carried out as respectively depicted in FIGS. 12(b)(i) and 12(b)(ii). In the context of FIG. 12(b)(i) it will be observed that the subsequent piezoelectric stacking layers 1202, as described in relation to FIGS. 9C-9K, overlay silicon standoffs 916, whereas, in connection with FIG. 12(b)(ii), the successive layers that comprise the piezoelectric stacking layers 1202, as disclosed with respect to FIGS. 9C-9K, are deposited over silicon dioxide standoffs 916.

FIG. 13 illustrates an additional and/or alternative process flow than that described and disclosed in connection with FIGS. 9A-9K. In this instance, and as depicted in FIG. 13A, and as has been described above in relation to FIG. 12(a)(i), silicon standoffs 916 can have been formed by patterning and/or partially etching structural silicon layer 908. Thereafter, the piezoelectric layer stacking (e.g., aluminum nitride seed layers 910, molybdenum layer 912, and aluminum nitride stacking layer 914) described earlier with respect to FIG. 9B can be reduced to only an aluminum nitride layer 1302, wherein an aluminum nitride layer 1302 is overlaid and patterned 1304 on top of the structural silicon layer 908 inclusive of the formed silicon standoffs 916. As illustrated in FIGS. 13B-13H, the structural silicon layer 908 inclusive of the silicon standoffs 916 can be used as bottom electrodes. In FIG. 13C the aluminum nitride layer 1302 can be overlaid with aluminum and titanium layers 1306. As will be noted in relation to FIG. 13C, patterning in aluminum nitride layer 1302 at 1304 will be filled by the aluminum and titanium layers 1306.

Figure 13A:
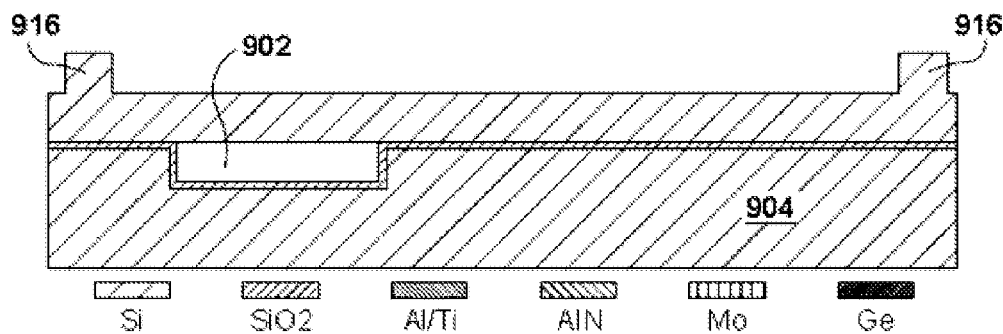
Figure 13B:
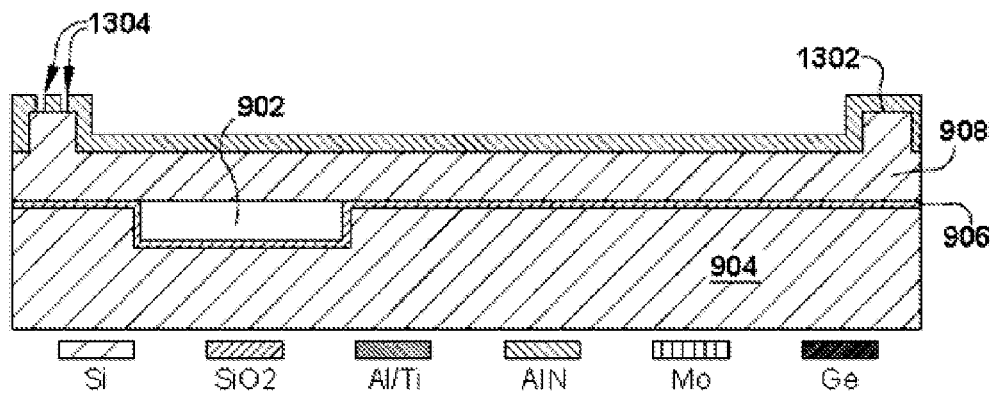
Figure 13C:
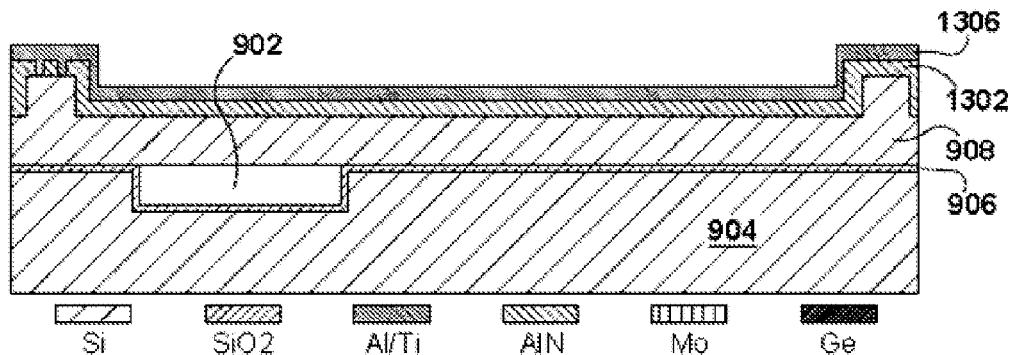
Figure 13D:
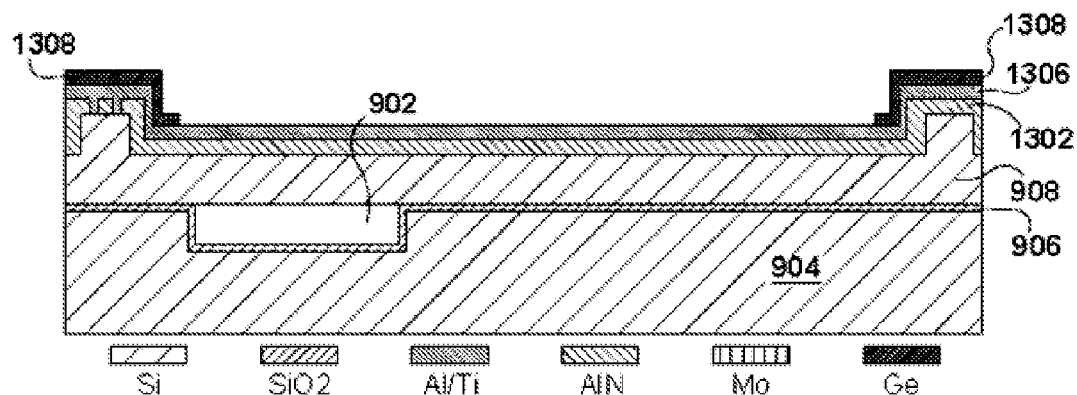
Figure 13E:
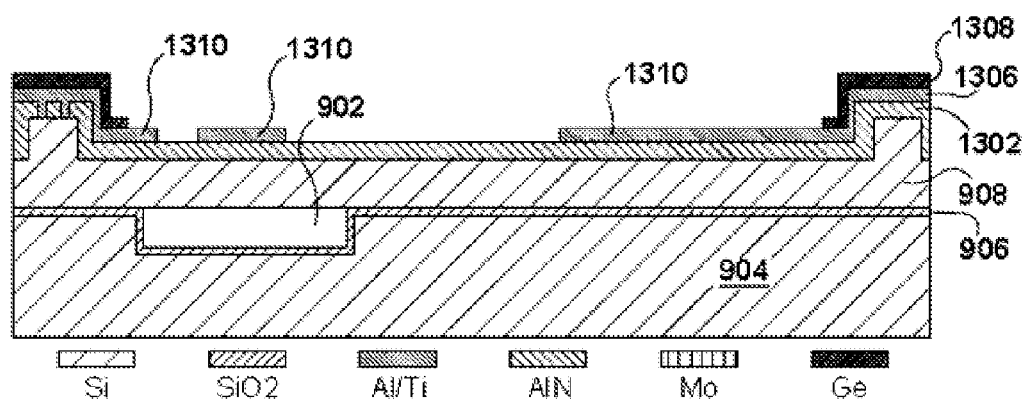
Figure 13F:
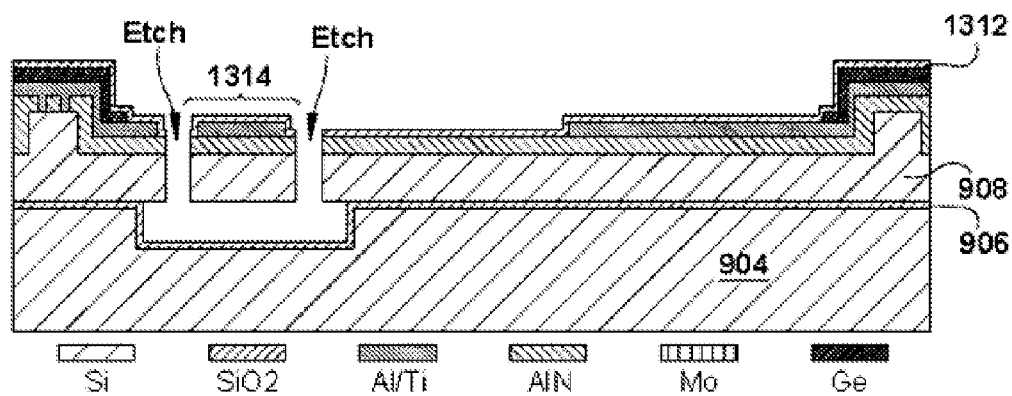

In FIG. 13D germanium pads 1308 can be defined, wherein a germanium layer can be overlaid aluminum and titanium layers 1306 to form the germanium pads 1308. Further, in FIG. 13E the previously deposited aluminum and titanium layers 1306 can be selectively patterned to define aluminum and titanium pads 1310 and to expose the underlying aluminum nitride layer 1302. In FIG. 13F a silicon dioxide hard mask 1312 can be deposited over defined germanium pads 1308, aluminum and titanium pads 1310, and exposed aluminum nitride layer 1302 and an etch or patterning performed to define the structure 1314.

Once structure 1314 has been defined, a CMOS wafer 936 can be eutectically bonded to the MEMS device wafer 1316, in a manner similar to that described in the context of FIG. 9J and illustrated in FIG. 13G. Further, on completion of the eutectic bonding of the CMOS wafer 936 to the MEMS device wafer 1316, a port 1318 can be formed on a polished side or surface of the MEMS device wafer 1316, as illustrated in FIG. 13H.

Figure 14C:
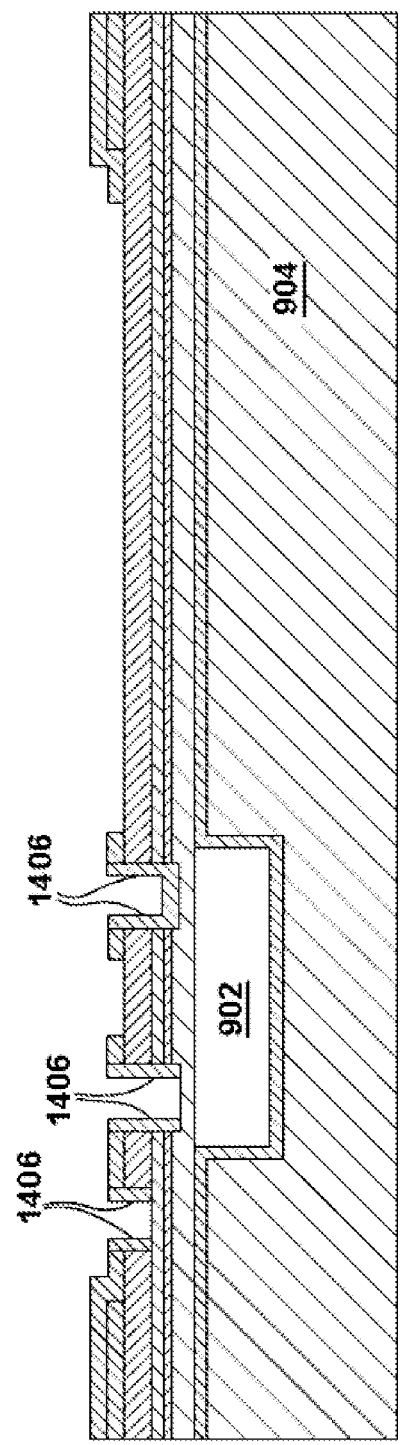

With reference now to FIGS. 14A-14C, and initially in reference to FIG. 14A, in order to provide protection to sidewalls 1402 during the various etching and/or patterning phases that can be employed to construct the described micro-electrical-mechanical device, in accordance with an embodiment, and as illustrated in FIG. 14B a silicon dioxide layer 1404 can be deposited to overlay the layers previously described in the context of FIG. 9E. It will be observed on examination of FIG. 14B that the silicon dioxide layer 1404 has been disposed to cover the sidewalls 1402 as well as bottom electrodes 920 and the bottom electrodes contact 922. Additionally, as will also have been observed on inspection of FIG. 14B, the deposited silicon dioxide layer 1404 will also have covered the aluminum nitride top contact 924. The deposition and patterning of silicon dioxide layer 1404 provides isolation Once the silicon dioxide layer 1404 has been deposited as illustrated in FIG. 14B, the silicon dioxide layer 1404 can undergo a blank reactive-ion etch to create sidewall protection 1406.

In accordance with the foregoing, the subject application discloses in one or more various embodiments and aspects a MEMS device, comprising: a first silicon substrate comprising: a handle layer comprising a first surface and a second surface, the second surface comprises a cavity; an insulating layer deposited over the second surface of the handle layer; a device layer having a third surface bonded to the insulating layer and a fourth surface; a piezoelectric layer deposited over the fourth surface of the device layer; a metal conductivity layer disposed over the piezoelectric layer; a bond layer disposed over a portion of the metal conductivity layer; and a stand-off formed on the first silicon substrate; wherein the first silicon substrate is bonded to a second silicon substrate, comprising: a metal electrode configured to form an electrical connection between the metal conductivity layer formed on the first silicon substrate and the second silicon substrate.

In accordance with the foregoing, the stand-off can be formed on the piezoelectric layer and can be formed as a silicon layer or as a silicon dioxide layer deposited on the device layer. Additionally and/or alternatively, the stand-off can be formed of silicon dioxide deposited on the piezoelectric layer.

Further, the piezoelectric layer can be patterned and etched to form a sidewall in the piezoelectric layer, wherein a first dielectric layer can be interposed between the piezoelectric layer and the metal conductive layer, and a second dielectric layer can be disposed on the sidewall of the piezoelectric layer. In addition, an opening in the handle layer can be exploited to expose the device layer, an orifice in the device layer can be used to expose the piezoelectric layer, and the device layer can include an aperture.

In accordance with a disclosed aspect the device layer can be selectively or partially removed, the piezoelectric layer can in an embodiment comprise aluminum nitride or in another embodiment can comprise: an aluminum nitride (AlN) seed layer, a bottom metal layer, and an aluminum nitride (AlN) layer. Further, an infra-red (IR) absorption layer can be deposited on a portion of the device layer and/or the infra-red (IR) absorption layer can be deposited on a portion of the piezoelectric layer.

In accordance with a further embodiment, a method is described and disclosed. The method can comprise a sequence of machine executable operations that can include depositing an insulation layer over a handle layer that comprises a first surface and a second surface, wherein the second surface comprises a cavity and the insulation layer is formed on the second surface of the handle layer; bonding a first surface of a device layer to the insulation layer; depositing a piezoelectric layer on a second surface of the device layer; depositing a metal conductivity layer over the piezoelectric layer; partially depositing a bond layer over the metal conductivity layer; forming a stand-off on the second surface of the device layer; and establishing an electrical connection between the metal conductivity layer and a silicon substrate.

Further machine executable method operations can include: depositing a silicon layer or a silicon dioxide layer to form the stand-off; depositing a silicon dioxide layer to form a stand-off positioned on the piezoelectric layer; patterning and etching of the piezoelectric layer to form a sidewall; interposing a first dielectric layer between the piezoelectric layer and the metal conductive layer; disposing a second dielectric layer on the sidewall of the piezoelectric layer; exposing the device layer via a first opening in the handle layer; and exposing the piezoelectric layer through the first opening and a second opening in the device layer.

Additional machine executed method acts can also include: selectively removing a portion of the device layer; depositing an infra-red (IR) absorption layer on a selected portion of the device layer; and depositing an infra-red (IR) absorption layer on a selected portion of the piezoelectric layer.

In accordance with further embodiments the disclosure describes a microelectromechanical device that can comprise: a first silicon substrate bonded to a second silicon substrate, comprising: an electrode on the second silicon substrate that electrically contacts a conductivity layer disposed on the first silicon substrate; the conductivity layer on the first silicon substrate is disposed over a piezoelectric layer on the first silicon substrate; the piezoelectric layer on the first silicon substrate is deposited over a device layer that comprises a stand-off formed on the first silicon substrate; and the device layer on the first silicon substrate is bonded to an dielectric layer that is deposited over a surface of a handle layer on the first silicon substrate that comprises a cavity.

In addition to the foregoing, the subject application further describes MEMS devices and fingerprint sensing. There are two kinds of finger print sensors, namely swipe-based and area-based. For mobile applications, optical method is too bulky and expensive; thermal and swipe-based RF method are not the favored due to user experience; area-based ultrasound and RF sensors have challenges to lower the manufacturing cost. In general, above conventional fingerprint sensor technologies are subject to errors due to finger contamination, sensor contamination, imaging errors, etc. Various embodiments disclosed herein provide for improved fingerprint sensor performance by measuring a frequency response of a piezoelectric acoustic resonator.

For example, a device can include an array of piezoelectric transducers, and an array of cavities that has been attached to the array of piezoelectric transducers to form an array of resonators, e.g., an array of MEMS piezoelectric acoustic resonators. A resonator, e.g., a membrane resonator, a Helmholtz resonator, etc. of the array of resonators can be associated with a first frequency response, e.g., a resonant frequency of the resonator, a Q factor of the resonator, etc. corresponding to a determination that the resonator has a non-touch baseline condition. Then a second frequency response, e.g., increase in resonant frequency of the resonator, decrease in Q factor of the resonator, etc. corresponding to a determination that the resonator has been touched, e.g., by the finger ridge. Thus the finger print map can be determined according to the frequency response changes of resonators in the resonator array.

In an embodiment, the array of piezoelectric transducers can include a piezoelectric material; a first set of electrodes that has been formed a first side of the piezoelectric material; and a second set of electrodes that has been formed on second side of the piezoelectric material—a piezoelectric transducer of the array of piezoelectric transducers corresponding to the resonator including a first electrode of the first set of electrodes and a second electrode of the second set of electrodes.

In another embodiment, the piezoelectric transducer comprises a portion of the resonator, e.g., a membrane resonator, that has been touched. In yet another embodiment, a first end of a cavity of array of cavities corresponding to a portion of the resonator, e.g., a Helmholtz resonator, that has been touched is smaller than a second end of the cavity. In an embodiment, the first end of the cavity is open to the environment, e.g., air adjacent to the device, etc. In another embodiment, the cavity has been filled with a first material corresponding to a first acoustic velocity that is different from a second acoustic velocity corresponding to a second material that is adjacent to, surrounding, etc. the cavity.

Another embodiment can include a system, e.g., a piezoelectric acoustic resonator based fingerprint sensor, etc. that can include an array of piezoelectric transducers; an array of cavities that has been attached to the array of piezoelectric transducers to form an array of resonators; a memory to store instructions; and a processor coupled to the memory, that facilitates execution of the instructions to perform operations, comprising: determining a frequency response of a resonator of the array of resonators—the resonator including a piezoelectric transducer of the array of piezoelectric transducers and a cavity of the array of cavities; and determining that the resonator has been touched, e.g., by a finger, etc. in response determining that a change in the frequency response satisfies a defined condition, e.g., a resonant frequency of the resonator has increased, a Q factor of the resonator has decreased, etc.

In one embodiment, a first portion of the cavity, e.g., corresponding to a portion of the resonator that has been touched, is smaller than a second portion of the cavity. In another embodiment, the first portion of the cavity is open to the environment. In yet another embodiment, the cavity has been filled with a first material corresponding to a first acoustic velocity that is different from a second acoustic velocity corresponding to a second material that is adjacent to the cavity.

One embodiment can include a method including forming an array of piezoelectric transducers on a first substrate; forming one or more portions of an array of cavities using a second substrate; and attaching the array of piezoelectric transducers to the second substrate to form an array of resonators. A resonator, e.g., a membrane resonator, a Helmholtz resonator, etc. of the array of resonators can be associated with a first frequency response with respect to, e.g., a resonant frequency of the resonator, a Q factor of the resonator, etc. corresponding to a determined non-touch of the resonator. Further, the resonator can be associated with a second frequency response with respect to, e.g., the resonant frequency, the Q factor, etc. corresponding to a determined touch of the resonator. Furthermore, the method can include removing the first substrate from the array of piezoelectric transducers.

In an embodiment, the forming of the array of piezoelectric transducers can include forming a first set of electrodes on a first side of a piezoelectric material, and forming a second set of electrodes on a second side of the piezoelectric material—a piezoelectric transducer of the array of piezoelectric transducers corresponding to the resonator can include a first electrode of the first set of electrodes and a second electrode of the second set of electrodes.

In another embodiment, the method can include filling a cavity of the array of cavities corresponding to the resonator, e.g., the Helmholtz resonator, with a material having a first acoustic velocity that is different from a second acoustic velocity of the second substrate.

Figure 15:
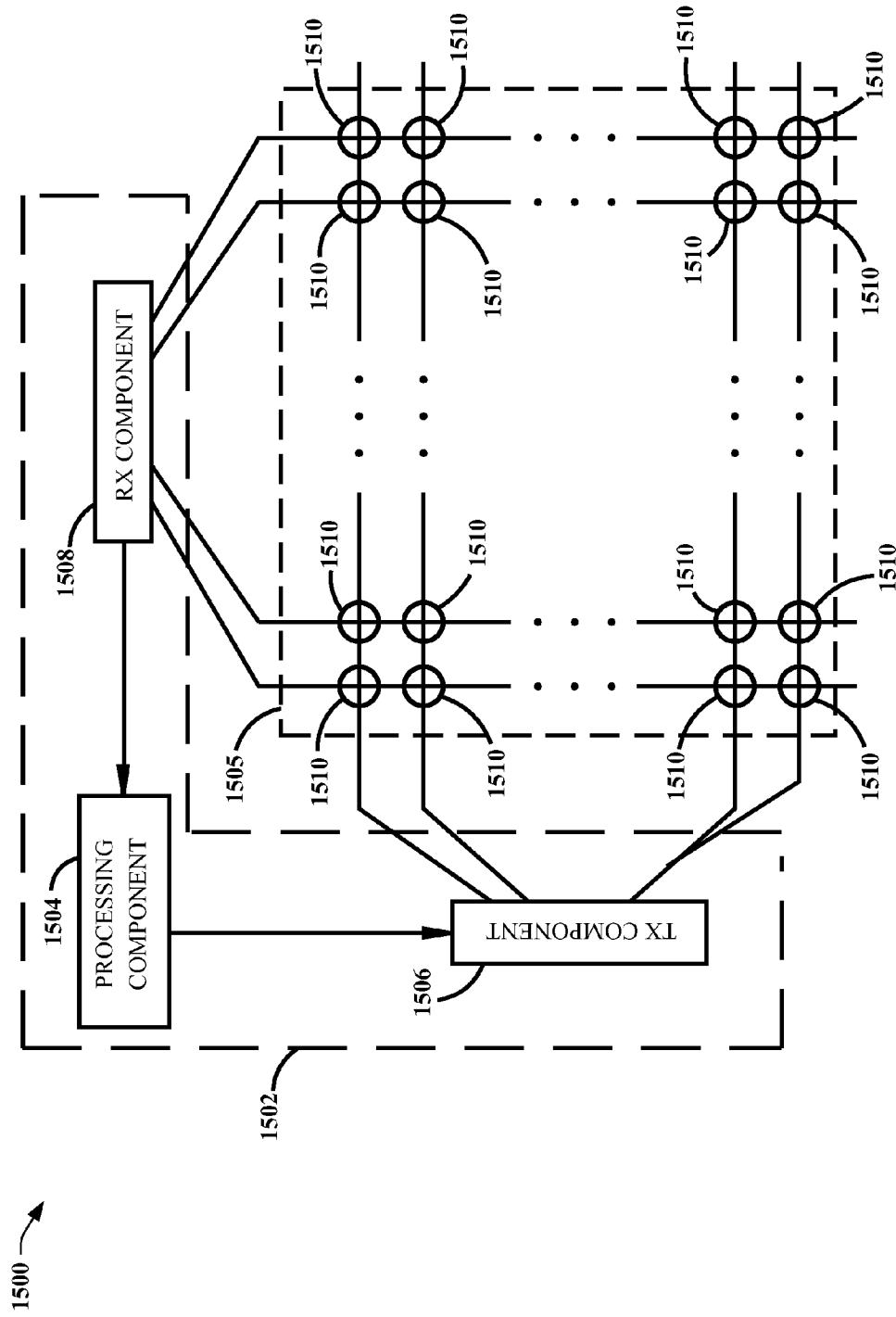
FIG. 15 illustrates a block diagram of a piezoelectric acoustic resonator based sensor, in accordance with various embodiments.

Referring now to FIG. 15, a block diagram of a piezoelectric acoustic resonator based sensor 1500 is illustrated, in accordance with various embodiments. Piezoelectric acoustic resonator based sensor 1500 includes control component 1502 and array of piezoelectric acoustic resonators 1505. Control component 1502, e.g., a system, an application specific integrated circuit (ASIC), etc. can include computing device(s), memory device(s), computing system(s), logic, etc. for generating stimuli, e.g., via TX component 1506, detecting a response to the stimuli, e.g., via RX component 1508, and determining, e.g., via processing component 1504 based on the stimuli and the response to the stimuli, a frequency response, e.g., a change in a resonant frequency, a change in a Q factor, etc. of a piezoelectric acoustic resonator (1510, 1605 (see below), 2005 (see below), etc.) of array of piezoelectric acoustic resonators 1505. In this regard, processing component 1504 can determine, based on the frequency response, whether the piezoelectric acoustic resonator has been touched, e.g., by a ridge of a finger, and further derive a fingerprint based on determining which piezoelectric acoustic resonator(s) 1510 of array of piezoelectric acoustic resonators 1505 have been touched.

Figure 16:
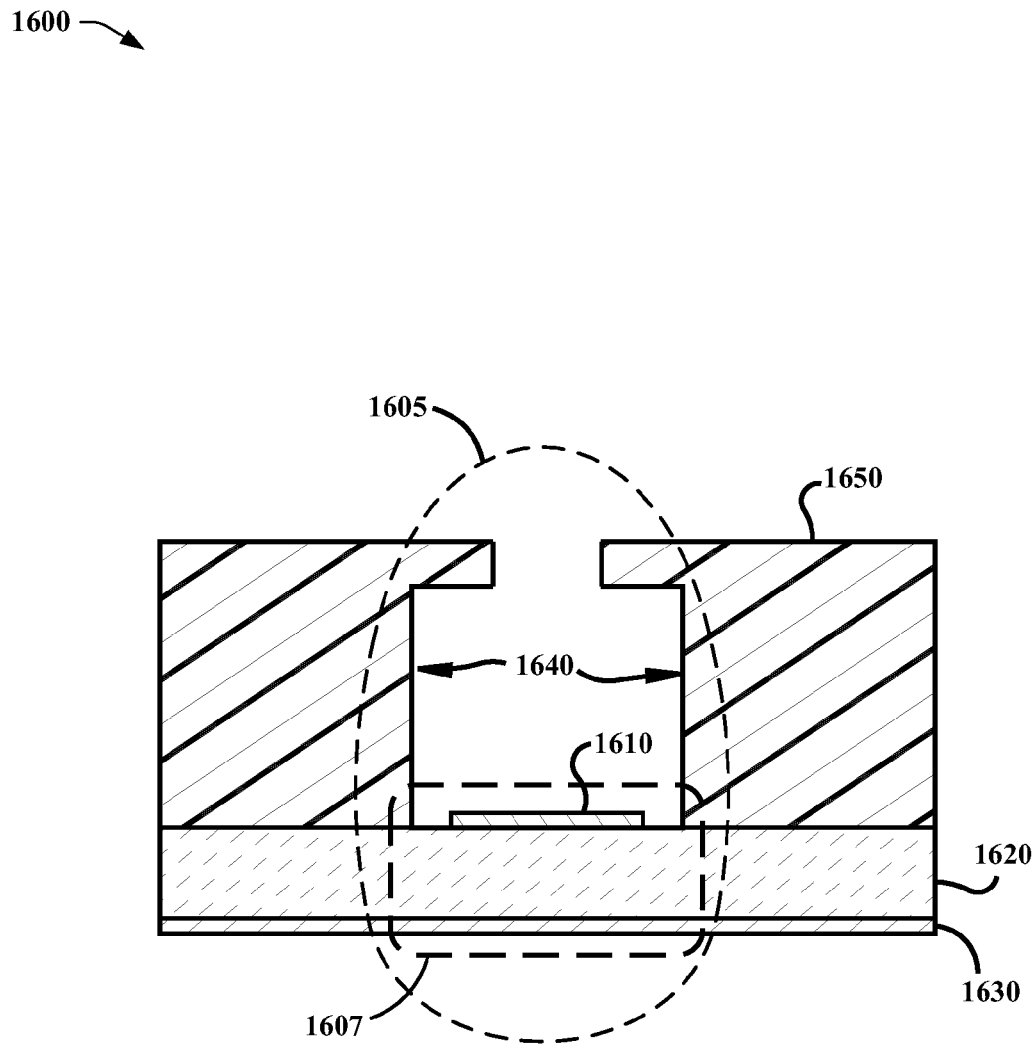
FIG. 16 illustrates a block diagram of a cross section of a microelectromechanical systems (MEMS) piezoelectric acoustic resonator, in accordance with various embodiments.

FIG. 16 illustrates a block diagram of a cross section of MEMS piezoelectric acoustic resonator 1605, in accordance with various embodiments. MEMS piezoelectric acoustic resonator 1605, e.g., a Helmholtz resonator, includes cavity 1640 that has been formed by, within, etc. substrate 1650, e.g., a silicon based material, etc. In the embodiment illustrated by FIG. 16, cavity 1640 includes an opening that is exposed to the environment, e.g., air. Further, a cross section of a first end, or top portion, of cavity 1640 is smaller than a cross section of a second end, or bottom portion, of cavity 1640, e.g., enabling cavity 1640 to experience a resonant frequency ($f_H$), or Helmholtz resonance, e.g., as defined by Equation (1) below:

$$f_H = \frac{v}{2\pi}\sqrt{\frac{A}{V_0 L_{eq}}}, \qquad (1)$$

where A is the cross-sectional area of the top portion, or "neck", of cavity 1640, $V_0$ is the static volume of cavity 1640, $L_{eq}$ is the equivalent length of the neck with end correction, and v is the speed of sound in a gas as given by Equation (2) below:

$$v = 331.3 + 0.606 \cdot \vartheta \qquad (2)$$

where is the ambient temperature in degree Celsius.

Figure 17:
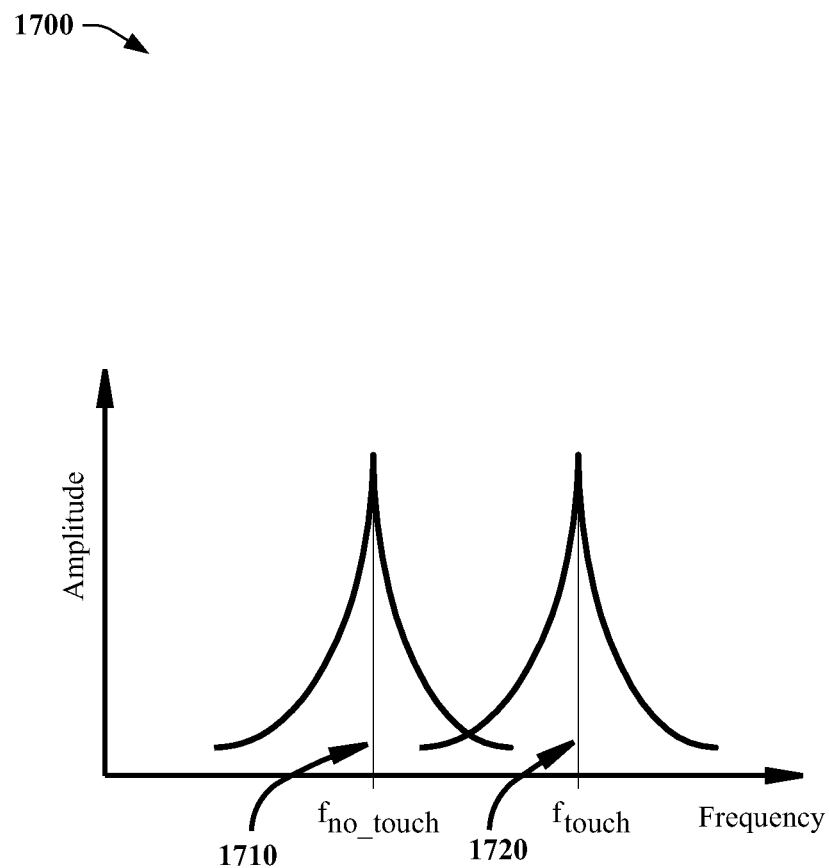
FIG. 17 illustrates a frequency response of a MEMS piezoelectric acoustic resonator, in accordance with various embodiments.

MEMS piezoelectric acoustic resonator 1605 includes piezoelectric transducer 1607, which includes top electrode 1610, piezoelectric material 1620, e.g., piezoelectric membrane, polyvinylidene fluoride (PVDF), etc. and bottom electrode 1630. In one embodiment, top electrode 1610 and bottom electrode 1630 can be manufactured from a conductive material, e.g., metal, and control component 1502 can generate and apply a stimulus, e.g., a pulse signal, a frequency sweep, an alternating current (AC) voltage, an AC current, etc. to piezoelectric transducer 1607 via top electrode 1610 and bottom electrode 1630. As illustrated by FIG. 17, control component 1502 can measure, e.g., utilizing a network analyzer, etc. based on the stimulus, e.g., based on a Fourier transform analysis, resonant frequency 1710, e.g., corresponding to a non-touch of piezoelectric acoustic resonator 1605, and resonant frequency 320, e.g., corresponding to a touch of piezoelectric acoustic resonator 1605. In this regard, in response to determining that the resonant frequency of piezoelectric acoustic resonator 1605 has increased, e.g., to resonant frequency 1720, control component 1502 can determine that MEMS piezoelectric acoustic resonator 1605 has been touched, e.g., by a ridge of a finger.

Figure 18:
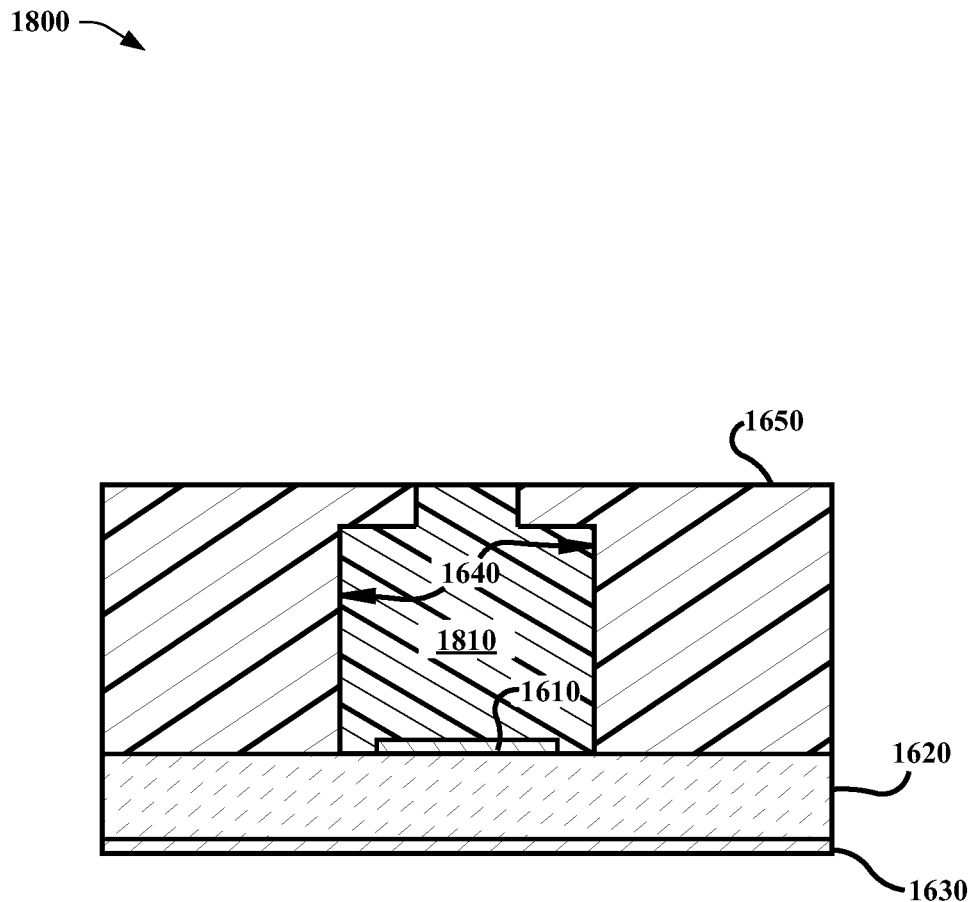
FIG. 18 illustrates a block diagram of a cross section a MEMS piezoelectric acoustic resonator including a material, in accordance with various embodiments.

FIG. 18 illustrates a block diagram of a cross section a MEMS piezoelectric acoustic resonator including material 1810, in accordance with various embodiments. As illustrated by FIG. 18, cavity 1640 can be filled with material 1810, e.g., rubber, gel, etc. that is associated with a first acoustic velocity that is different from a second acoustic velocity corresponding to substrate 1650. In this regard, a resonant frequency of MEMS piezoelectric acoustic resonator 1605 can be modified in a predetermined manner by selecting material 1810 of a predetermined acoustic velocity with respect to an acoustic velocity of substrate 1650. Further, including material 1810 in cavity 1640 can prevent debris, contaminants, etc. from entering cavity 1640 and subsequently introducing errors in measurements of the resonant frequency of MEMS piezoelectric acoustic resonator 1605.

Figure 19:
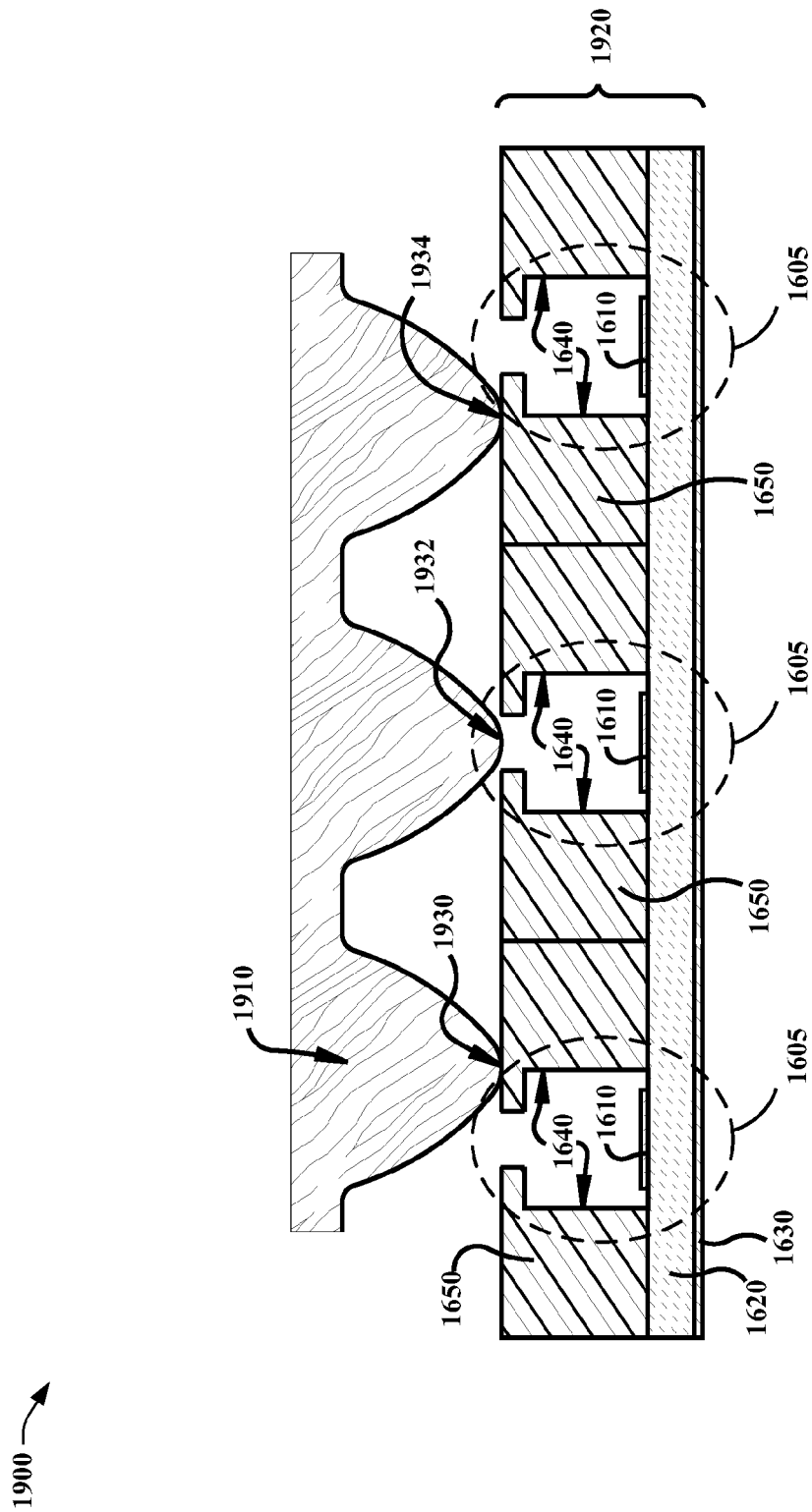
FIG. 19 illustrates a block diagram of a cross section of a portion of an array of MEMS piezoelectric acoustic resonators being contacted by a finger, in accordance with various embodiments.

FIG. 19 illustrates a block diagram of a cross section of a portion of an array (1920) of MEMS piezoelectric acoustic resonators (1605) being contacted by finger 1910, in accordance with various embodiments. Control component 1502 can determine that finger ridge 1932 has touched a MEMS piezoelectric acoustic resonator (1605) of the portion of the array based on a determination that a resonant frequency of the MEMS piezoelectric acoustic resonator has increased.

Further, control component 1502 can determine that other MEMS piezoelectric acoustic resonators (1605) of the portion of the array have not been touched, e.g., by finger ridge 1930 and finger ridge 1934, based on respective determinations that resonant frequencies of the other MEMS piezoelectric acoustic resonators has not changed. In this regard, control component 1502 can derive, based on such determinations, a fingerprint corresponding to finger 510.

Figure 20:
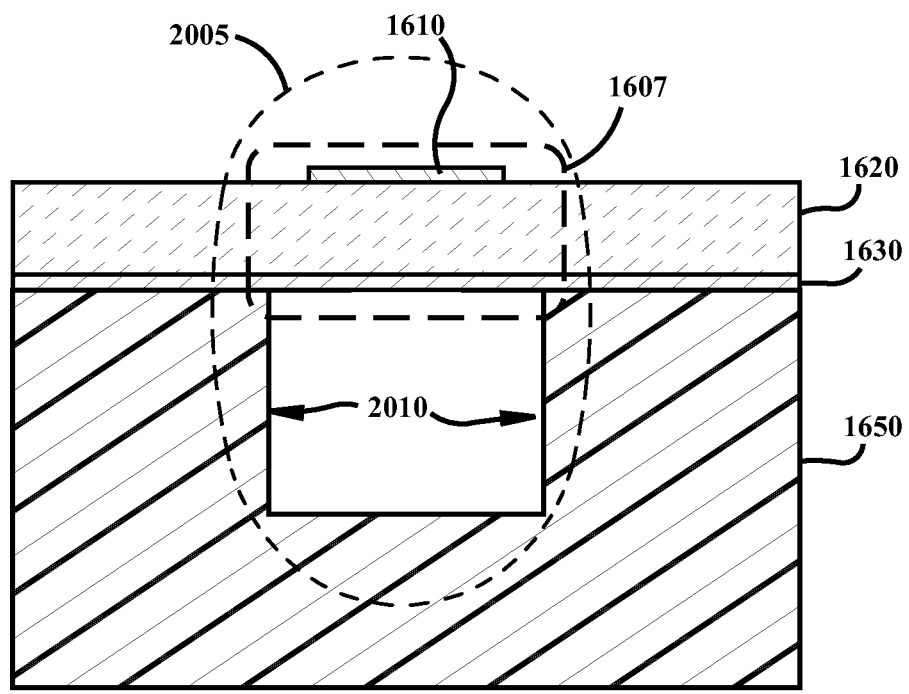
FIG. 20 illustrates a block diagram of a cross section of another MEMS piezoelectric acoustic resonator, in accordance with various embodiments.

Now referring to FIG. 20, a block diagram of a cross section of MEMS piezoelectric acoustic resonator 2005 is illustrated, in accordance with various embodiments. MEMS piezoelectric acoustic resonator 2005, e.g., a membrane resonator, includes cavity 2010 that has been formed by, within, etc. substrate 1650, e.g., a silicon based material, and has been enclosed by bottom electrode 1630 of piezoelectric transducer 1607. Control component 1502 can generate and apply a stimulus, e.g., a pulse signal, a frequency sweep, an alternating AC voltage, an AC current, etc. to piezoelectric transducer 1607 via top electrode 1610 and bottom electrode 1630.

Figure 21:
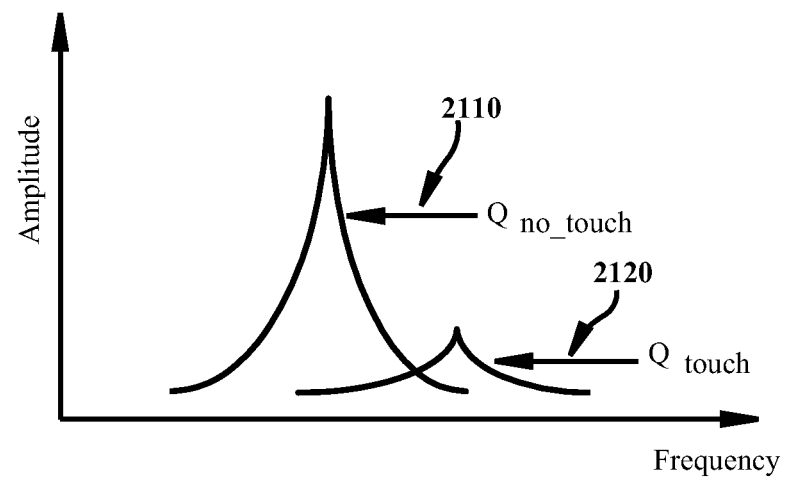
FIG. 21 illustrates a frequency response of another MEMS piezoelectric acoustic resonator, in accordance with various embodiments.

As illustrated by FIG. 21, control component 1502 can measure, based on the stimulus, Q factor 2110, e.g., corresponding to a non-touch of piezoelectric acoustic resonator 2005, and Q factor 2120, e.g., corresponding to a touch of piezoelectric acoustic resonator 2005. In this regard, in response to determining that the Q factor of piezoelectric acoustic resonator 2005 has decreased, e.g., to Q factor 2120, control component 1502 can determine that MEMS piezoelectric acoustic resonator 2005 has been touched, e.g., by a ridge of a finger.

Figure 22:
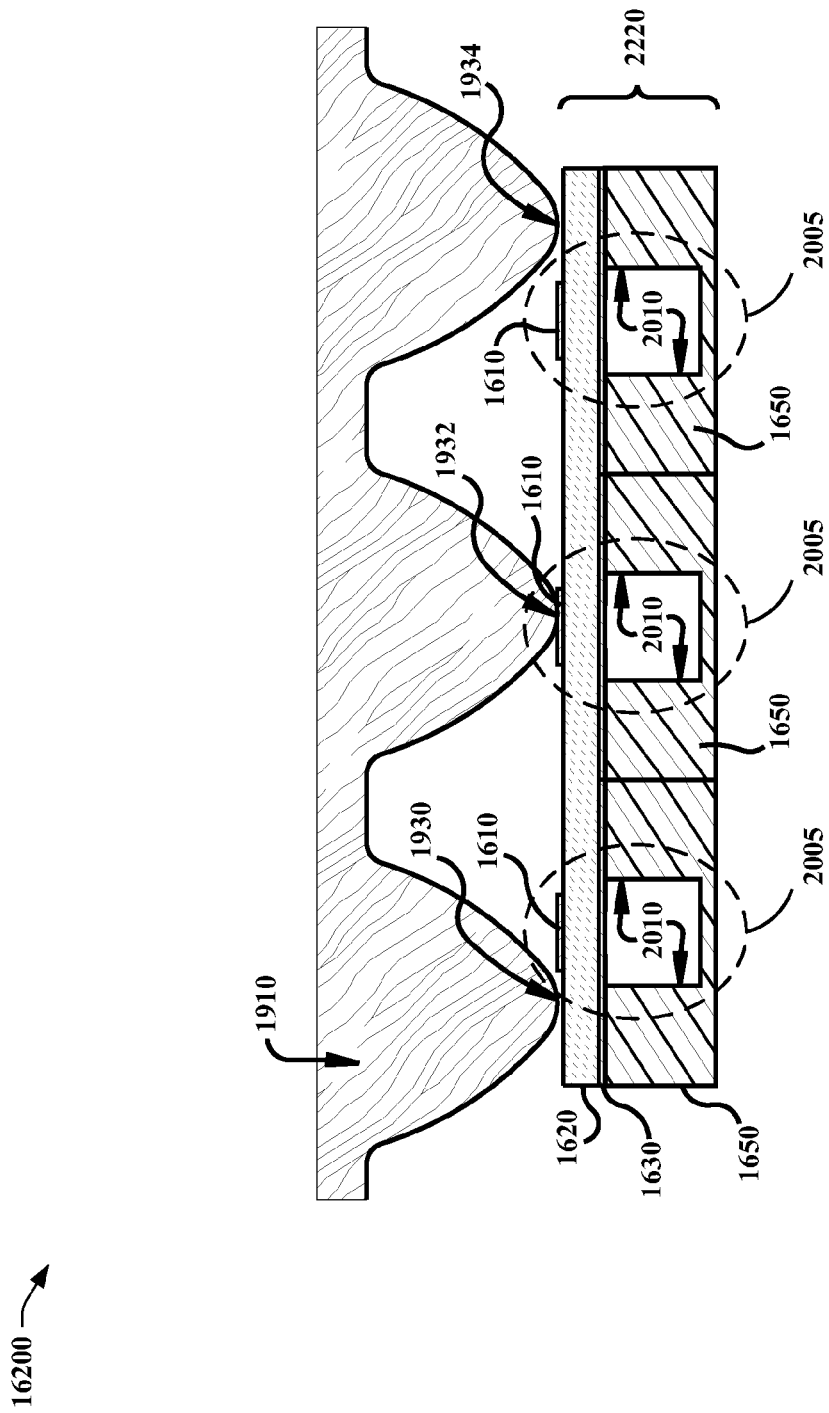
FIG. 22 illustrates a block diagram of a cross section of a portion of another array of MEMS piezoelectric acoustic resonators being contacted by a finger, in accordance with various embodiments.

FIG. 22 illustrates a block diagram of a cross section of a portion of an array (2220) of MEMS piezoelectric acoustic resonators (2005) being contacted by finger 1910, in accordance with various embodiments. Control component 1502 can determine that finger ridge 1932 has touched a MEMS piezoelectric acoustic resonator (2005) of the portion of the array based on a determination that a Q factor of the MEMS piezoelectric acoustic resonator has decreased. Further, control component 1502 can determine that other MEMS piezoelectric acoustic resonators (2005) of the portion of the array have not been touched, e.g., by finger ridge 1930 and finger ridge 1934, based on respective determinations that Q factors of the other MEMS piezoelectric acoustic resonators have not changed. In this regard, control component 1502 can derive, based on such determinations, a fingerprint corresponding to finger 1910.

Figure 23:
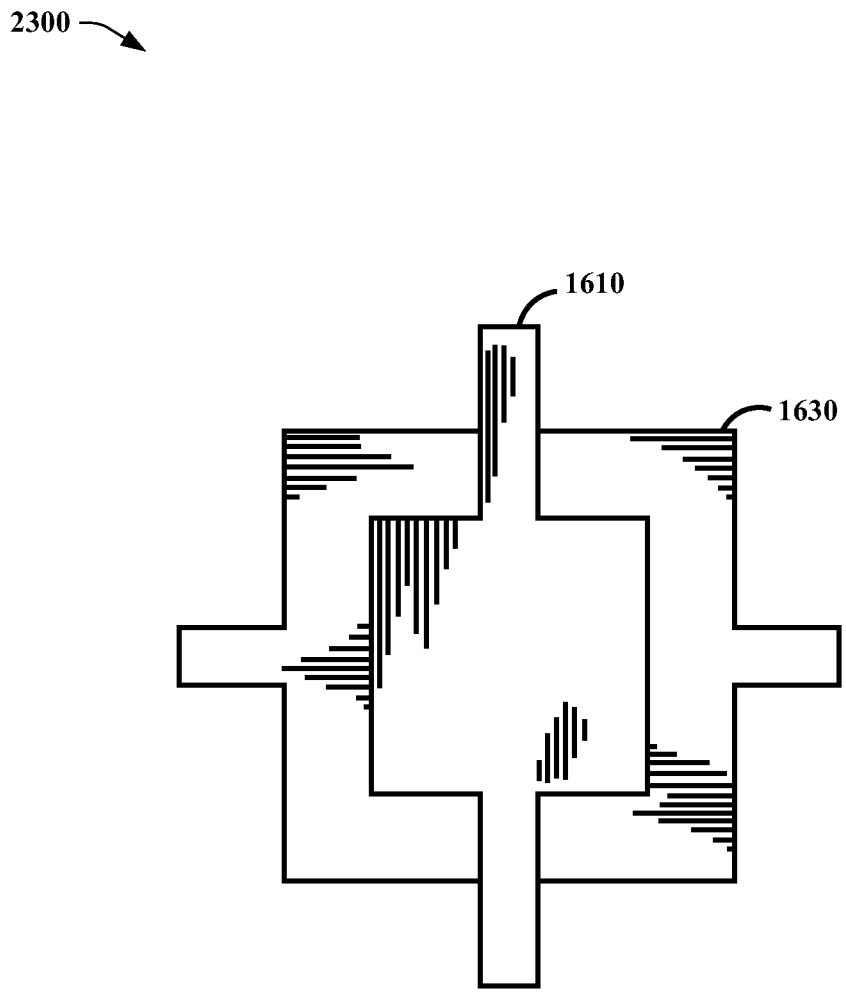
FIG. 23 illustrates a block diagram of a top view of electrodes of a piezoelectric acoustic resonator, in accordance with various embodiments.
Figure 24:
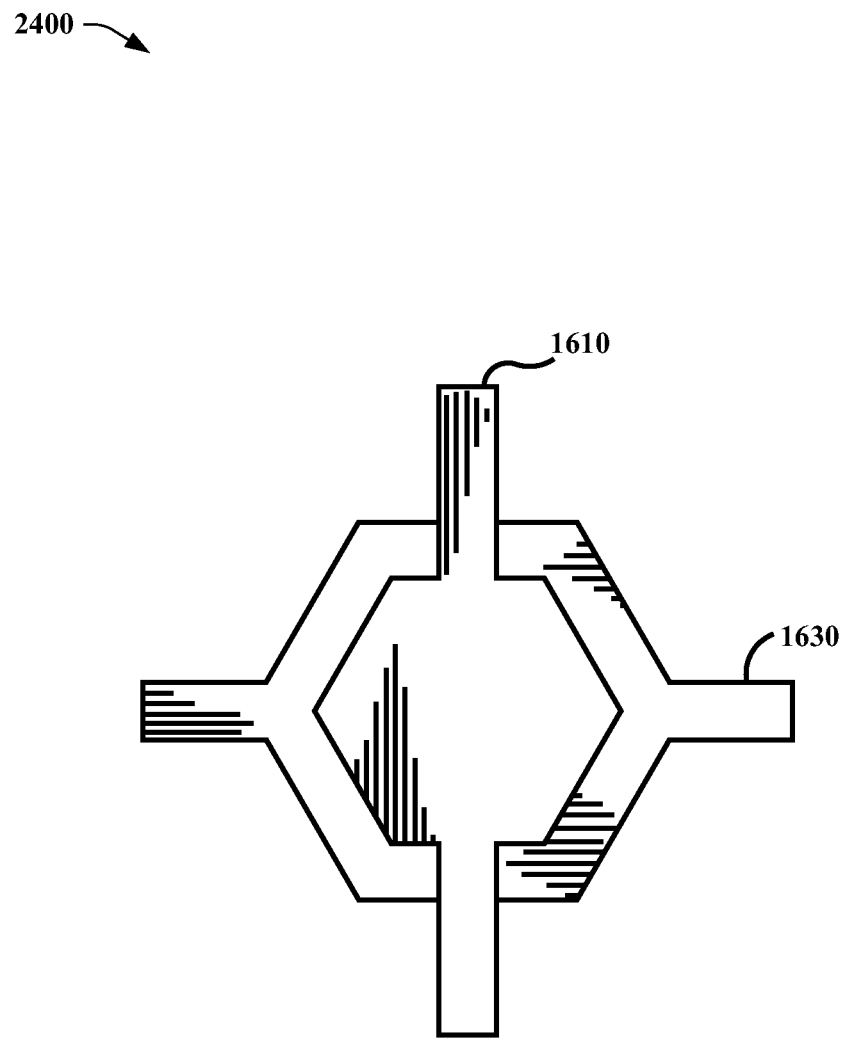
FIG. 24 illustrates a block diagram of a top view of other electrodes of a piezoelectric acoustic resonator, in accordance with various embodiments.
Figure 29:
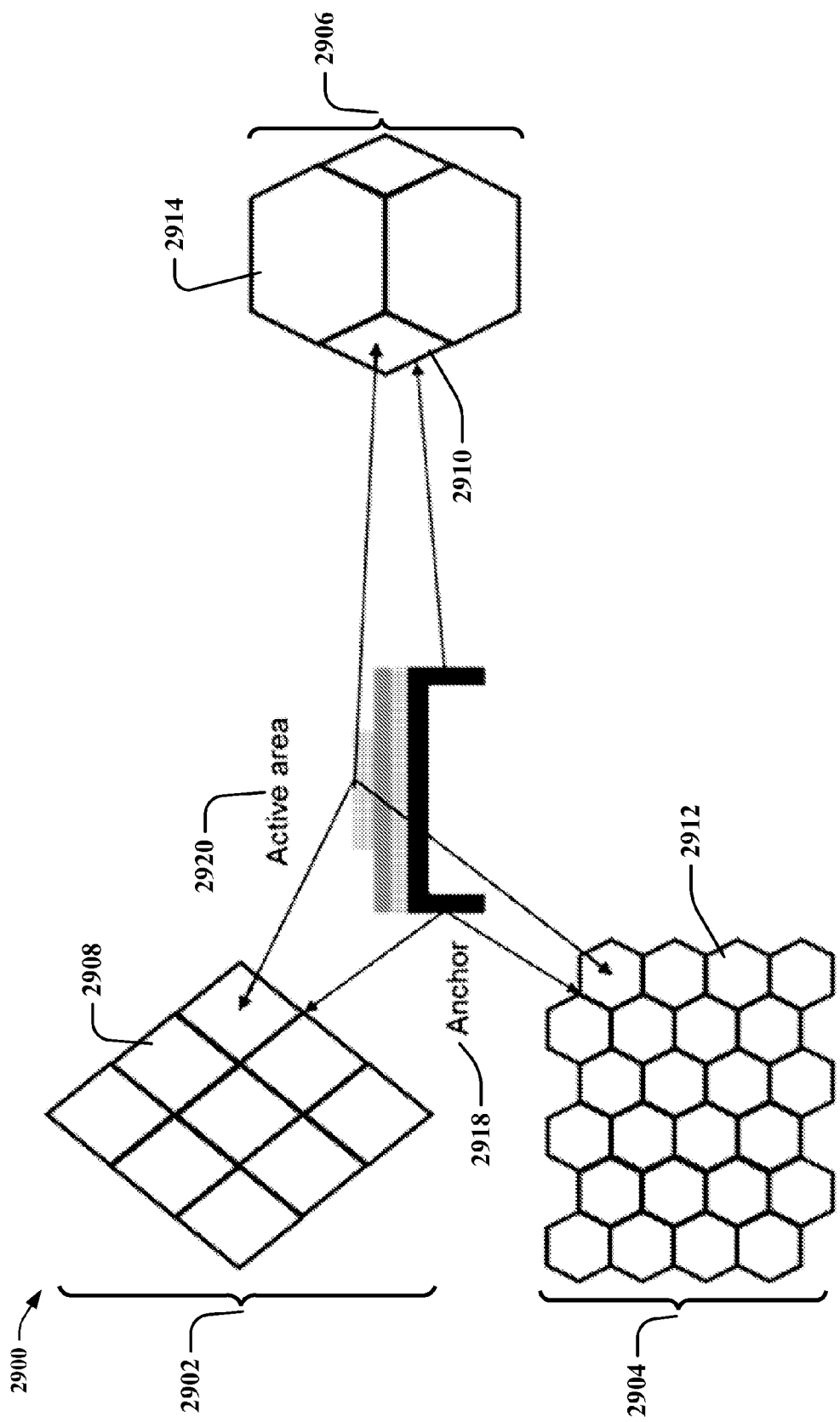
FIG. 29 depicts cross-sections of exemplary PMUT arrays having high fill factor, in accordance with further non-limiting embodiments.

In an embodiment illustrated by FIG. 23, top electrode 1610 can form a square shape that can be smaller, and located above, a square shape of bottom electrode 1630. In yet another embodiment illustrated by FIG. 24, top electrode 1610 can form a shape of a regular polygon that can be smaller, and located above, a regular polygon shape of bottom electrode 1630. In this regard, it should be appreciated by a person of ordinary skill in MEMS technologies having the benefit of the instant disclosure that embodiments of devices disclosed herein can comprise electrodes of various shapes. As a non-limiting example, FIG. 29 provides further shapes and configurations of exemplary PMUT arrays having high fill factor, in accordance with further non-limiting embodiments.

Figure 25:
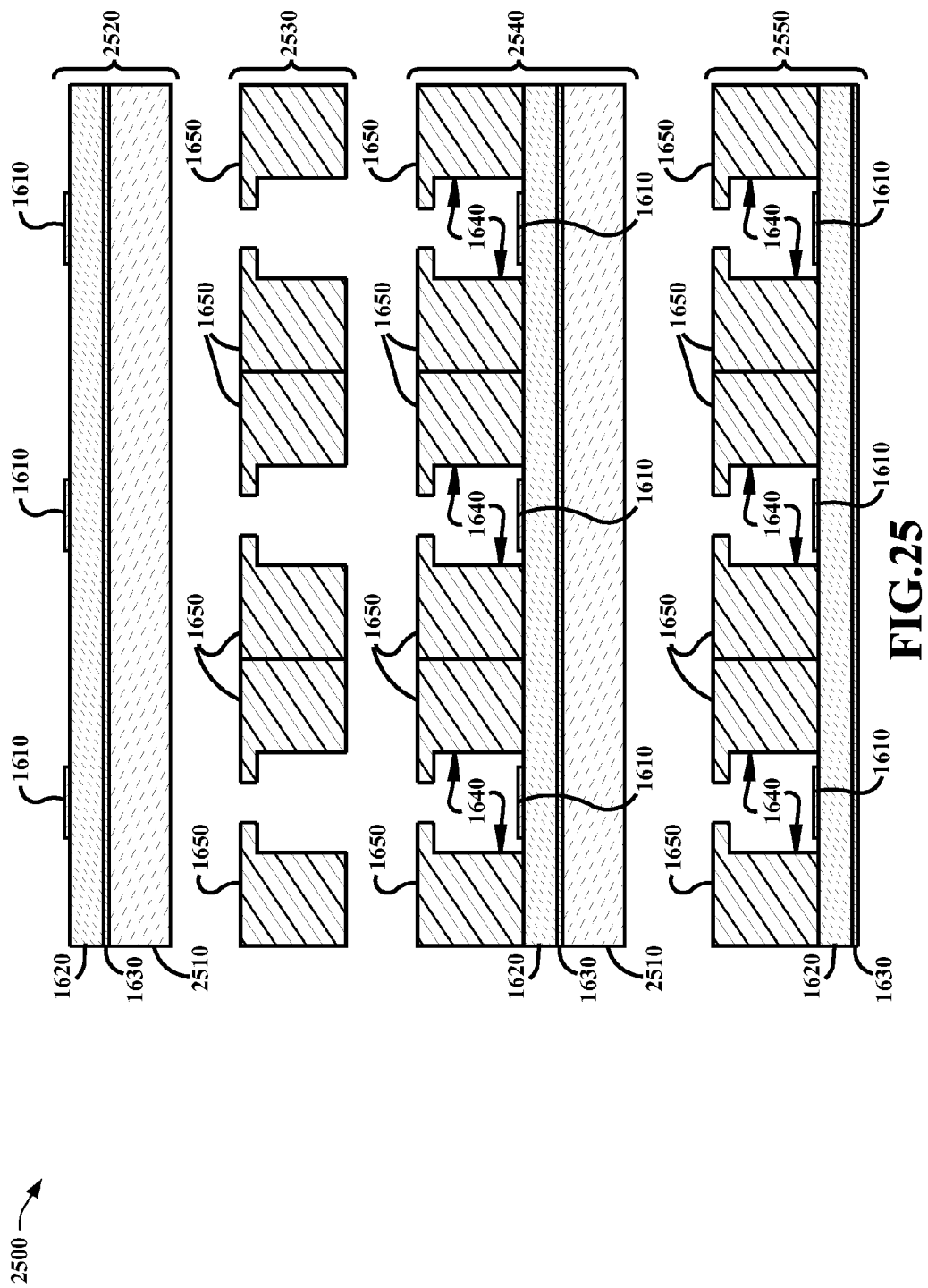
FIG. 25 illustrates a block diagram of a method for assembling a MEMS piezoelectric acoustic resonator, in accordance with various embodiments.

Referring now to FIG. 25, a block diagram (2500) representing a method for manufacturing, assembling, etc. a MEMS piezoelectric acoustic resonator, e.g., MEMS piezoelectric acoustic resonator 1605, is illustrated, in accordance with various embodiments. At 1120, an array of piezoelectric transducers (1607) can be formed on substrate 2510. For example, bottom electrodes (1630) can be formed on substrate 2510; dielectric material 1620 can be formed on, placed on, etc. the bottom electrodes; and top electrodes (1610) can be formed on, placed on, etc. dielectric material 1620.

At 2530, portions(s) of an array of cavities (1640) can be formed on substrate 1650. At 2540, the portion(s) of the array of cavities can be placed on, attached to, etc. the array of piezoelectric transducers (1607). In another embodiment (not shown), one or more cavities of the array of cavities can be filled with a material having a first acoustic velocity that is different from a second acoustic velocity of substrate 1650. At 2550, substrate 2510 can be removed from the bottom electrodes.

Figure 26:
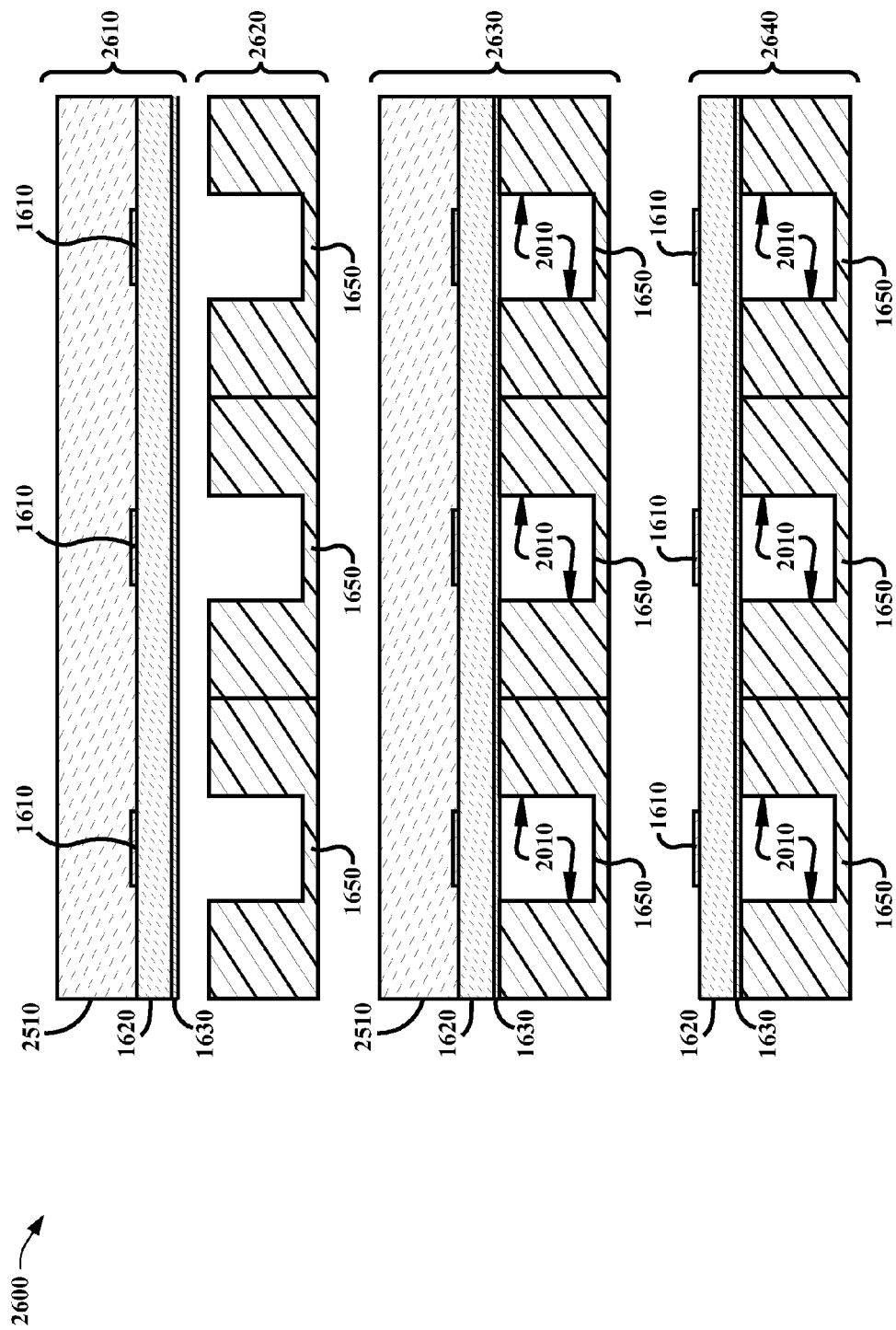
FIG. 26 illustrates a block diagram of a method for assembling another MEMS piezoelectric acoustic resonator, in accordance with various embodiments.

FIG. 26 illustrates a block diagram (2600) representing another method for manufacturing, assembling, etc. a MEMS piezoelectric acoustic resonator, e.g., MEMS piezoelectric acoustic resonator 2005, is illustrated, in accordance with various embodiments. At 2610, an array of piezoelectric transducers (1607) can be formed on substrate 2610. For example, top electrodes can be formed on substrate 2610; dielectric material 1620 can be formed on, placed on, etc. the top electrodes and substrate 2610; and bottom electrodes (2630) can be formed on, placed on, etc. dielectric material 1620.

At 2620, portions(s) of an array of cavities (2010) can be formed on substrate 1650. At 2630, the portion(s) of the array of cavities can be placed on, attached to, etc. the array of piezoelectric transducers (1607). At 2640, substrate 2610 can be removed from dielectric material 1620 and the top electrodes.

The order in which some or all of the manufacturing, assembling, etc. steps described above with respect to block diagrams 2500 and 2600 should not be deemed limiting. Rather, it should be understood by a person of ordinary skill in MEMS technologies having the benefit of the instant disclosure that some of the steps can be executed in a variety of orders not illustrated.

In addition to the foregoing, the subject application further describes PMUTs for fingerprint sensing. As described above, MUT devices, as an alternative method for fingerprint detection typically require MUT devices to be manufactured in the resolution of at least 300 dpi or higher e.g., approximately 85 μm pixel size. In addition, for mobile applications, optical method can be too bulky or expensive; thermal and capacitive sensing swipe-based method are not the favored due to user experience. As area-based fingerprint sensor is convenient in usage, it is suitable for adoption in mobile devices and can provide a sufficient level of security. Moreover, ultrasonic fingerprint detection can overcome deficiencies associated with skin condition and/or sensor contamination that afflict the accuracy of fingerprint detection devices employing CMUT linear arrays. For example, existing fingerprint sensors are mostly based on capacitive sensing. Their detection ability is readily compromised by excessively dry or wet fingerprints and/or contamination from sweat or oil. Ultrasonic detection does not rely on electrical property, instead, it relies on physical contact and acoustic impedance difference and is proven to be able to detect ridges and valleys and also sweat pores which are not so easily detectable with capacitive sensing.

Various embodiments disclosed herein provide integrated PMUTs on IC for fingerprint sensing. Additionally, various embodiments can provide an efficient way of creating electrical coupling and mechanical anchoring of ultrasonic transducer pMUT directly on CMOS for reduced parasitics and fully utilize the routing capability on CMOS metal layers.

In addition, in order to achieve a compact PMUT array with good resolution, it is desirable to achieve a high fill factor for a PMUT array that can provide a desired output pressure for the ultrasound transducer array. Various embodiments described herein can thus increase the increase the signal to noise ratio (SNR) of PMUT arrays during detection and the array gain, which is the ratio of the array's output pressure to that of a single PMUT device. However, increasing fill factor can suppress mechanical coupling between adjacent PMUT pixels. Thus, to achieve proper mechanical coupling or anchor while achieving a high fill factor, it is desired to minimize the anchor occupation ratio compared to the PMUT "active" area. Thus, various embodiments disclosed herein provide integrated PMUTs on IC for fingerprint sensing where the PMUT structures and the array of PMUT structures are configured in a rhombus configuration, a hexagonal configuration, and/or a combination of rhombus configuration and hexagonal configuration.

Figure 27:
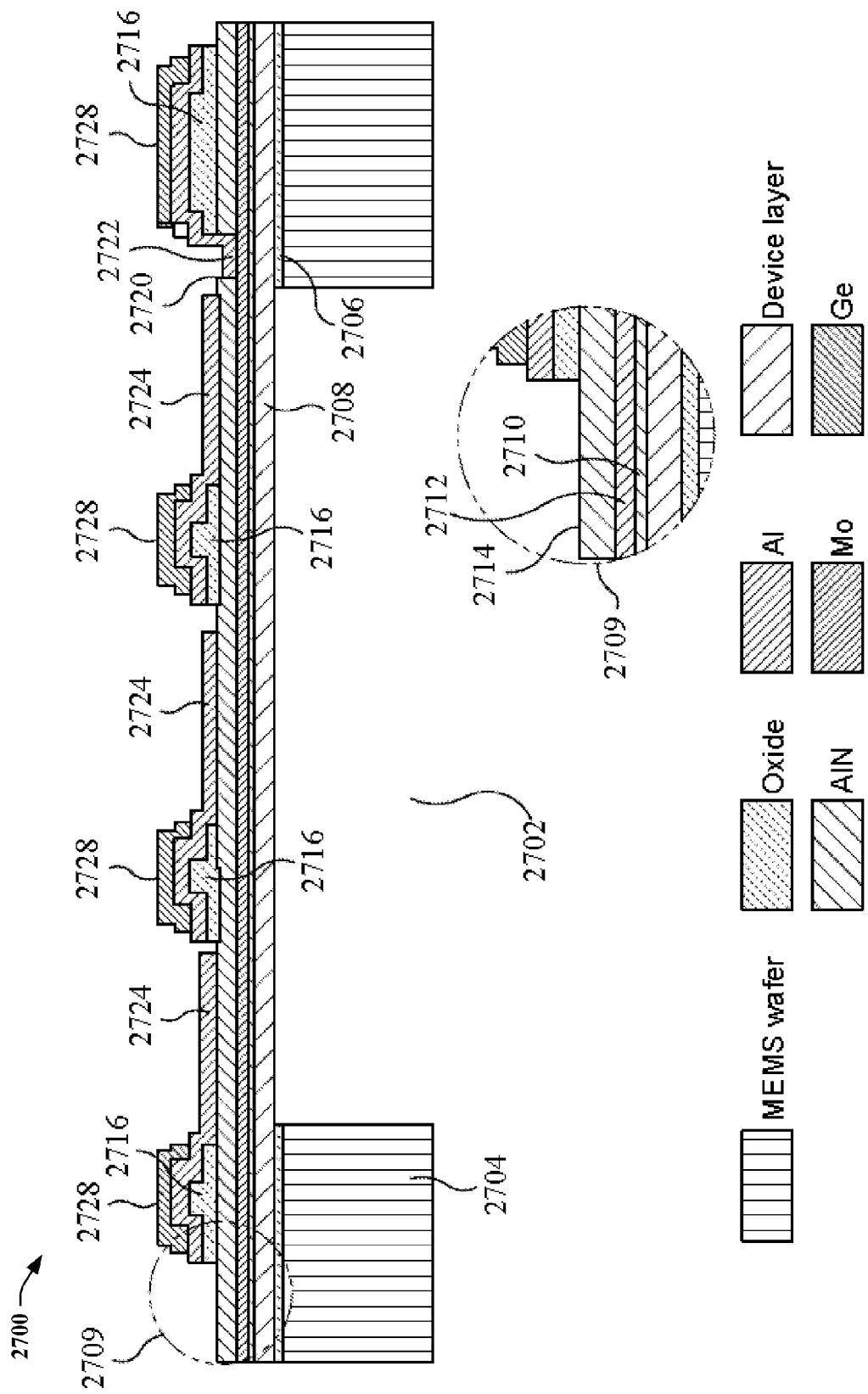
FIG. 27 depicts a cross-section of an exemplary PMUT for fingerprint sensing, in accordance with various embodiments.

For example, FIG. 27 depicts a cross-section of an exemplary PMUT 2700 for fingerprint sensing, in accordance with various embodiments. As a non-limiting example, exemplary PMUT 2700 can comprise an engineered silicon-on-insulator (ESOI) wafer that can comprise a SOI wafer with one or more cavities beneath the silicon device layer or substrate. For instance, exemplary PMUT 2700 can comprise cavity 2702 in PMUT wafer/layer/substrate 2704, to which a silicon dioxide layer/substrate 2706 can be deposited on PMUT wafer/layer/substrate 2704 thereby overlaying PMUT wafer/layer/substrate 2704. Disposed and/or deposited over silicon dioxide layer/substrate 2706 and/or fusion bonded to the silicon dioxide layer/substrate 2706 can be a substrate/layer formed of silicon 2708 or silicon structural substrate/layer 2708. As described above regarding FIGS. 9A-9K, for example, the PMUT wafer/layer/substrate 2704 inclusive of one or more formed cavity 902 and silicon dioxide layer/substrate 2706 can be referred to as an engineered substrate, and for purposes of this disclosure can be referred to as MEMS handle layer.

FIG. 27 further depicts, in inset 2709, exemplary PMUT 2700 further comprising successively deposited exemplary aluminum nitride (AlN) seed layer 2710, molybdenum (Mo) layer 2712, and AlN stacking layer 2714, upon which silicon dioxide standoffs 2716 can be formed to prepare a movable space of exemplary PMUT 2700. The additional deposited or disposed layers comprising the aluminum nitride seed layer 2710, molybdenum layer 2712, aluminum nitride stacking layer 2714 and silicon dioxide standoffs 2716 over substrate/layer formed of silicon 2708 can be referred to as PMUT device layer/wafer/substrate and/or piezoelectric layer/wafer/substrate.

Figure 28:
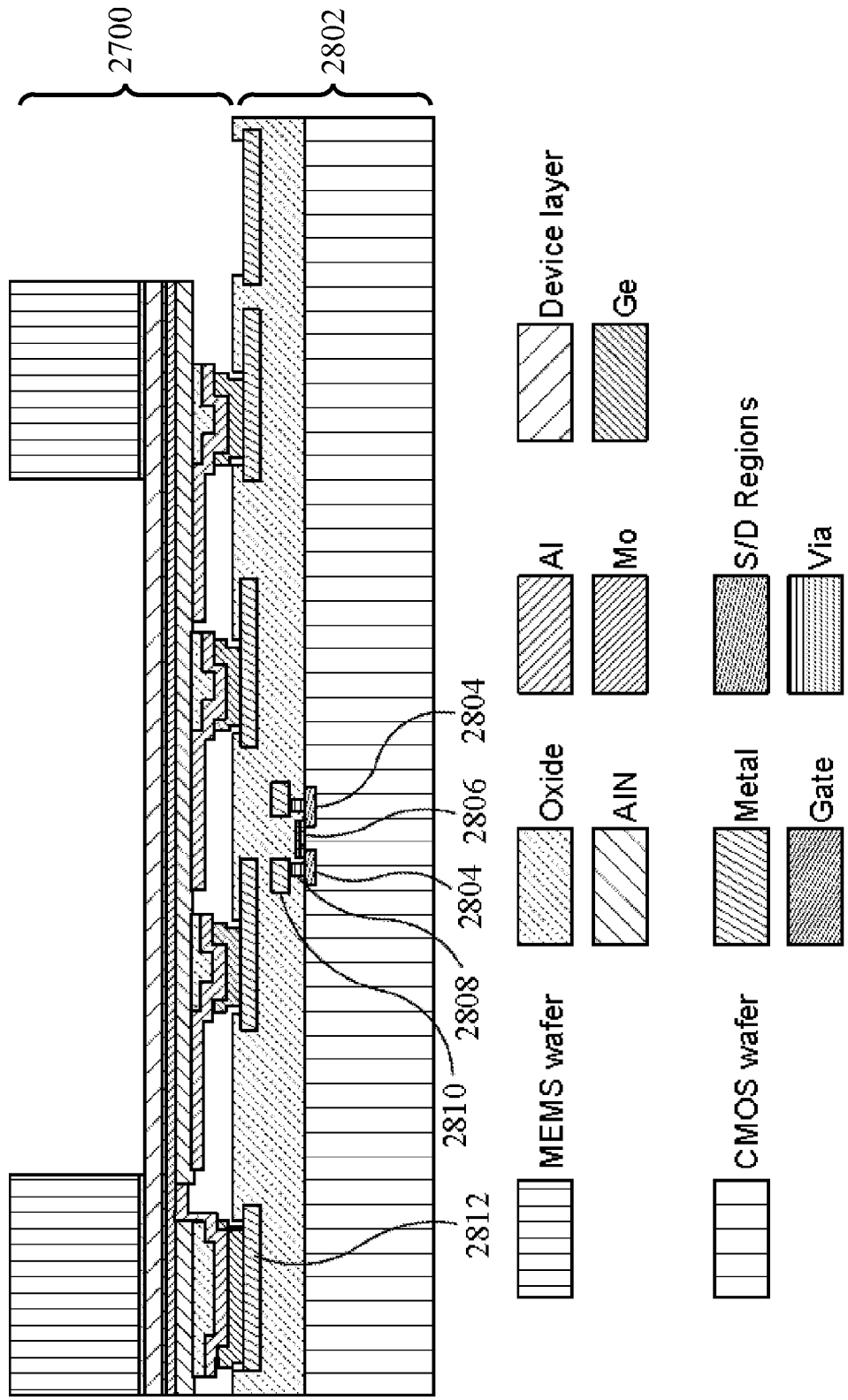
FIG. 28 depicts a cross-section of exemplary PMUT for fingerprint sensing on IC comprising exemplary PMUT bonded to an exemplary complementary metal oxide semiconductor (CMOS) wafer, in accordance with further non-limiting embodiments.

Substrate/layer formed of silicon 2708 can be the silicon structural layer of the PMUT device layer to which the MEMS handle layer (e.g., PMUT wafer/layer/substrate 2704 inclusive of cavities 2702 and silicon dioxide layer/substrate 2706) can have been fusion bonded to the PMUT device layer/wafer/substrate (e.g., silicon structural substrate/layer 2708, aluminum nitride seed layer 2710, molybdenum layer 2712, aluminum nitride stacking layer 2714, and standoffs 2716). It should be noted that, if fusion bonded to the PMUT device layer, the fusion bonding of the MEMS handle layer to the PMUT device layer can comprise the MEMS handle layer being oxidized and the silicon structural layer/substrate 2708 of the PMUT device layer being ground and polished to a target or defined thickness prior to deposition of the aluminum nitride seed layer 2710, molybdenum layer 2712, aluminum nitride stacking layer 2714, and standoffs 2716 formed of silicon dioxide. Standoffs 2716 are typically formed on the PMUT device layer to provide separation between the MEMS structure and a CMOS wafer/layer/substrate, for example, as depicted in FIG. 28.

FIG. 27 further depicts exemplary PMUT 2700 further comprising structures defined for one or more bottom electrodes 2720 that can be carved out by first disposing or depositing a silicon dioxide hard mask (not shown) over the aluminum nitride stacking layer 2714 and standoffs 2716 and thereafter etching through silicon dioxide hard mask (not shown) to define the structure and carve out one or more bottom electrodes 2720, for example, as described above regarding FIGS. 9A-9K, for example. As can be understood, the etching process can etch through layers/substrates respectively formed of silicon dioxide hard mask (not shown), aluminum nitride stacking layer 2714, and molybdenum layer 2712.

One or more bottom electrode 2720 contacts 2722 can be created, as depicted in FIG. 27. In addition, an opening etch on silicon dioxide hard mask (not shown) can be performed to define aluminum top electrode 2724 contacts, thus forming electrical contacts to the molybdenum layer 2712 and aluminum nitride stacking layer 2714. The defined structure and carved out one or more bottom electrodes 2720, the bottom electrode 2720 contact 2722, and the aluminum top electrode 2724 contacts, as depicted in FIG. 27, can be undertaken by patterning the aluminum or other suitable material through a silicon dioxide hard mark (not shown).

In addition, aluminum and titanium layers (not shown) can be deposited for the purposes of top electrode material deposition and then germanium layers 2728 can be deposited over the aluminum and titanium (not shown) so that pads and electrodes can be patterned, as described above regarding FIGS. 9A-9K, for example, as well as forming a barrier layer and eutectic bonding layer.

FIG. 28 depicts a cross-section 2800 of exemplary PMUT 2700 for fingerprint sensing on IC comprising exemplary PMUT 2700 bonded to an exemplary CMOS wafer 2802, in accordance with further non-limiting embodiments. For example, an exemplary CMOS wafer 2802 can comprise exemplary source/drain regions 2804, gate 2806, one or more vias 2808, and one or more metal layers including a first metal layer 2810 and an exemplary top metal layer 2812. In a non-limiting aspect, an exemplary top metal layer 2812 of exemplary CMOS wafer 2802 can comprise aluminum.

Thus, as described above regarding FIG. 9J, for example, exemplary CMOS wafer 2802 and exemplary PMUT 2700 can be bonded using an aluminum-germanium eutectic bond between exemplary top metal layer 2812 of exemplary CMOS wafer 2802 and germanium layers 2728 on standoffs 2716 of exemplary PMUT 2700. The Aluminum-Germanium eutectic bond can create a hermetic seal around desired MEMS structures and/or CMOS wafer 2802 circuits and form a bonded wafer comprising exemplary CMOS wafer 2802 and exemplary PMUT 2700. As can be understood the single bonding process using an Aluminum-Germanium eutectic bond provides hermetic sealing, mechanical anchoring, and electrical connection in one step. The eutectically bonded wafer comprising exemplary CMOS wafer 2802 and exemplary PMUT 2700 can then be thinned, for instance, on the PMUT wafer/layer/substrate 2704 side, to a defined or desired thickness. In addition, a port or cavity (e.g., cavity 2702 or other) can be formed on a polished side of the PMUT wafer/layer/substrate 2704 to create access to the surrounding environment, as describe above regarding FIG. 9K, for example. For instance, an etch can be performed on the top side of the bonded wafer to form an acoustic port or cavity for sound propagation.

As described above, achieving high fill factor for a PMUT array can provide a desired output pressure for the ultrasound transducer array, increasing the PMUT array gain. However, increasing fill factor can suppress mechanical coupling between adjacent PMUT pixels. Thus, to achieve proper mechanical coupling or anchor while achieving a high fill factor is desired to minimize the anchor occupation ratio compared to the PMUT "active" area. Thus, various embodiments disclosed herein provide integrated PMUTs on IC for fingerprint sensing where the PMUT structures and the array of PMUT structures are configured in a rhombus configuration, a hexagonal configuration, and/or a combination of rhombus configuration and hexagonal configuration.

Accordingly, FIG. 29 depicts cross-sections of exemplary PMUT arrays (2902, 2904, 2906) having high fill factor, in accordance with further non-limiting embodiments. As non-limiting examples, FIG. 29 depicts exemplary PMUT arrays (2902, 2904, 2906) comprising PMUT structures in the exemplary PMUT arrays (2902, 2904, 2906) of PMUT structures that are configured in a rhombus configuration (2908, 2910) or a hexagonal configuration (2912, 2914). As depicted in FIG. 29, the exemplary PMUT arrays (2902) of PMUT structures can comprise PMUT structures that are configured in a rhombus configuration (2908), the exemplary PMUT arrays (2904) of PMUT structures can comprise PMUT structures that are configured in a hexagonal configuration (2912), or the exemplary PMUT arrays (2906) of PMUT structures can comprise PMUT structures that are configured in a combination of rhombus configuration (2910) and hexagonal configuration (2914) arranged as a unit cell.

Note that, according to a non-limiting aspect, edges of the PMUT structures between neighboring PMUT structures of the exemplary PMUT arrays (2902, 2904, 2906) can correspond to mechanical anchor 2918 points for the PMUT structure, for example, such as provided by aluminum-germanium eutectic bond between exemplary top metal layer 2812 of exemplary CMOS wafer 2802 and germanium layers 2728 on standoffs 2716 of exemplary PMUT 2700, as described above, regarding FIG. 27, for example. As described above, to achieve proper mechanical coupling or mechanical anchor 2918 while achieving a high fill factor, it is desired to minimize the anchor occupation ratio compared to the PMUT structure active area 2920. Exemplary PMUT arrays (2902, 2904, 2906), as described herein, can provide high fill factor, thus increasing the array gain of exemplary PMUT arrays (2902, 2904, 2906).

In another non-limiting aspect, exemplary PMUT arrays (2902) of PMUT structures comprising PMUT structures configured in a hexagonal configuration (2912) can be formed in quadrilateral shape having angles of about 60 degrees. In a further non-limiting aspect, exemplary PMUT arrays (2904) of PMUT structures comprising PMUT structures configured in a rhombus configuration (2908) can be formed in quadrilateral shape having angles of about 60 degrees and about 120 degrees.

Figure 30:
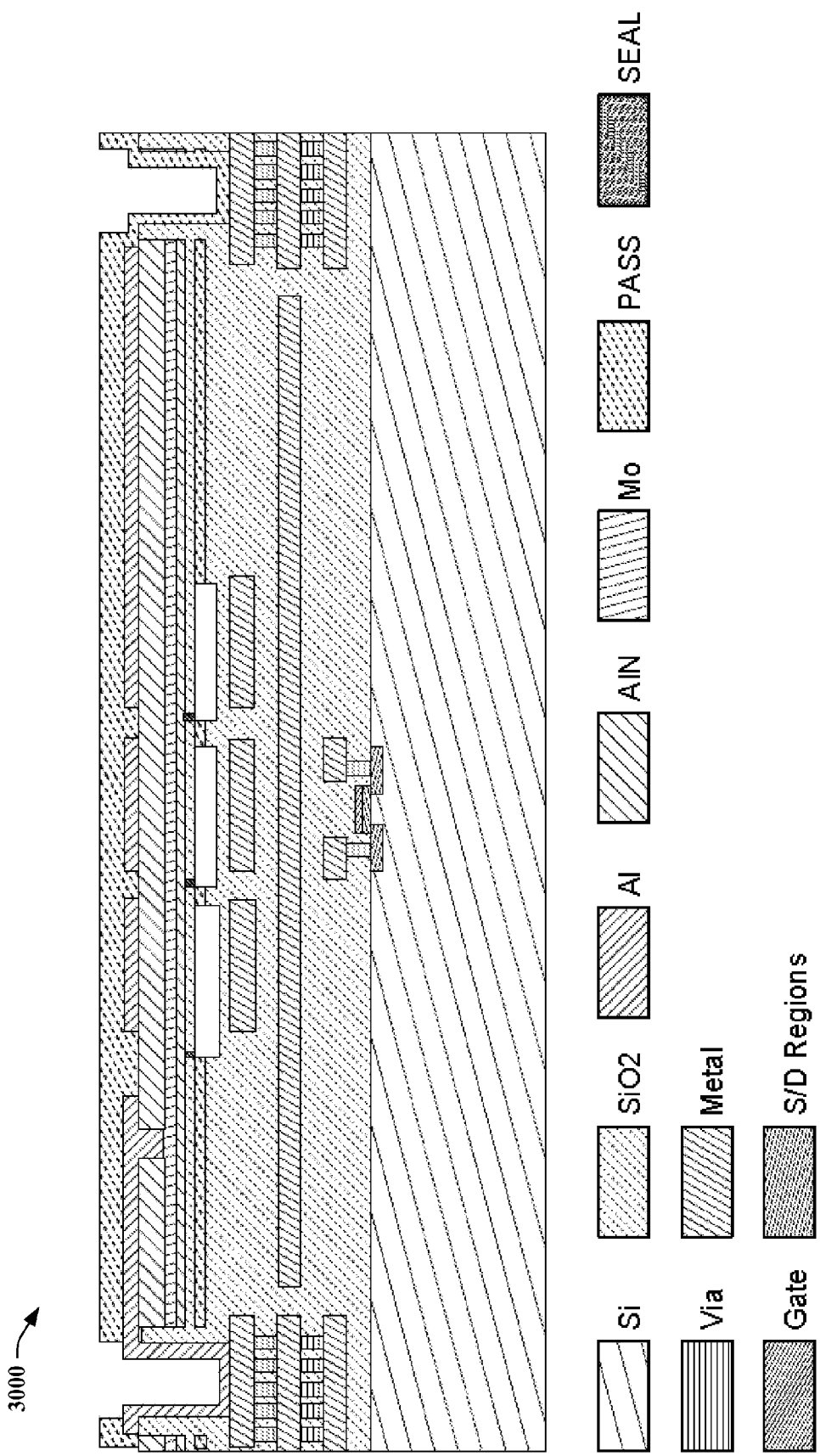
FIG. 30 depicts a cross-section of exemplary PMUT for fingerprint sensing on IC comprising exemplary PMUT integrated on an exemplary CMOS wafer, in accordance with further non-limiting embodiments.

While the foregoing can provide exemplary PMUTs on IC for fingerprint sensing comprising compact PMUT arrays with good resolution, silicon fabrication cost of exemplary PMUT 2700 bonded to an exemplary CMOS wafer 2802, as described above regarding FIG. 28, can be improved, for example, by integrating exemplary PMUTs on IC (e.g., an exemplary CMOS wafer) for fingerprint sensing. Accordingly, FIG. 30 depicts a cross-section of exemplary PMUT for fingerprint sensing on IC comprising exemplary PMUT 3000 integrated on an exemplary CMOS wafer, in accordance with further non-limiting embodiments. As a non-limiting example, an exemplary PMUT 3000 can be integrated on an exemplary CMOS wafer, as described below regarding FIGS. 31-45.

Figure 31:
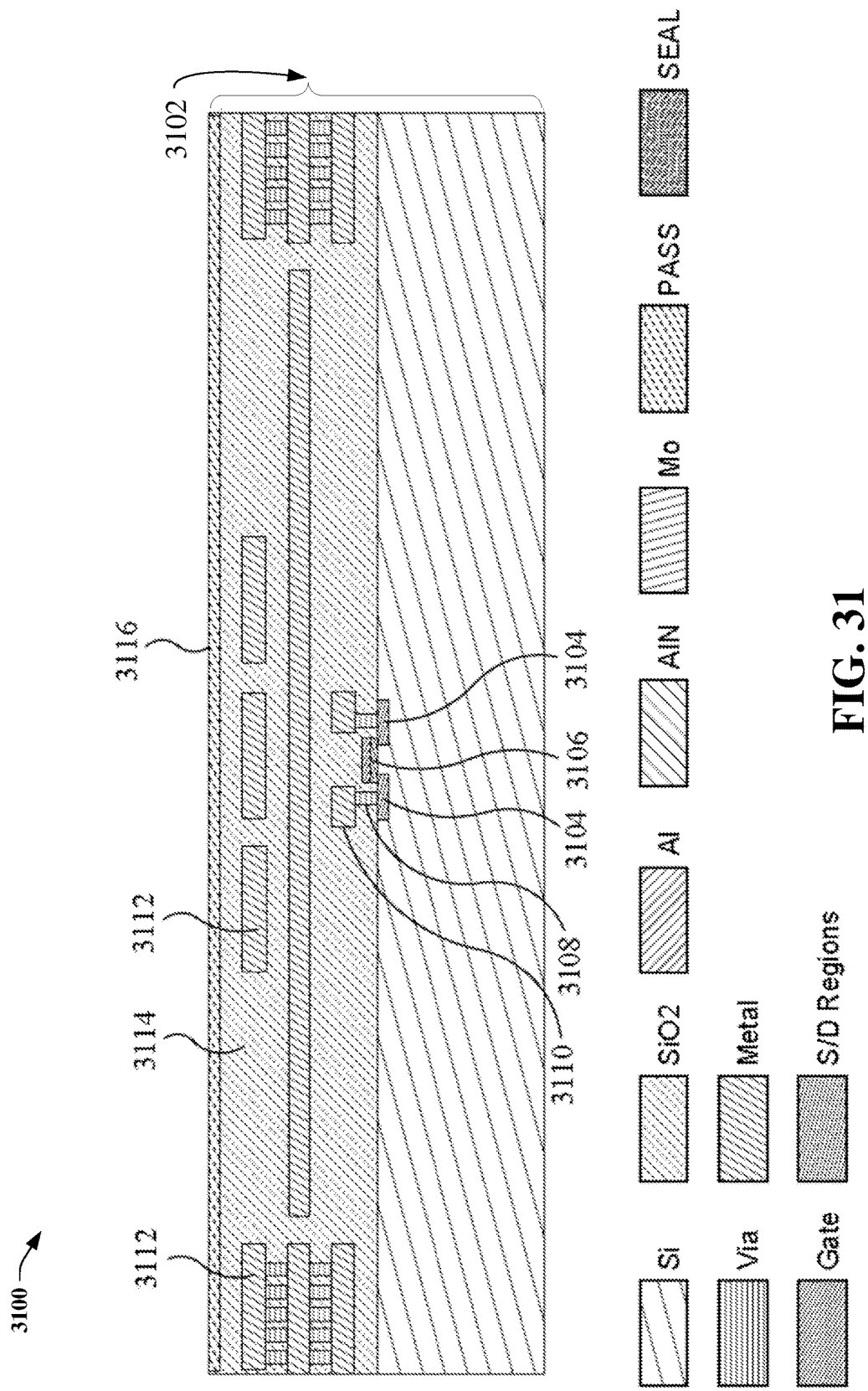
FIG. 31 depicts a cross-section of an exemplary CMOS wafer suitable for incorporation of aspects of the subject disclosure directed to fabrication of exemplary PMUT and PMUT arrays for fingerprint sensing on IC comprising exemplary one or more exemplary PMUTs integrated on exemplary CMOS wafer, in accordance with further non-limiting embodiments.

For example, FIG. 31 depicts a cross-section 3100 of an exemplary CMOS wafer 3102 suitable for incorporation of aspects of the subject disclosure directed to fabrication of exemplary PMUT and PMUT arrays for fingerprint sensing on IC comprising exemplary one or more exemplary PMUTs integrated on exemplary CMOS wafer 3102, in accordance with further non-limiting embodiments. As a non-limiting example, exemplary CMOS wafer 3102 can comprise exemplary source/drain regions 3104, gate 3106, one or more vias 3108, and one or more metal layers including a first metal layer 3110 and an exemplary top metal layer 3112. In a non-limiting aspect, an exemplary top metal layer 3112 of exemplary CMOS wafer 3102 can comprise aluminum. In addition, exemplary CMOS wafer 3102 can comprise an exemplary silicon dioxide layer 3114 disposed over the exemplary top metal layer 3112 and an exemplary passivation layer 3116 disposed over the exemplary silicon dioxide layer 3114.

Figure 32:
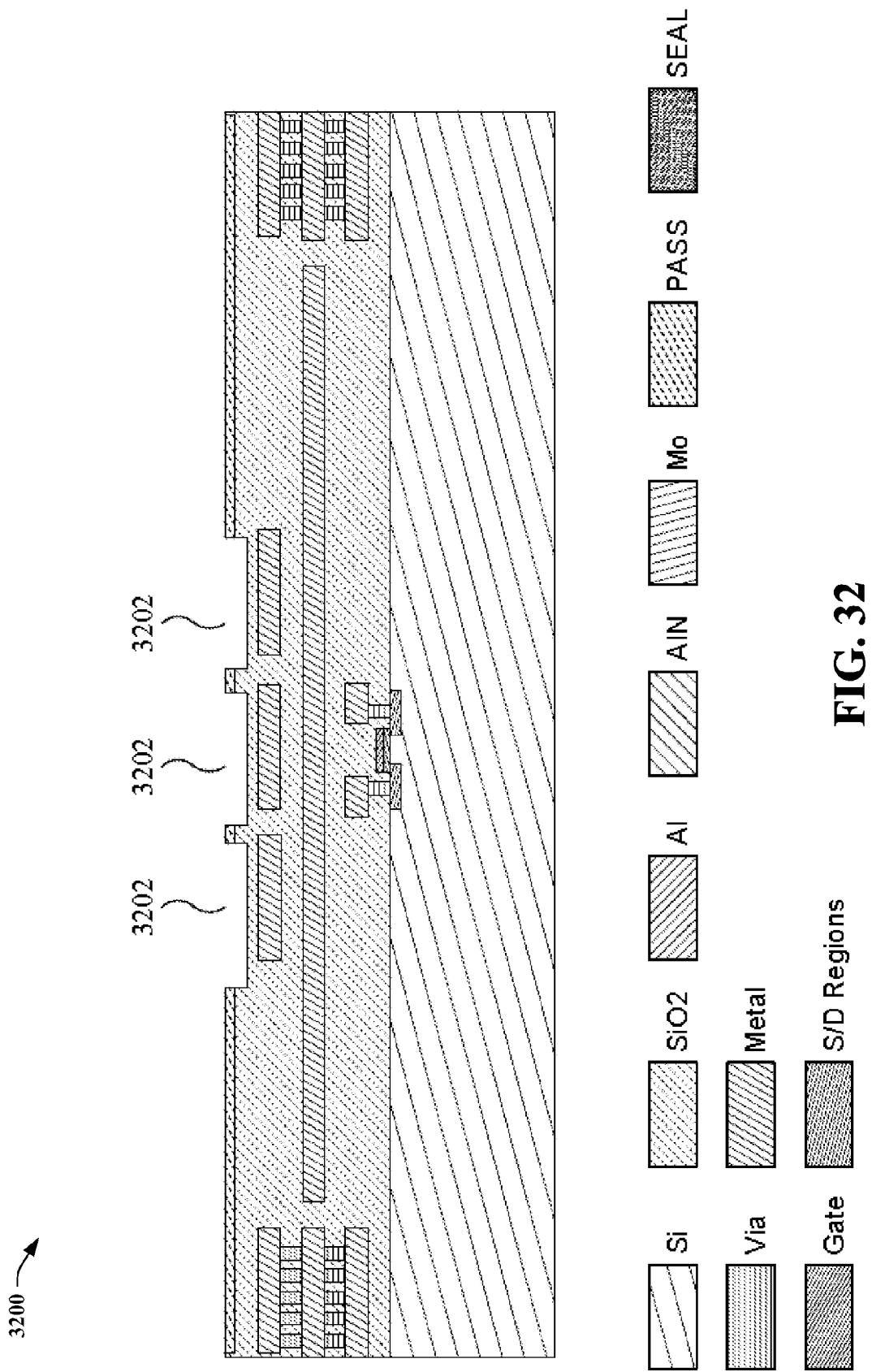
FIG. 32 depicts a cross-section of an exemplary CMOS wafer comprising one or more exemplary cavities, in accordance with further aspects described herein directed to a non-limiting cavity deposition etch process.

FIG. 32 depicts a cross-section 3200 of an exemplary CMOS wafer 3102 comprising one or more exemplary cavities 3202, in accordance with further aspects described herein directed to a non-limiting cavity deposition etch process. As a non-limiting example, exemplary passivation layer 3116 and exemplary silicon dioxide layer 3114 can be etched in a desired pattern with a timed etch is then performed to create the one or more exemplary cavities 3202. In a further non-limiting aspect, the one or more exemplary cavities 3202 can be created by employing a timed etch, resulting in an exemplary cavity depth of less than 0.8 µm (+/−10%).

Figure 33:
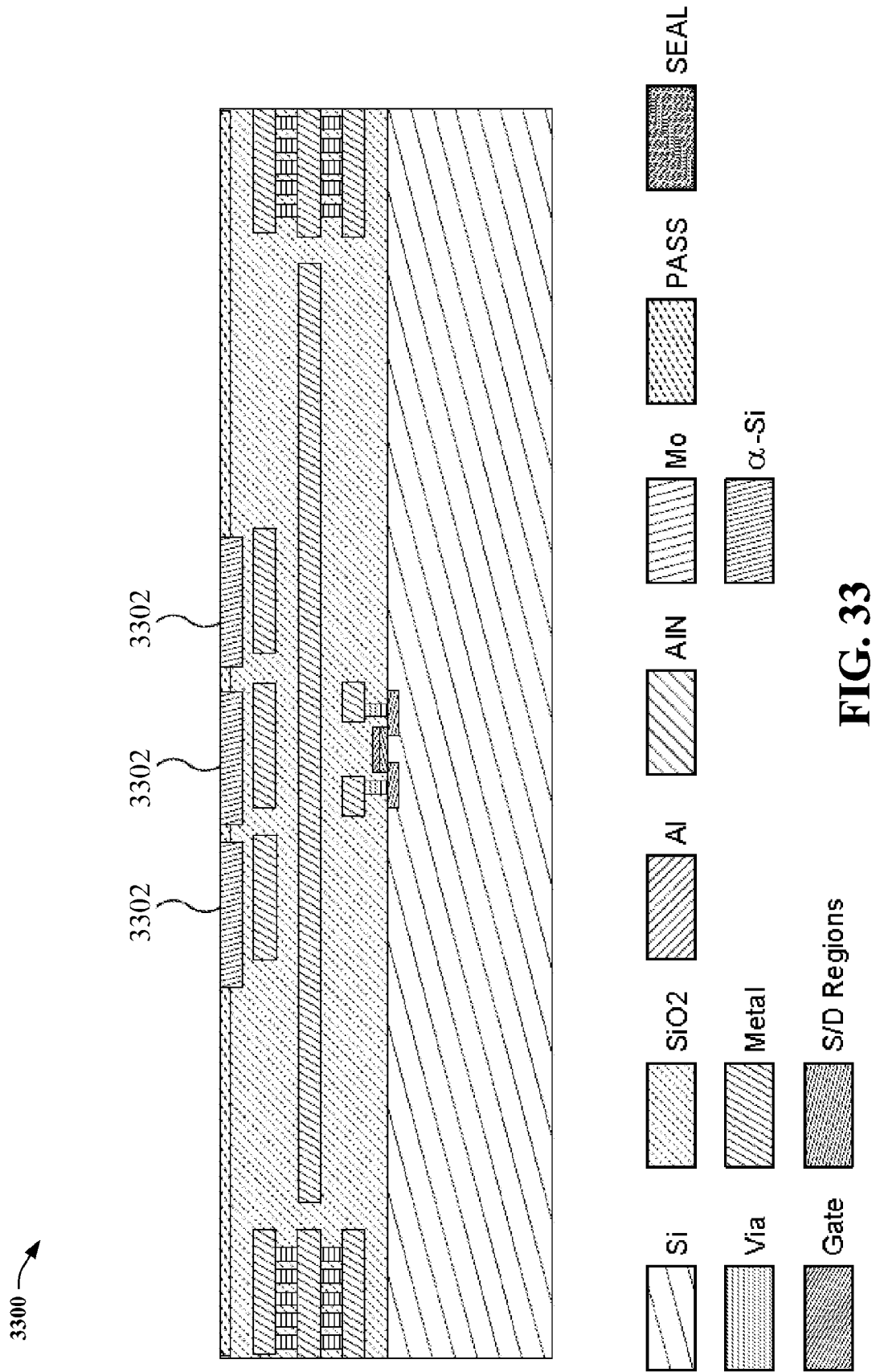
FIG. 33 depicts a cross-section of an exemplary CMOS wafer comprising one or more exemplary sacrificial materials, in accordance with further aspects described herein directed to non-limiting amorphous silicon deposition and subsequent chemical-mechanical planarizing processes.

FIG. 33 depicts a cross-section 3300 of an exemplary CMOS wafer 3102 comprising one or more exemplary sacrificial materials 3302, in accordance with further aspects described herein directed to non-limiting amorphous silicon deposition and subsequent chemical-mechanical planarizing processes. As a non-limiting example, one or more exemplary sacrificial materials 3302, e.g., such as amorphous silicon, etc. can be deposited in the one or more exemplary cavities 3202. In a non-limiting aspect, the one or more exemplary sacrificial materials 3302 can comprise amorphous silicon. In a further non-limiting aspect, the one or more exemplary sacrificial materials 3302 can comprise silicon-germanium (SiGe) or tungsten (W), which including amorphous silicon are all CMOS foundry compatible materials and can be removed with xenon difluoride ($XeF_2$) or sulfur hexafluoride ($SF_6$). In another non-limiting aspect, exemplary CMOS wafer 3102 comprising one or more exemplary sacrificial materials 3302 can be polished (e.g., chemical-mechanical planarizing) to planarize the surface, resulting in a sacrificial material film thickness of about less than 0.8 µm to prevent cracking and peeling of the sacrificial material film.

Figure 34:
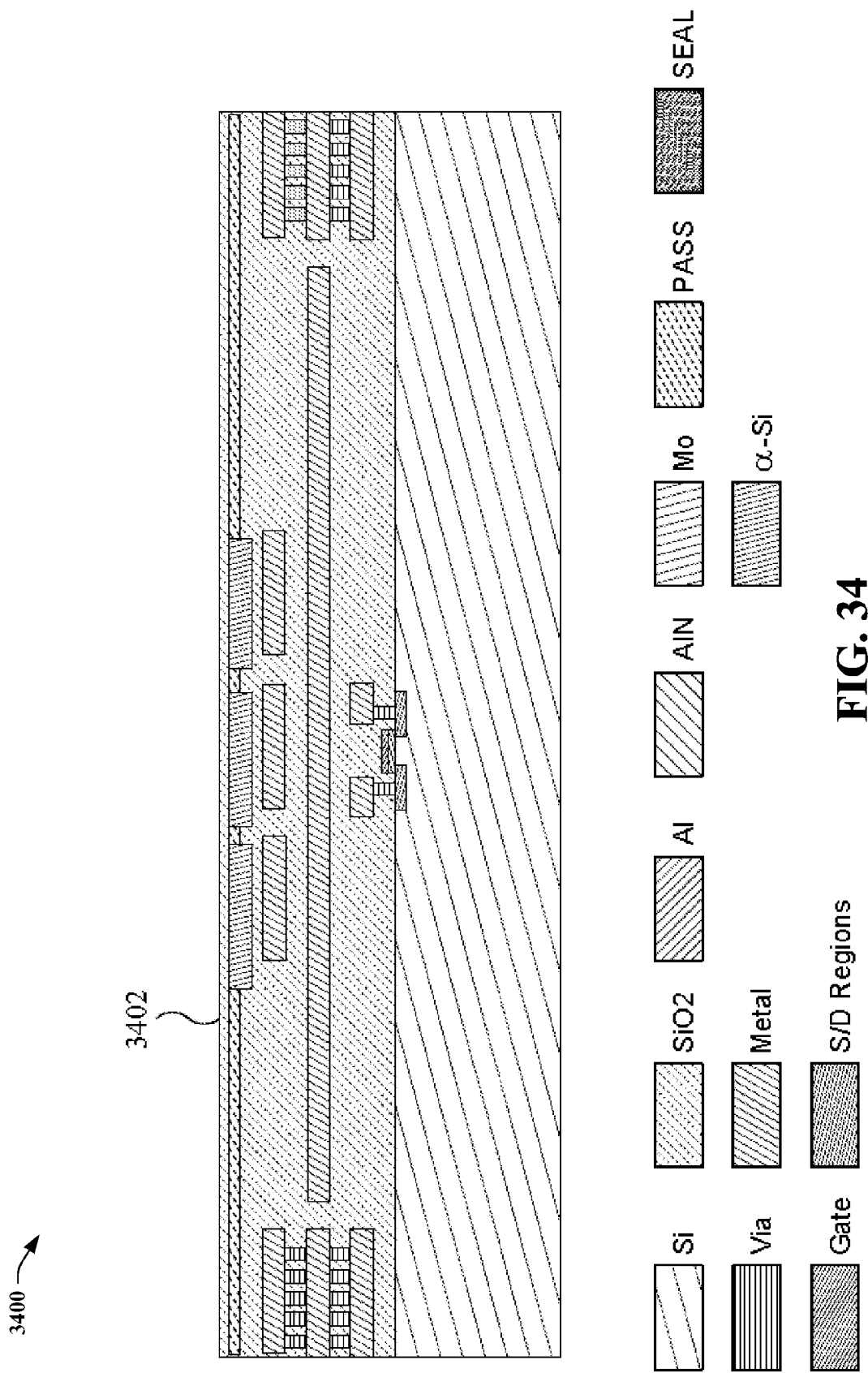
FIG. 34 depicts a cross-section of an exemplary CMOS wafer comprising one or more exemplary silicon dioxide ($SiO_2$) layers, in accordance with further aspects described herein directed to a non-limiting silicon dioxide deposition process.

FIG. 34 depicts a cross-section 3400 of an exemplary CMOS wafer 3102 comprising one or more exemplary silicon dioxide ($SiO_2$) layers 3402, in accordance with further aspects described herein directed to a non-limiting silicon dioxide deposition process. As a non-limiting example, one or more exemplary silicon dioxide ($SiO_2$) layers 3402 can be deposited to cover the surface of the exemplary CMOS wafer 3102 comprising one or more exemplary sacrificial materials 3302 and serve as a structure material in the fabrication of one or more exemplary PMUTs integrated on exemplary CMOS wafer 3102, in accordance with further non-limiting embodiments.

Figure 35:
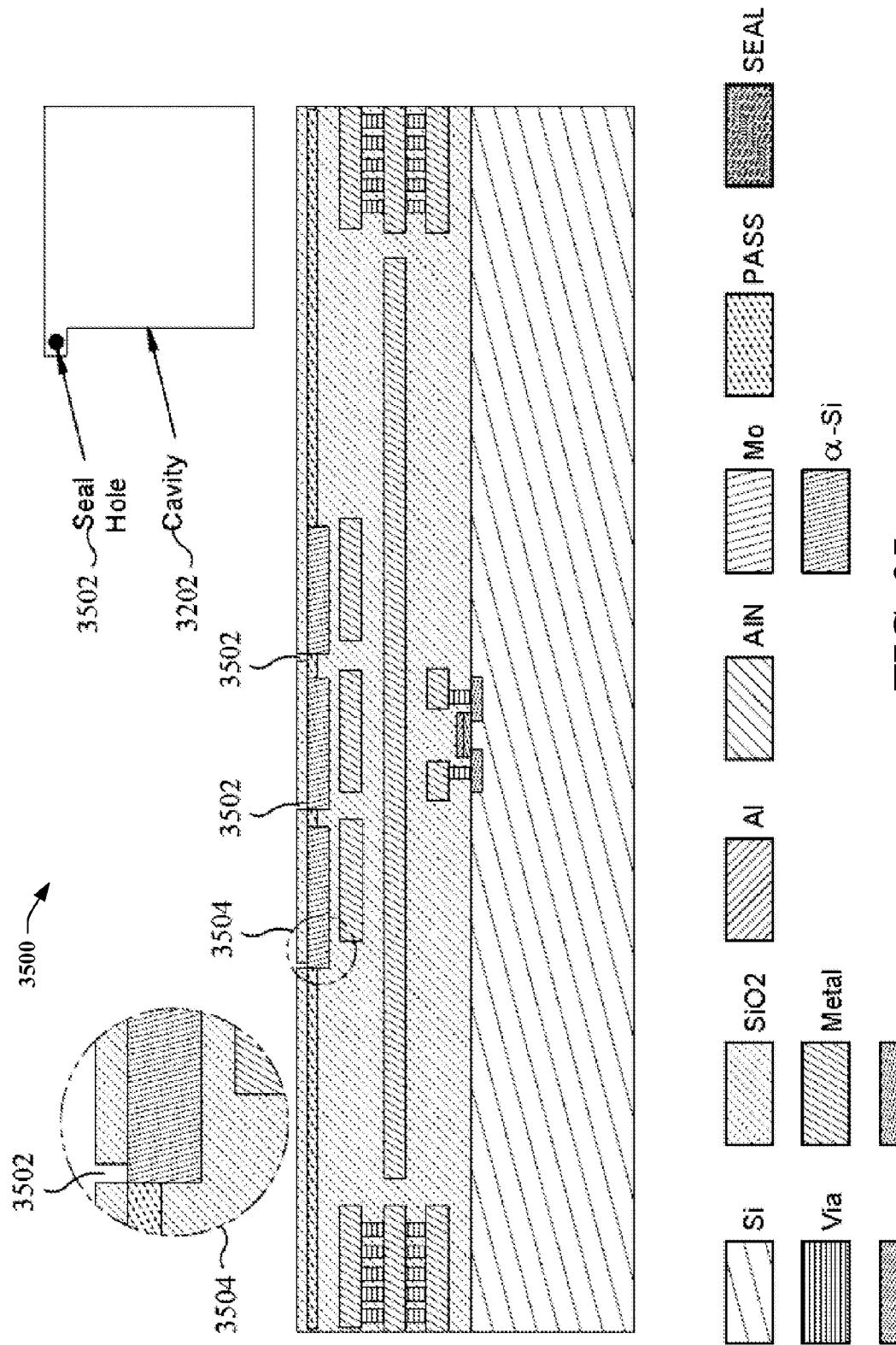
FIG. 35 depicts a cross-section of an exemplary CMOS wafer comprising one or more exemplary seal holes, in accordance with further aspects described herein directed to a non-limiting release hole opening process.

FIG. 35 depicts a cross-section 3500 of an exemplary CMOS wafer 3102 comprising one or more exemplary seal holes 3502, in accordance with further aspects described herein directed to a non-limiting release hole opening process. Accordingly, in a further non-limiting aspect, exemplary CMOS wafer 3102 comprising one or more exemplary silicon dioxide ($SiO_2$) layers 3402 can be etched to create one or more seal holes. In another non-limiting aspect, for example, as depicted inset 3504, a seal hole profile having an aspect ratio greater than 4 can facilitate providing adequate sealing of the one or more exemplary cavities 3202. In addition, in a further non-limiting aspect, layout for the one or more exemplary cavities 3202 and one or more exemplary seal holes 3502 can comprise the one or more exemplary seal holes 3502 placed at the respective edges of the one or more exemplary cavities 3202, such that sealing of the one or more exemplary seal holes 3502 does not create an obstruction if the area in the one or more exemplary cavities 3202 directly underneath the one or more exemplary seal holes 3502 is fully filled, for example, as depicted in FIG. 35.

Figure 36:
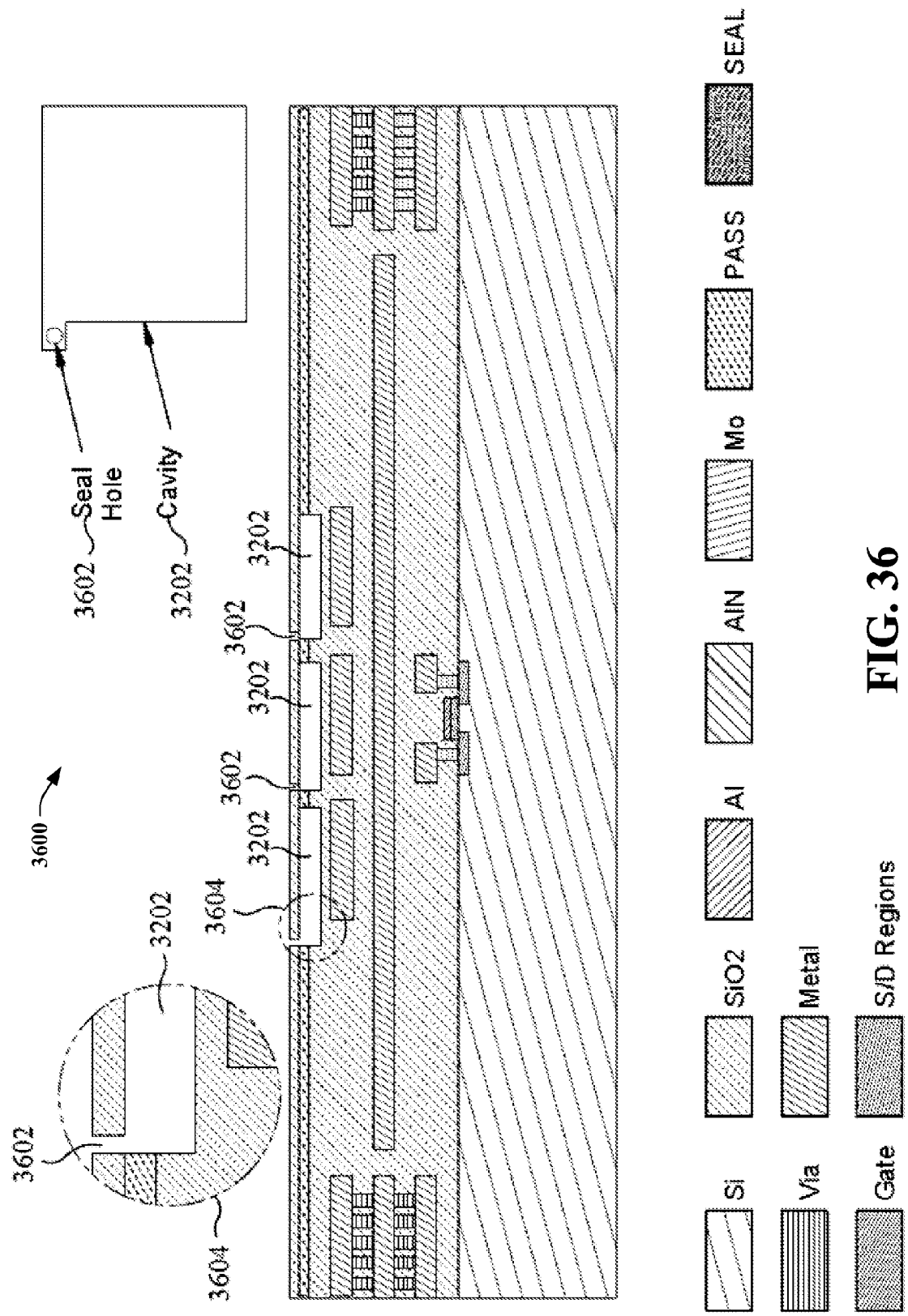
FIG. 36 depicts a cross-section of an exemplary CMOS wafer comprising one or more exemplary cavities, in accordance with further aspects described herein directed to a non-limiting release etch process.

FIG. 36 depicts a cross-section 3600 of an exemplary CMOS wafer 3102 comprising one or more exemplary cavities 3202, in accordance with further aspects described herein directed to a non-limiting release etch process. Accordingly, in a further non-limiting aspect, exemplary CMOS wafer 3102 comprising the one or more exemplary seal holes 3502 and one or more exemplary sacrificial materials 3302 can be exposed to a sacrificial release etch to remove the one or more exemplary sacrificial materials 3302 (e.g., amorphous silicon, etc.). In a non-limiting aspect, exemplary CMOS wafer 3102 comprising the one or more exemplary seal holes 3502 and one or more exemplary sacrificial materials 3302 can be exposed to a sacrificial release etch employing either a dry etch or a wet etch. As a non-limiting example, an exemplary dry etch can employ XeF2 or SF6 as etching gas. In a further non-limiting example, an exemplary wet etch can employ poly-etch (e.g., H:N:A, or a solution of Hydrofluoric Acid (HF):Nitric Acid ($HNO_3$):Acetic acid ($CH_3COOH$) in a desired ratio), potassium hydroxide (KOH) or tetramethyl ammonium hydroxide (TMAH), with care taken to prevent stiction of the membrane created from the one or more exemplary silicon dioxide ($SiO_2$) layers 3402. The one or more exemplary sacrificial materials 3302 thus removed, FIG. 36 depicts exemplary CMOS wafer 3102 comprising one or more exemplary cavities 3202 and one or more exemplary unsealed seal holes 3602, for example, in inset 3604.

Figure 37:
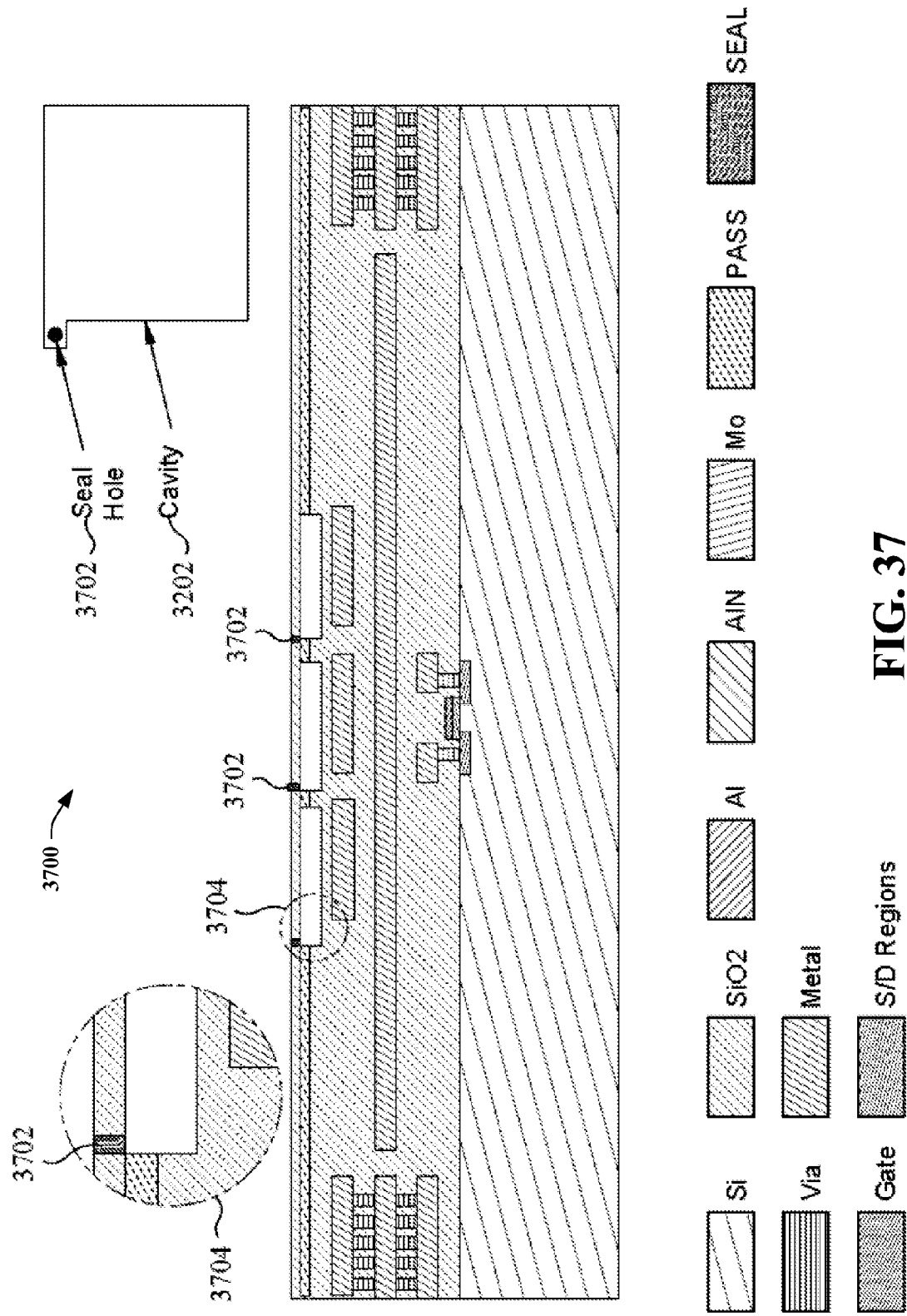
FIG. 37 depicts a cross-section of an exemplary CMOS wafer comprising one or more exemplary seal hole seals, in accordance with further aspects described herein directed to non-limiting seal deposition and etch back processes.

FIG. 37 depicts a cross-section 3700 of an exemplary CMOS wafer 3102 comprising one or more exemplary seal hole seals 3702, in accordance with further aspects described herein directed to non-limiting seal deposition and etch back processes. As a non-limiting example, exemplary CMOS wafer 3102 comprising one or more exemplary cavities 3202 and one or more exemplary unsealed seal holes 3602 can be exposed to a plasma-enhanced chemical vapor deposition (PECVD) process for $SiO_2$ deposition to create the one or more exemplary seal hole seals 3702 as depicted in inset 3704. As can be understood, the PECVD of $SiO_2$ can create additional thickness of silicon dioxide which can be subject to an etch back process to control the final structure membrane thickness. It is further noted that, $SiO_2$ is defect tolerable for subsequent AlN deposition.

Figure 38:
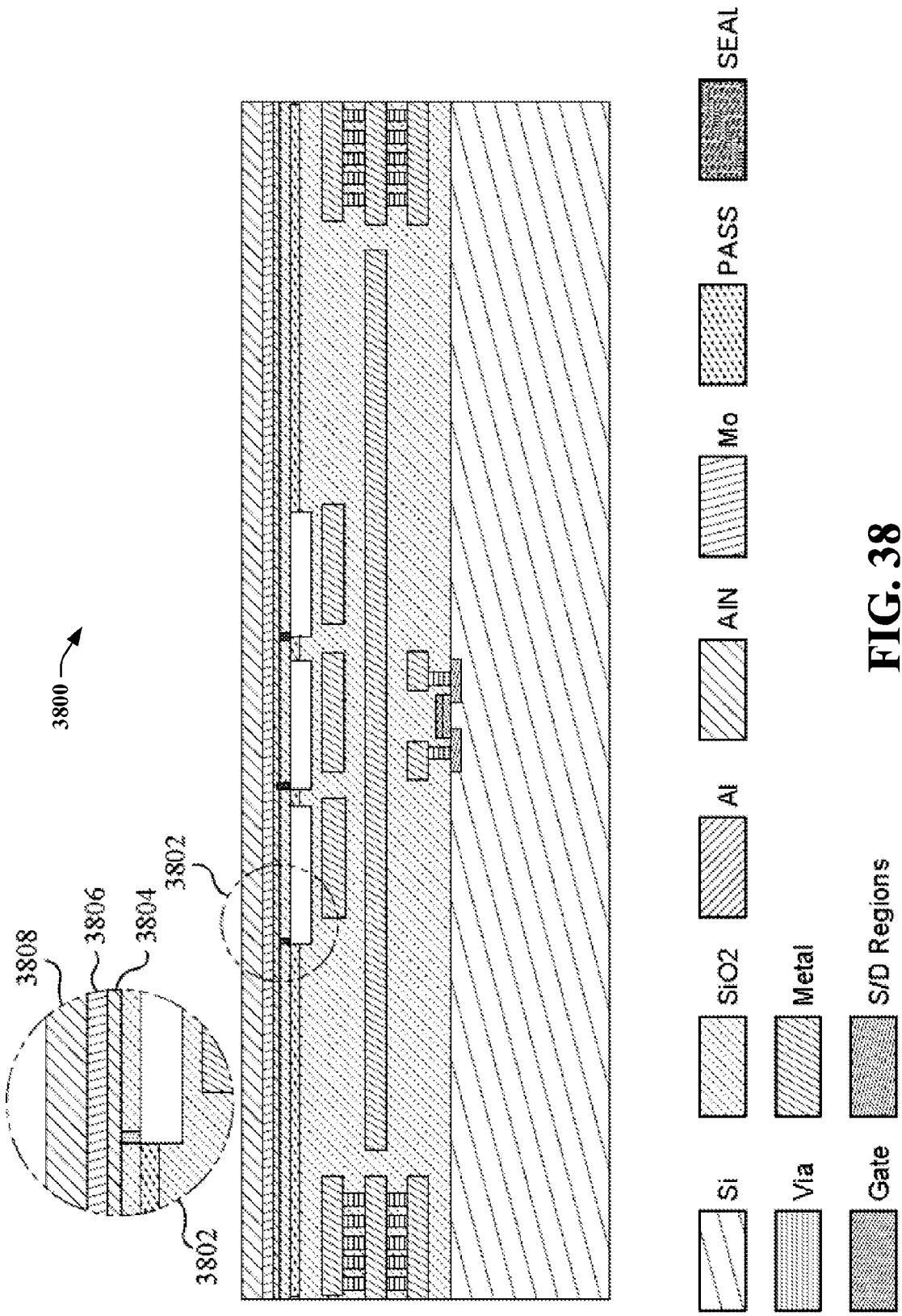
FIG. 38 depicts a cross-section of an exemplary CMOS wafer comprising exemplary aluminum nitride (AlN) seed layer, molybdenum (Mo) layer, and AlN stacking layer, in accordance with further aspects described herein directed to non-limiting AlN Seed/Mo/AlN deposition processes.

FIG. 38 depicts a cross-section 3800 of an exemplary CMOS wafer 3102, in inset 3802, for example, comprising an exemplary aluminum nitride (AlN) seed layer 3804, molybdenum (Mo) layer 3806, and AlN stacking layer 3808, in accordance with further aspects described herein directed to non-limiting AlN Seed/Mo/AlN deposition processes, for example, as further describe above regarding FIGS. 9A-9K, 27, etc.

Figure 39:
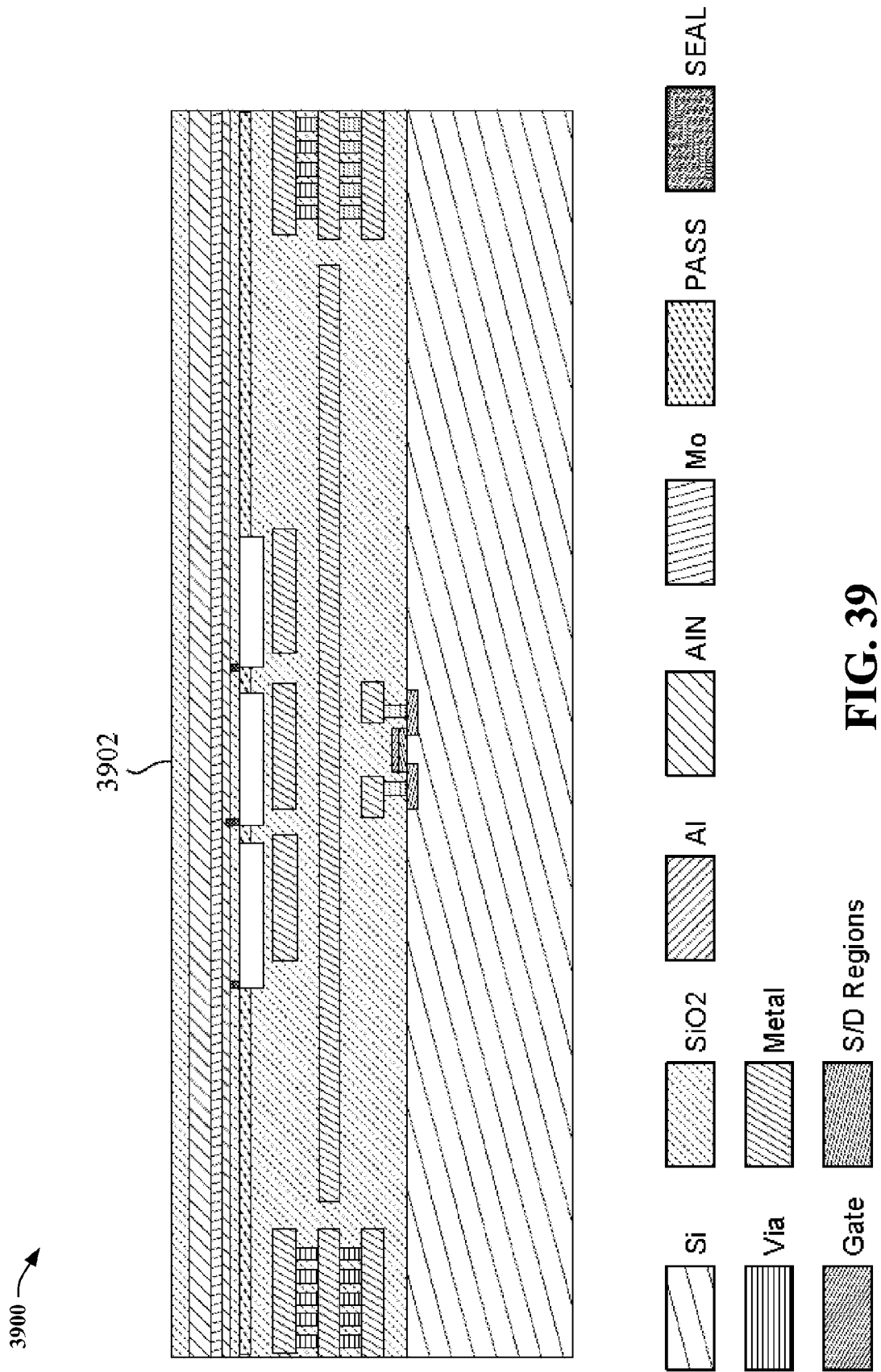
FIG. 39 depicts a cross-section of an exemplary CMOS wafer comprising one or more exemplary $SiO_2$ layers, in accordance with further aspects described herein directed to a non-limiting hard mask deposition process.
Figure 40:
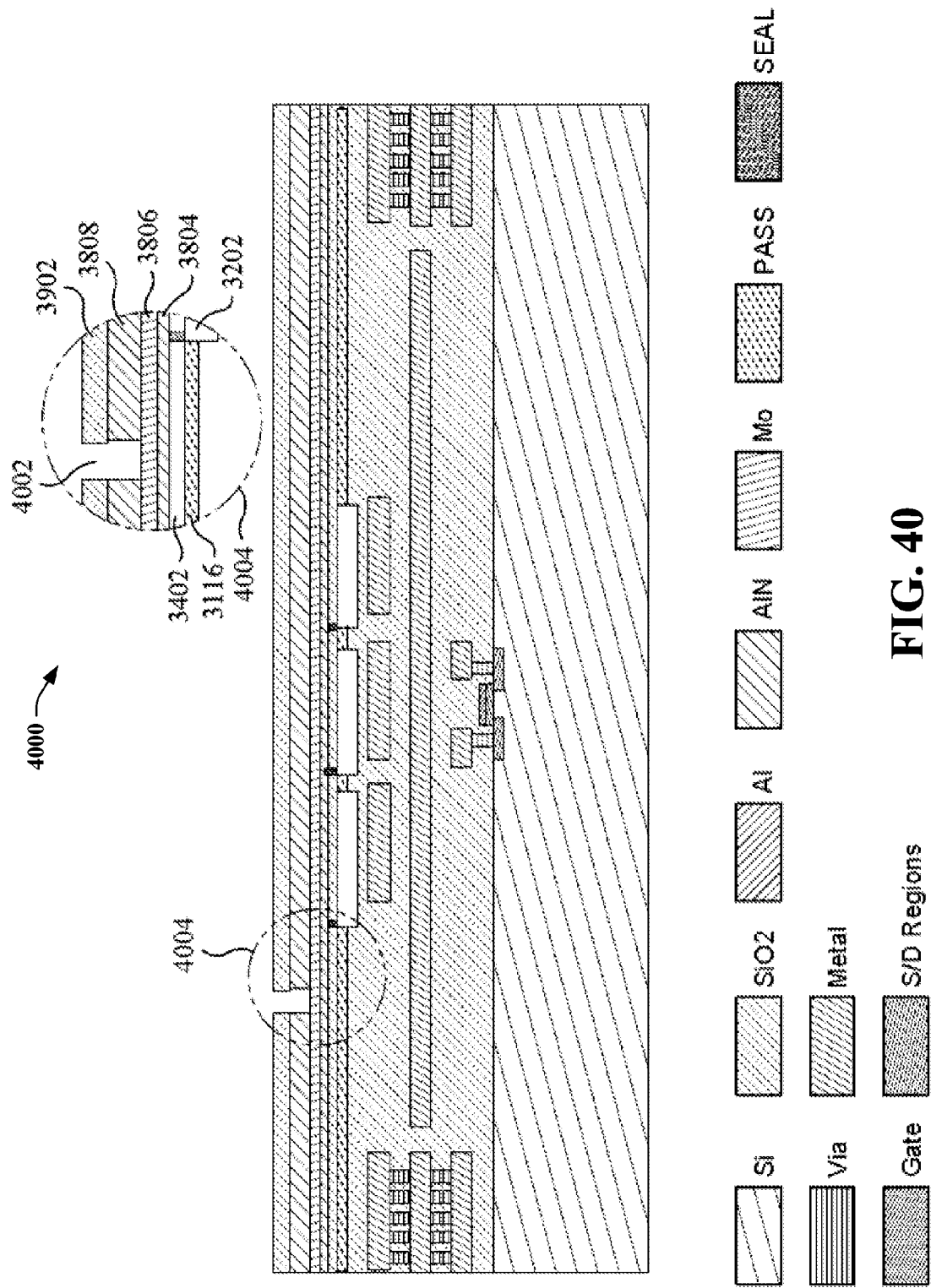
FIG. 40 depicts a cross-section of an exemplary CMOS wafer comprising one or more exemplary bottom contacts, in accordance with further aspects described herein directed to a non-limiting bottom contact to molybdenum fabrication process.
Figure 41:
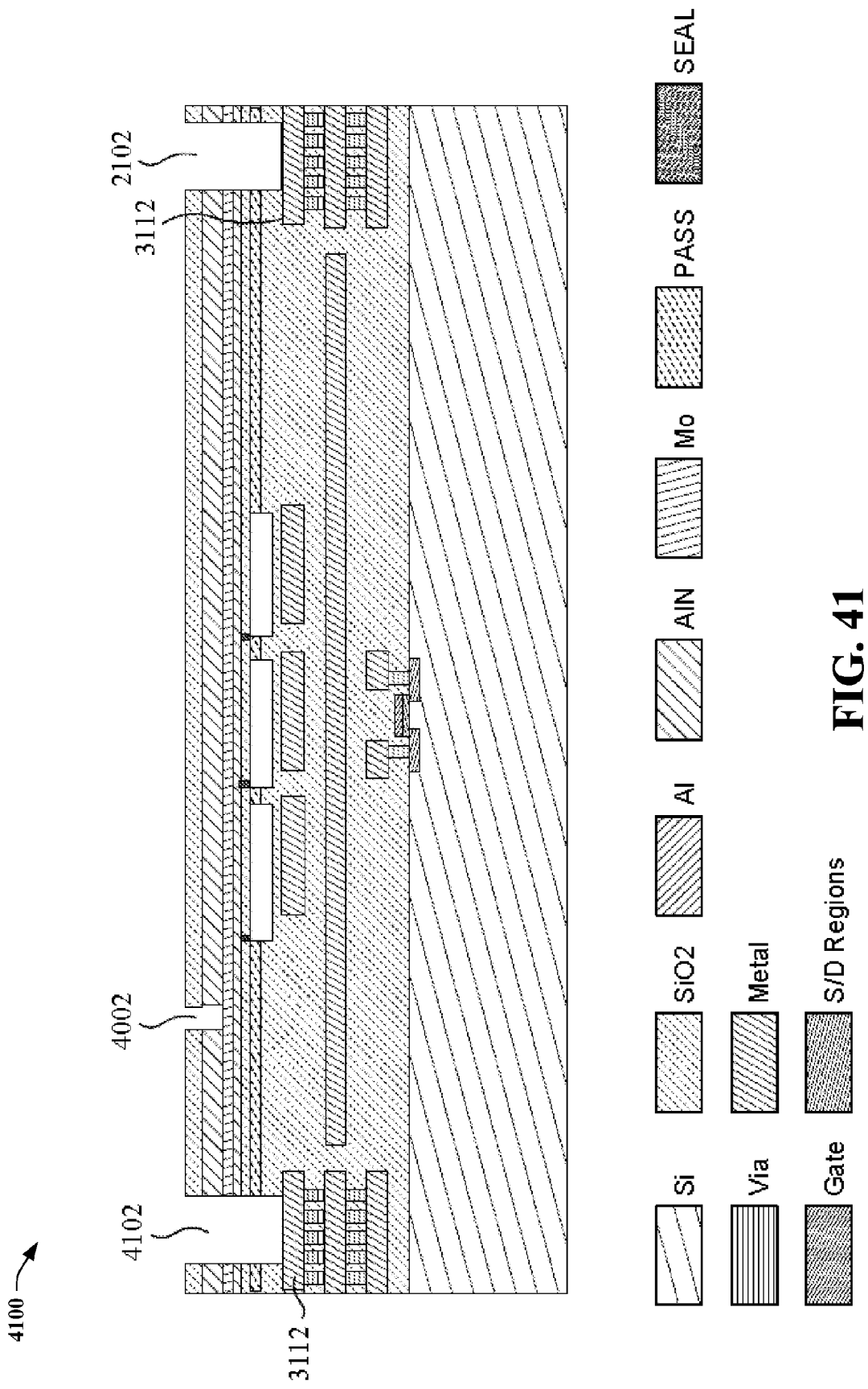
FIG. 41 depicts a cross-section of an exemplary CMOS wafer comprising one or more exemplary vias, in accordance with further aspects described herein directed to a non-limiting wafer via etch process.
Figure 42:
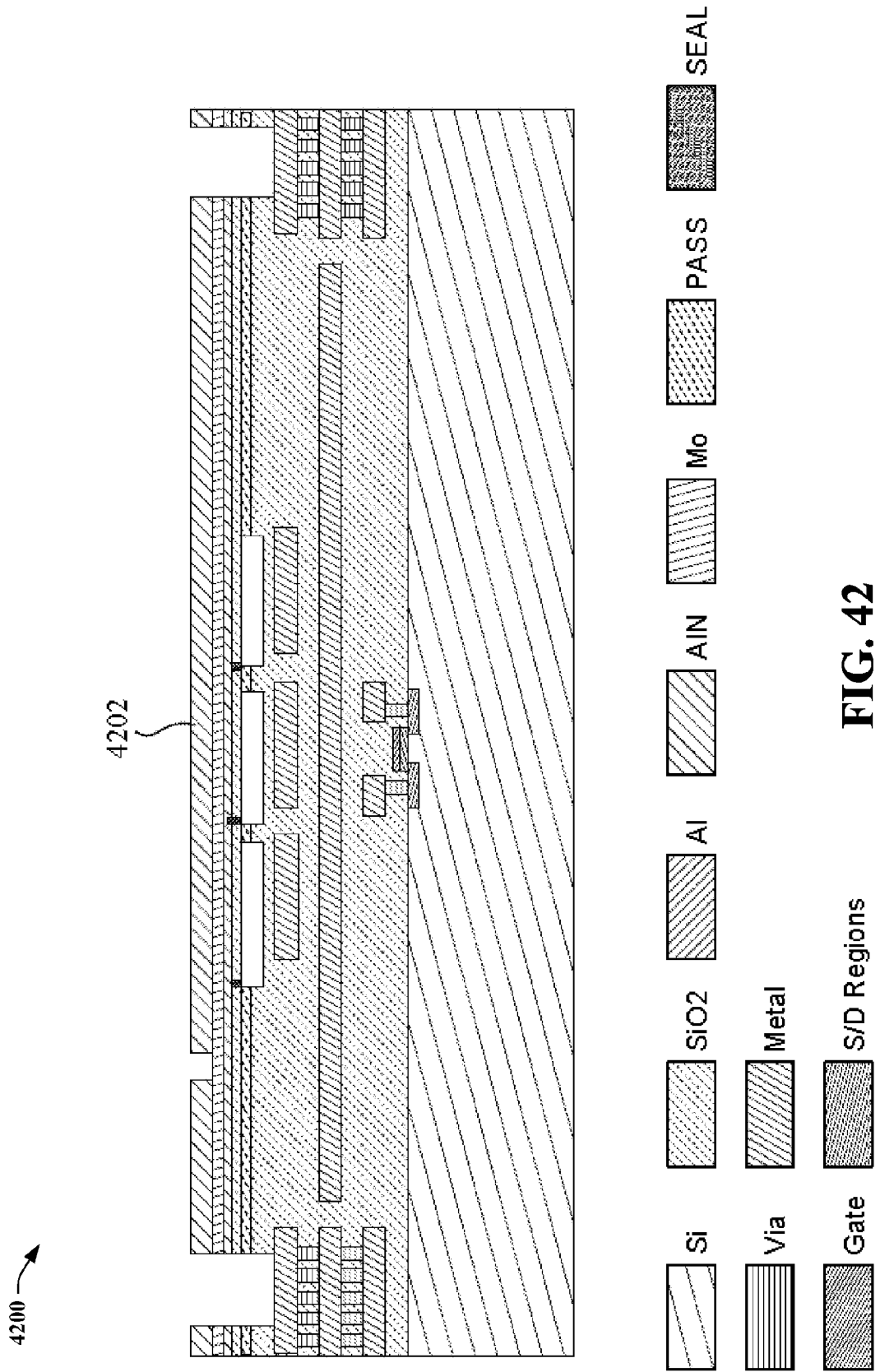
FIG. 42 depicts a cross-section of an exemplary CMOS wafer comprising an exposed MN surface, in accordance with further aspects described herein directed to a non-limiting hard mask removal process.

One or more exemplary bottom contacts 4002 to molybdenum (Mo) layer 3806 and one or more exemplary vias 4102 contact to exemplary top metal layer 3112 of exemplary CMOS wafer 3102 can then be created by employing a hard mask on top of AlN stacking layer 3808. Thus, FIG. 39 depicts a cross-section 3900 of an exemplary CMOS wafer 3102 comprising one or more exemplary $SiO_2$ layers 3902, in accordance with further aspects described herein directed to a non-limiting hard mask deposition process. In addition, FIG. 40 depicts a cross-section 4000 of an exemplary CMOS wafer 3102, in inset 4004 comprising one or more exemplary bottom contacts 4002, in accordance with further aspects described herein directed to a non-limiting bottom contact to molybdenum fabrication process. In a non-limiting aspect, in addition to etching one or more exemplary bottom contacts 4002 to molybdenum (Mo) layer 3806, areas comprising AlN (e.g., selected areas of AlN stacking layer 3808) over the one or more exemplary vias 4102 contact to exemplary top metal layer 3112 can also be etched to reduce etch difficulty in fabricating the one or more exemplary vias 4102 contact to exemplary top metal layer 3112. Thus, FIG. 41 depicts a cross-section 4100 of an exemplary CMOS wafer comprising 3102 one or more exemplary vias 4102, in accordance with further aspects described herein directed to a non-limiting wafer via etch process. Subsequently, the hard mask comprising one or more exemplary $SiO_2$ layers 3902 can be removed as shown in FIG. 42, which depicts a cross-section 4200 of an exemplary CMOS wafer 3102 comprising an exposed AlN surface 4202 (e.g., AlN stacking layer 3808), in accordance with further aspects described herein directed to a non-limiting hard mask removal process.

Figure 43:
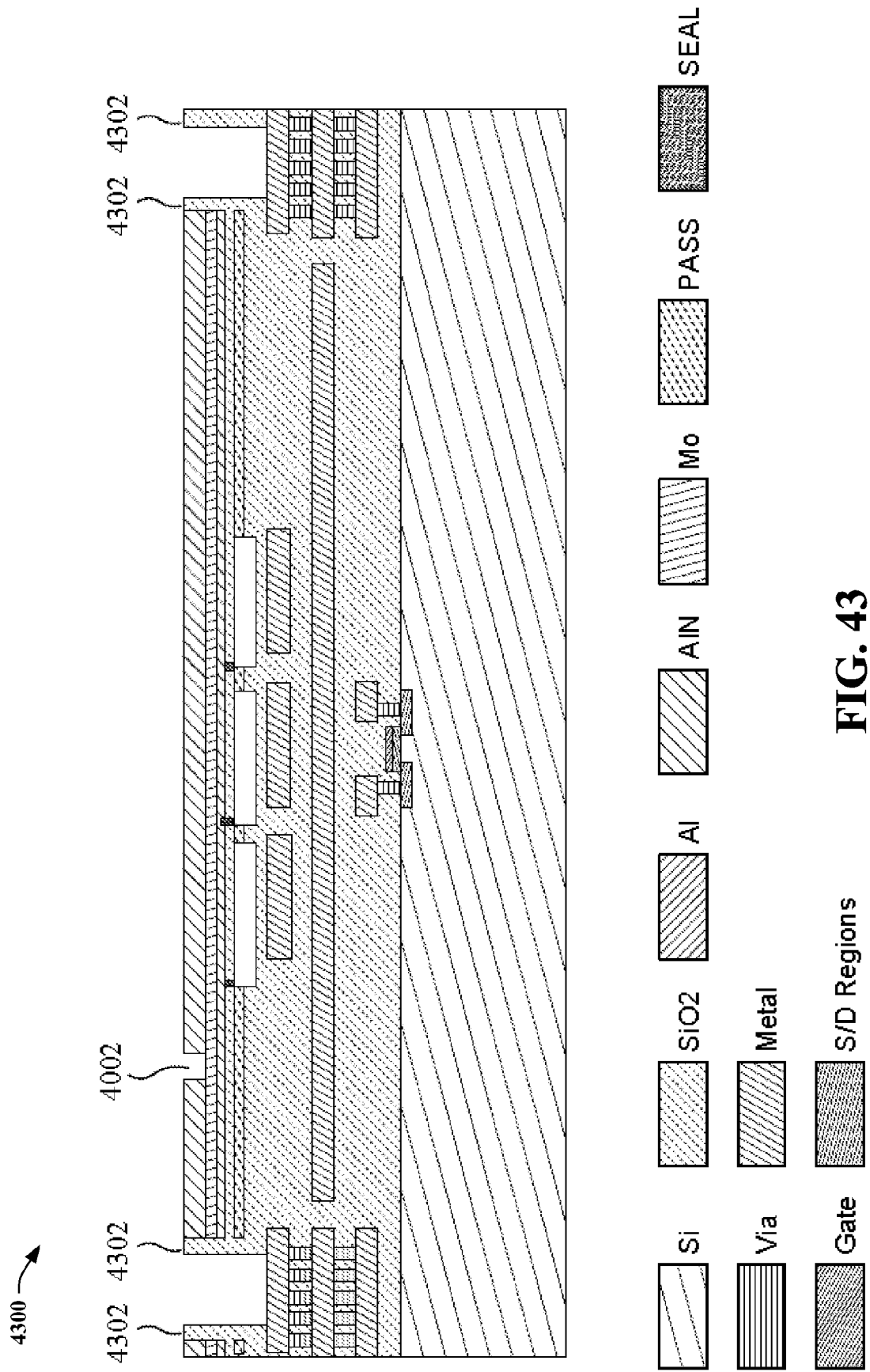
FIG. 43 depicts a cross-section of an exemplary CMOS wafer comprising one or more exemplary SiO2 spacers, in accordance with further aspects described herein directed to a non-limiting SiO2 spacer fabrication process.
Figure 44:
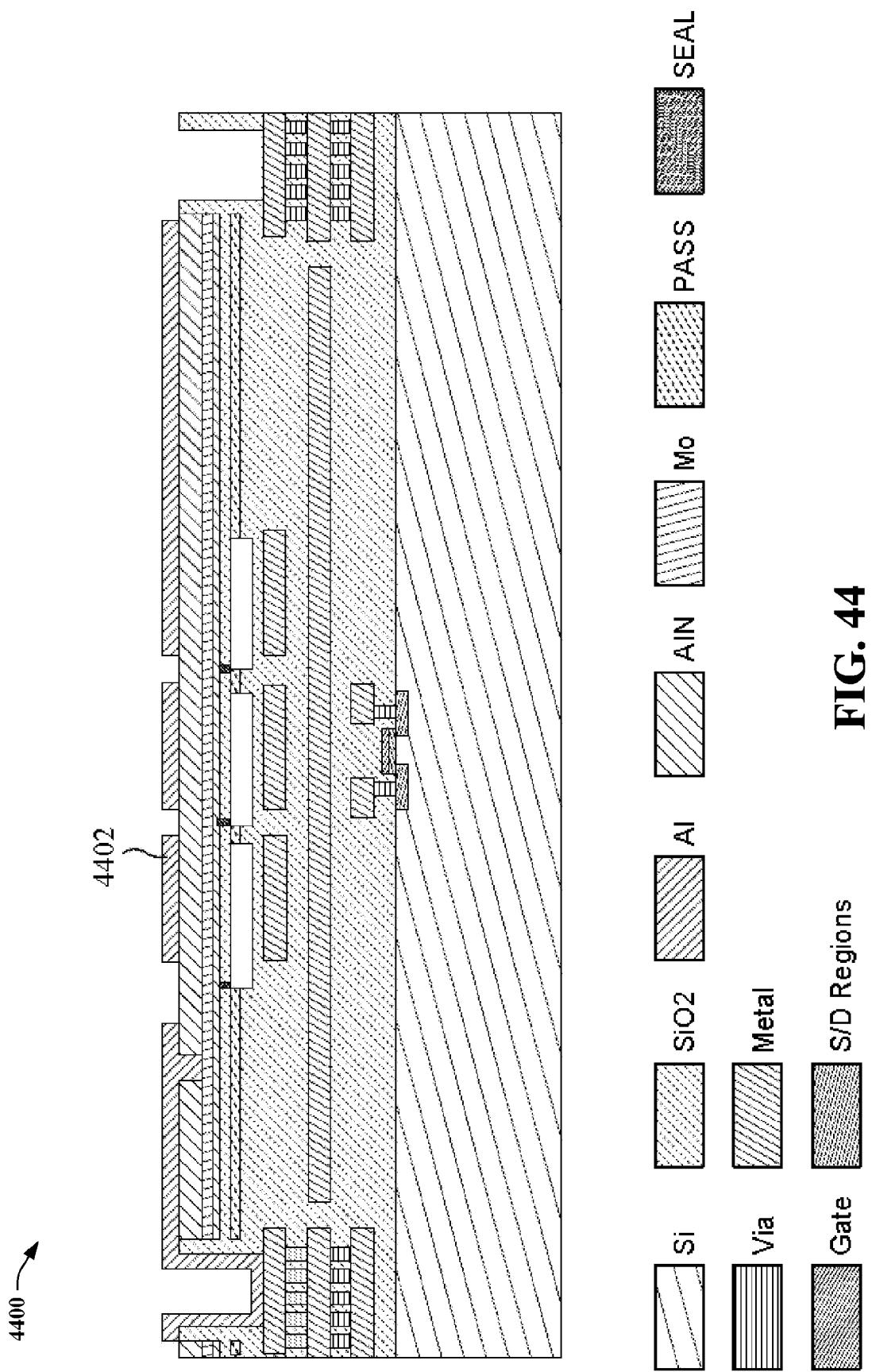
FIG. 44 depicts a cross-section of an exemplary CMOS wafer comprising one or more exemplary top electrodes, in accordance with further aspects described herein directed to a non-limiting top electrode fabrication process.

FIG. 43 depicts a cross-section of an exemplary CMOS wafer comprising one or more exemplary $SiO_2$ spacers 4302, in accordance with further aspects described herein directed to a non-limiting $SiO_2$ spacer fabrication process. As a non-limiting example, a layer of $SiO_2$ (not shown) can be deposited and blank etched (e.g., without a mask material such as a photo resistive layer described above) to remove the top surface oxide completely while preserving the one or more exemplary $SiO_2$ spacers 4302. FIG. 44 depicts a cross-section 4400 of an exemplary CMOS wafer 3102 comprising one or more exemplary top electrodes 4402, in accordance with further aspects described herein directed to a non-limiting top electrode fabrication process. As a non-limiting example, one or more exemplary top electrodes 4402 material (e.g., aluminum, etc.) can be deposited and patterned to form the one or more exemplary top electrodes 4402 for exemplary PMUT and PMUT arrays and to form electrical connection to exemplary top metal layer 3112 of exemplary CMOS wafer 3102. As can be seen FIGS. 43-44, preserving the one or more exemplary $SiO_2$ spacers 4302 can prevent shorting of the one or more exemplary top electrodes 4402 and the one or more exemplary bottom contacts 4002 to the bottom electrode and exemplary aluminum nitride (AlN) seed layer 3804.

Figure 45:
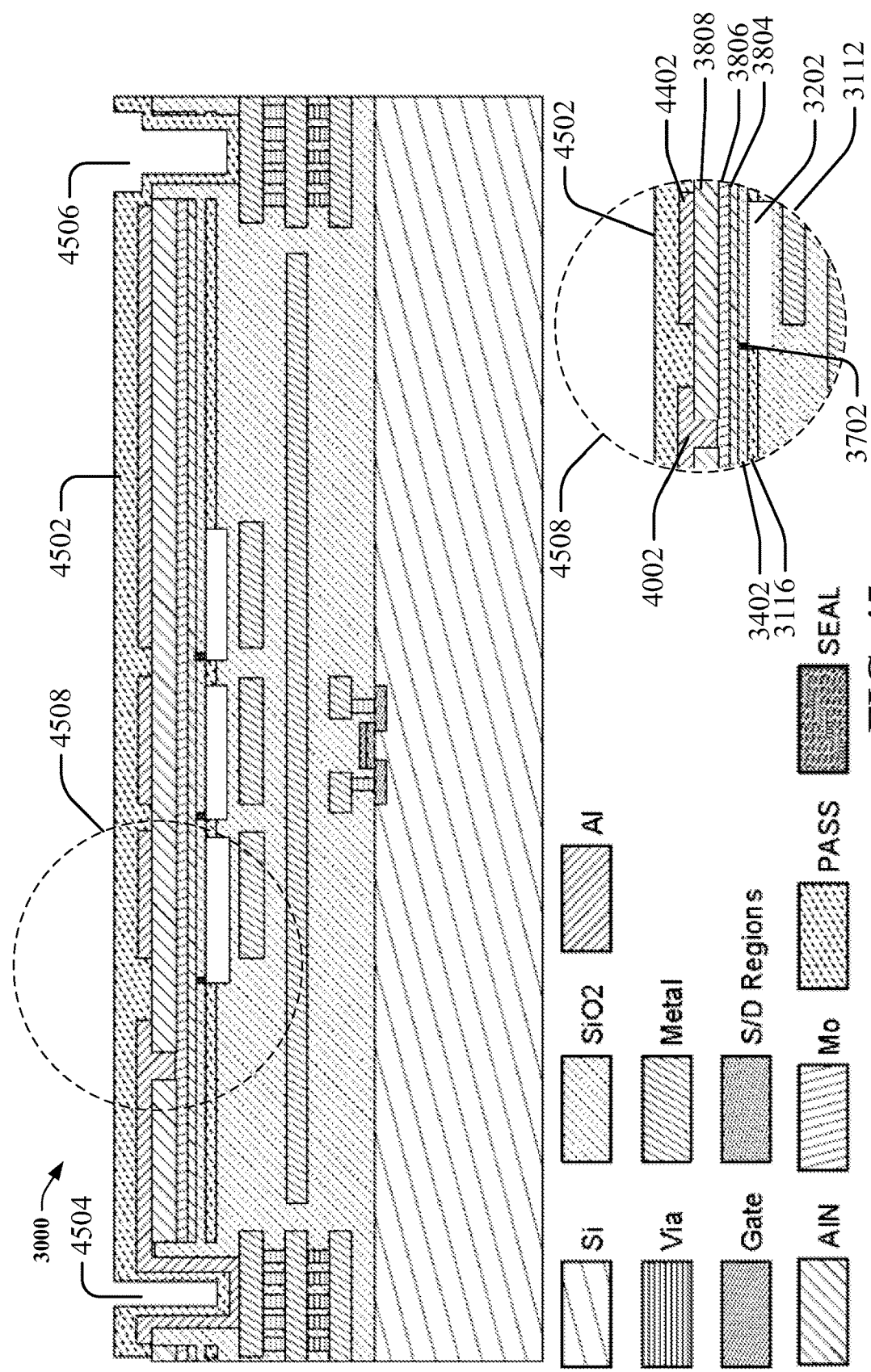
FIG. 45 depicts exemplary PMUT for fingerprint sensing on IC comprising exemplary PMUT integrated on exemplary CMOS wafer as described above regarding FIG. 30, and which exemplary CMOS wafer comprises one or more exemplary passivation layers, in accordance with further aspects described herein directed to a non-limiting passivation process.

FIG. 45 depicts exemplary PMUT for fingerprint sensing on IC comprising exemplary PMUT 3000 integrated on exemplary CMOS wafer 3102 as described above regarding FIGS. 30-44, for which exemplary CMOS 3102 wafer comprises one or more exemplary passivation layers 4502, in accordance with further aspects described herein directed to a non-limiting passivation process. As a non-limiting example, one or more exemplary passivation layers 4502 can be deposited on exemplary CMOS 3102 wafer and patterned to open one or more wire bond pads 4504 and/or one or more vias 4506 of exemplary PMUT 3000 integrated on exemplary CMOS wafer 3102. As described above, inset 4508 depicts various non-limiting aspects of exemplary PMUT 3000 integrated on exemplary CMOS wafer 3102, for example, as described above regarding FIGS. 31-45.

Accordingly, various non-limiting embodiments of the subject disclosure can comprise an exemplary MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.), comprising a MUT structure (e.g., exemplary PMUT 2700 or portions thereof, exemplary PMUT 3000 or portions thereof, etc.) and a piezoelectric material (e.g., one or more of aluminum nitride, lead zirconate titanate (PZT), zinc oxide, polyvinylidene difluoride (PVDF), lithium niobate (LiNbO3)) disposed within the MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.) comprising a PMUT array of a fingerprint sensor adapted to sense a characteristic of a fingerprint placed adjacent to the MUT structure.

Further non-limiting embodiments of the subject disclosure can comprise an exemplary MEMS device (e.g., exemplary PMUT 3000 integrated on exemplary CMOS wafer 3102, etc.) comprising a MUT structure (e.g., exemplary PMUT 3000 or portions thereof, etc.) formed integrally to the CMOS structure (e.g., exemplary CMOS wafer 3102 or portions thereof, etc.) having a plurality of cavities (e.g., one or more exemplary cavities 3202, etc.) formed within the CMOS structure and the piezoelectric material (e.g., one or more of aluminum nitride, lead zirconate titanate (PZT), zinc oxide, polyvinylidene difluoride (PVDF), lithium niobate (LiNbO3)) disposed on the CMOS structure.

In a non-limiting aspect, exemplary MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.) can further comprise a first metal conductive layer (e.g., such as described regarding aluminum top electrode 2724, regarding one or more exemplary top electrodes 4402, etc., in reference to FIGS. 27 and 44) disposed on the piezoelectric material (e.g., one or more of aluminum nitride, lead zirconate titanate (PZT), zinc oxide, polyvinylidene difluoride (PVDF), lithium niobate (LiNbO3)).

In a further non-limiting aspect, exemplary MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.) can further comprise a plurality of metal electrodes (e.g., one or more of aluminum top electrodes 2724, one or more bottom electrodes 2720, one or more exemplary top electrodes 4402, one or more exemplary bottom contacts 4002, etc.) configured to form electrical connections between the first metal conductive layer (e.g., such as described regarding aluminum top electrode 2724, regarding one or more exemplary top electrodes 4402, etc., in reference to FIGS. 27 and 44), the piezoelectric material (e.g., one or more of aluminum nitride, lead zirconate titanate (PZT), zinc oxide, polyvinylidene difluoride (PVDF), lithium niobate (LiNbO3)), and a CMOS structure (e.g., exemplary CMOS wafer 2802 or portions thereof, exemplary CMOS wafer 3102 or portions thereof, etc.), wherein the pMUT structure and the CMOS structure are vertically stacked, for example, as depicted in FIGS. 28, 45, etc.

In a further non-limiting aspect, exemplary MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.) can further comprise a second metal conductive layer (e.g., molybdenum (Mo) layer 2712, molybdenum (Mo) layer 3806, etc.) disposed on the piezoelectric material (e.g., one or more of aluminum nitride, lead zirconate titanate (PZT), zinc oxide, polyvinylidene difluoride (PVDF), lithium niobate (LiNbO3)) and opposite the first metal conductive layer. (e.g., such as described regarding aluminum top electrode 2724, regarding one or more exemplary top electrodes 4402, etc., in reference to FIGS. 27 and 44).

In addition, exemplary MEMS device (e.g., exemplary PMUT 2700 for fingerprint sensing on IC comprising exemplary PMUT 2700 bonded to an exemplary CMOS wafer 2802) can further comprise a stand-off (e.g., one or more silicon dioxide standoffs 2716, etc.) formed on the piezoelectric material (e.g., one or more of aluminum nitride, lead zirconate titanate (PZT), zinc oxide, polyvinylidene difluoride (PVDF), lithium niobate (LiNbO3)), according to further non-limiting aspects. For example, an exemplary stand-off (e.g., one or more silicon dioxide standoffs 2716, etc.) can comprise a silicon dioxide layer deposited over the piezoelectric material. In other non-limiting aspects, exemplary MEMS device (e.g., exemplary PMUT 2700 for fingerprint sensing on IC comprising exemplary PMUT 2700 bonded to an exemplary CMOS wafer 2802) can further comprise the MUT structure (e.g., exemplary PMUT 2700 or portions thereof, etc.) bonded to the CMOS structure (e.g., exemplary CMOS wafer 2802 or portions thereof, etc.) at the standoff (e.g., one or more silicon dioxide standoffs 2716, etc.) via at least one of a eutectic bonding layer (e.g., comprising an aluminum-germanium eutectic bonding layer, etc.), a compression bond, or a conductive epoxy and/or the MUT structure electrically coupled to the CMOS structure at the standoff, for example, as further described herein.

In further non-limiting aspect, exemplary MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.) can further comprise a piezoelectric layer comprising an aluminum nitride (AlN) seed layer, a bottom metal layer, and an aluminum nitride (AlN) layer, for example, as further described herein. In still another non-limiting aspect, exemplary MEMS device (e.g., exemplary PMUT 2700 for fingerprint sensing on IC comprising exemplary PMUT 2700 bonded to an exemplary CMOS wafer 2802, exemplary PMUT 3000 integrated on exemplary CMOS wafer 3102, etc.) can further comprise a PMUT array, as described herein, comprising the MUT structure (e.g., exemplary PMUT 2700 or portions thereof, exemplary PMUT 3000 or portions thereof, etc.) in an array of MUT structures (e.g., exemplary PMUT arrays (2902, 2904, 2906), etc.), wherein the MUT structure in the array of MUT structures are configured in a rhombus configuration (2908), in a hexagonal configuration (2912), and/or any combination thereof (e.g., exemplary PMUT arrays 2906).

As a non-limiting example, an exemplary MUT structure (e.g., exemplary PMUT 2700 or portions thereof, exemplary PMUT 3000 or portions thereof, etc.) and the array of MUT structures (e.g., exemplary PMUT arrays 2906, etc.) can comprise a first two of the array of MUT structures in the rhombus configuration 2910 and a second two of the array of MUT structures in the hexagonal configuration 2914 arranged as a unit cell (e.g., exemplary PMUT arrays 2906, etc.).

In addition, in further non-limiting embodiments of the subject disclosure can comprise an exemplary MEMS device (e.g., exemplary PMUT 3000 integrated on exemplary CMOS wafer 3102, etc.), comprising a CMOS device wafer (e.g., exemplary CMOS wafer 3102) associated with a PMUT array of a fingerprint sensor and having a plurality of cavities (e.g., cavities 3202) configured in an array.

In a non-limiting aspect, exemplary MEMS device (e.g., exemplary PMUT 3000 integrated on exemplary CMOS wafer 3102, etc.) can further comprise a first metal conductive layer (e.g., such as described regarding one or more exemplary top electrodes 4402, etc., in reference to FIG. 44) disposed on the CMOS device wafer (e.g., exemplary CMOS wafer 3102) and over the plurality of cavities (e.g., cavities 3202).

In another non-limiting aspect, exemplary MEMS device (e.g., exemplary PMUT 3000 integrated on exemplary CMOS wafer 3102, etc.) can further comprise a piezoelectric material (e.g., one or more of aluminum nitride, lead zirconate titanate (PZT), zinc oxide, polyvinylidene difluoride (PVDF), lithium niobate (LiNbO3)) disposed on the first metal conductive layer (e.g., such as described regarding one or more exemplary top electrodes 4402, etc., in reference to FIG. 44). In still another non-limiting aspect, exemplary MEMS device (e.g., exemplary PMUT 3000 integrated on exemplary CMOS wafer 3102, etc.) can further comprise one or more bottom electrodes (e.g., one or more exemplary bottom contacts 4002, etc.) electrically coupled to one or more top electrodes (e.g., one or more exemplary top electrodes 4402, etc.) via the piezoelectric material. In addition, further non-limiting embodiments of exemplary MEMS device (e.g., exemplary PMUT 3000 integrated on exemplary CMOS wafer 3102, etc.) can further comprise an acoustic propagation layer over the one or more top electrodes (e.g., one or more exemplary top electrodes 4402, etc.), for example, as further described above, for example, regarding FIG. 18. As a non-limiting example, an exemplary acoustic propagation layer comprising a liquid, a polymer, or an acoustic impedance matching material configured to provide acoustic impedance matching between a PMUT device associated with the one or more top electrodes and the cover layer, can be deposited over the one or more top electrodes (e.g., one or more exemplary top electrodes 4402, etc.).

In a further non-limiting aspect, exemplary MEMS device (e.g., exemplary PMUT 3000 integrated on exemplary CMOS wafer 3102, etc.) can further comprise a second metal conductive layer (e.g., molybdenum (Mo) layer 3806, etc.), disposed on the piezoelectric material (e.g., one or more of aluminum nitride, lead zirconate titanate (PZT), zinc oxide, polyvinylidene difluoride (PVDF), lithium niobate (LiNbO3)), electrically coupling the second metal conductive layer and one or more CMOS device wafer electrode (e.g., associated with exemplary top metal layer 3112), and electrically coupling the first metal conductive layer (e.g., such as described regarding one or more exemplary top electrodes 4402, etc., in reference to FIG. 44) to one or more other CMOS device wafer electrode (e.g., associated with exemplary top metal layer 3112), wherein the plurality of cavities (e.g., cavities 3202), the piezoelectric material, the first metal conductive layer, and the second metal conductive layer are configured as a plurality of PMUT structures (e.g., a plurality of exemplary PMUTs 3000, or portions thereof, integrated on exemplary CMOS wafer 3102, etc.).

As a non-limiting example, the plurality of PMUT structures (e.g., a plurality of exemplary PMUTs 3000, or portions thereof, integrated on exemplary CMOS wafer 3102, etc.) can be formed integrally to a CMOS structure (e.g., exemplary CMOS wafer 3102, or portions thereof, etc.), and wherein the fingerprint sensor is adapted to sense a characteristic of a fingerprint placed adjacent to the PMUT array and opposite the plurality of cavities (e.g., cavities 3202). In a further non-limiting example, the plurality of PMUT structures (e.g., a plurality of exemplary PMUTs 3000, or portions thereof, integrated on exemplary CMOS wafer 3102, etc.) can comprise the plurality of PMUT structures in a rhombus configuration (2908), in a hexagonal configuration (2912), and/or in any combination thereof (e.g., exemplary PMUT arrays 2906). As a non-limiting example, an exemplary PMUT structure (e.g., exemplary PMUT 3000 or portions thereof, etc.) and the plurality of PMUT structures (e.g., exemplary PMUT arrays 2906, etc.) can comprise a first two of the plurality of PMUT structures in the rhombus configuration 2910 and a second two of the plurality of MUT structures in the hexagonal configuration 2914 arranged as a unit cell (e.g., exemplary PMUT arrays 2906, etc.).

Figure 46:
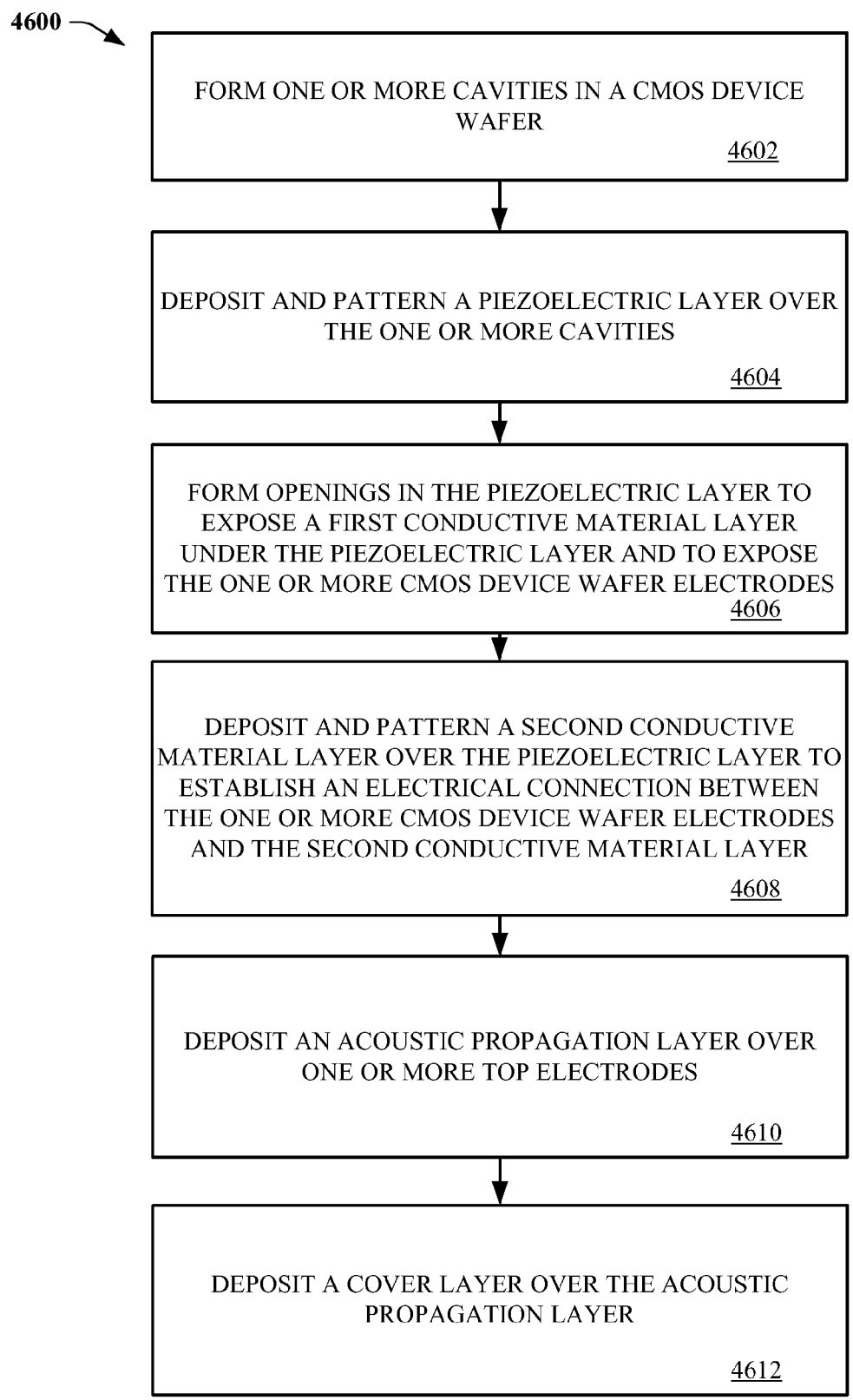
FIG. 46 depicts an exemplary flowchart of non-limiting methods associated with a various non-limiting embodiments of the subject disclosure.
Figure 47:
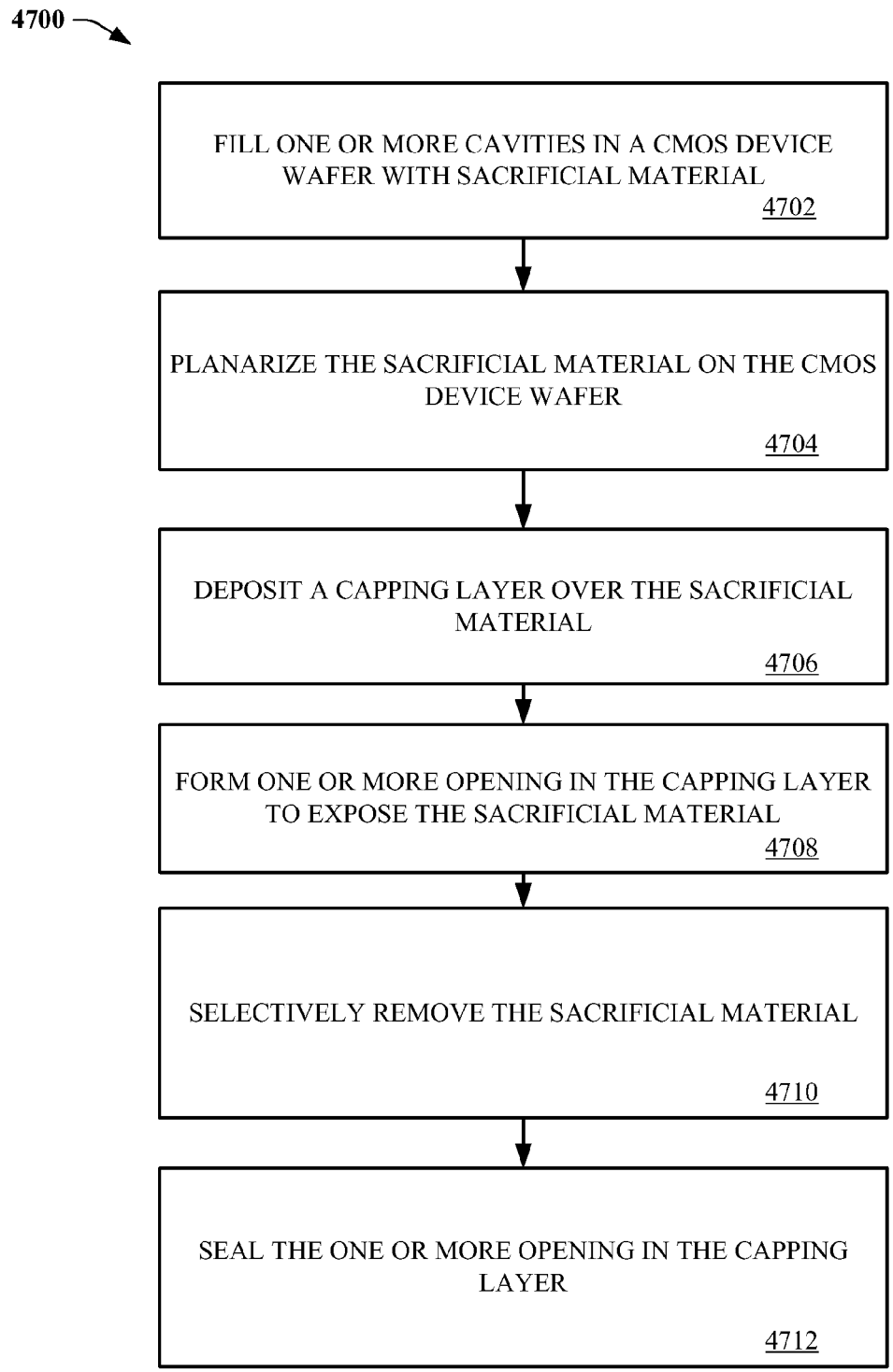
FIG. 47 depicts another exemplary flowchart of non-limiting methods associated with a various non-limiting embodiments of the subject disclosure.

In view of the subject matter described supra, methods that can be implemented in accordance with the subject disclosure will be better appreciated with reference to the flowcharts of FIGS. 46-47. While for purposes of simplicity of explanation, the methods are shown and described as a series of blocks, it is to be understood and appreciated that such illustrations or corresponding descriptions are not limited by the order of the blocks, as some blocks may occur in different orders and/or concurrently with other blocks from what is depicted and described herein. Any non-sequential, or branched, flow illustrated via a flowchart should be understood to indicate that various other branches, flow paths, and orders of the blocks, can be implemented which achieve the same or a similar result. Moreover, not all illustrated blocks may be required to implement the methods described hereinafter.

FIG. 46 depicts an exemplary flowchart of non-limiting methods 4600 associated with a various non-limiting embodiments of the subject disclosure. For instance, exemplary methods 4600 can comprise, at 4602, forming a plurality of cavities (e.g., cavities 3202) in a CMOS device wafer (e.g., exemplary CMOS wafer 3102). As a non-limiting example, forming the plurality of cavities at 4602 can comprise forming a PMUT (e.g., exemplary PMUT 3000 integrated on exemplary CMOS wafer 3102, etc.) array of a fingerprint sensor adapted to sense a characteristic of a fingerprint placed adjacent to the PMUT array and opposite the plurality of cavities (e.g. cavities 3202). In a further non-limiting example, forming the PMUT array comprises forming a plurality of PMUT devices in a rhombus configuration (2908), in a hexagonal configuration (2912), and/or in any combination thereof (e.g., exemplary PMUT arrays 2906), for example, as further described above regarding FIG. 29. In yet another non-limiting example, exemplary methods 4600 can further comprise forming a first two of the plurality of PMUT devices (e.g., exemplary PMUT 3000 integrated on exemplary CMOS wafer 3102, etc.) in the rhombus configuration 2910 and a second two of the plurality of PMUT devices (e.g., exemplary PMUT 3000 integrated on exemplary CMOS wafer 3102, etc.) in the hexagonal configuration 2914 arranged as a unit cell (e.g., exemplary PMUT arrays 2906, etc.).

Exemplary methods 4600 can further comprise, at 4604, depositing and patterning a piezoelectric layer (e.g., comprising aluminum nitride, lead zirconate titanate (PZT), zinc oxide, polyvinylidene difluoride (PVDF), lithium niobate (LiNbO3), etc.) over the plurality of cavities (e.g., cavities 3202). In addition, exemplary methods 4600 can comprise, at 4606, forming a plurality of openings in the piezoelectric layer (e.g., comprising aluminum nitride, lead zirconate titanate (PZT), zinc oxide, polyvinylidene difluoride (PVDF), lithium niobate (LiNbO3), etc.) over the plurality of cavities (e.g., cavities 3202) to expose a first conductive material layer (e.g., molybdenum (Mo) layer 3806, etc.) under the piezoelectric layer and to expose at least one CMOS device wafer (e.g., exemplary CMOS wafer 3102) electrode (e.g., associated with exemplary top metal layer 3112).

In addition, exemplary methods 4600, at 4608, can further comprise depositing and patterning a second conductive material layer (e.g., such as described regarding one or more exemplary top electrodes 4402, etc., in reference to FIG. 44) over the piezoelectric layer (e.g., comprising aluminum nitride, lead zirconate titanate (PZT), zinc oxide, polyvinylidene difluoride (PVDF), lithium niobate (LiNbO3), etc.) to establish an electrical connection between the one or more CMOS device wafer (e.g., exemplary CMOS wafer 3102) electrode (e.g., associated with exemplary top metal layer 3112) and the second conductive material layer. As a non-limiting example, exemplary methods 4600 can further comprise, at 4608, forming one or more bottom electrodes (e.g., one or more exemplary bottom contacts 4002, etc.) electrically coupled to one or more top electrodes (e.g., one or more exemplary top electrodes 4402, etc.) via the piezoelectric layer.

Exemplary methods 4600, at 4610, can further comprise depositing an acoustic propagation layer over the one or more top electrodes (e.g., one or more exemplary top electrodes 4402, etc.), for example, as further described above, for example, regarding FIG. 18. As a non-limiting example, an exemplary acoustic propagation layer comprising a liquid, a polymer, or an acoustic impedance matching material configured to provide acoustic impedance matching between a PMUT device (e.g., exemplary PMUT 3000 integrated on exemplary CMOS wafer 3102, etc.) associated with the one or more top electrodes and the cover layer, can be deposited over the one or more top electrodes (e.g., one or more exemplary top electrodes 4402, etc.), for example, as described above regarding FIG. 18. In addition, exemplary methods 4600, at 4612, can further comprise depositing a cover layer over the acoustic propagation layer, to facilitate providing further protection to the PMUT device (e.g., exemplary PMUT 3000 integrated on exemplary CMOS wafer 3102, etc.) from debris, contaminants, etc. from introducing errors in measurements associated with PMUT device (e.g., exemplary PMUT 3000 integrated on exemplary CMOS wafer 3102, etc.).

FIG. 47 depicts another exemplary flowchart of non-limiting methods associated with a various non-limiting embodiments of the subject disclosure. For instance, exemplary methods 4700, can comprise forming a plurality of cavities (e.g., cavities 3202) in a CMOS device wafer (e.g., exemplary CMOS wafer 3102). As a non-limiting example, exemplary methods 4700, at 4702, can comprise filling the plurality of cavities (e.g., cavities 3202) in the CMOS device wafer (e.g., exemplary CMOS wafer 3102) with sacrificial material (e.g., one or more exemplary sacrificial materials 3302, amorphous silicon, etc.). In a further non-limiting example, exemplary methods 4700, at 4704, can comprise planarizing the sacrificial material (e.g., one or more exemplary sacrificial materials 3302, amorphous silicon, etc.) on the CMOS device wafer (e.g., exemplary CMOS wafer 3102), and at 4706, can further comprise depositing a capping layer (e.g., one or more exemplary silicon dioxide ($SiO_2$) layers 3402, etc.) over the sacrificial material (e.g., one or more exemplary sacrificial materials 3302, amorphous silicon, etc.).

Exemplary methods 4700, at 4708, can further comprise forming one or more openings (e.g., one or more exemplary seal holes 3502) in the capping layer (e.g., one or more exemplary silicon dioxide ($SiO_2$) layers 3402, etc.) to expose the sacrificial material (e.g., one or more exemplary sacrificial materials 3302, amorphous silicon, etc.), and at 4710, can further comprise selectively removing the sacrificial material. In addition, exemplary methods 4700, at 4712, can further comprise sealing the one or more openings in the capping layer (e.g., one or more exemplary silicon dioxide ($SiO_2$) layers 3402, etc.), in addition to depositing the first conductive material layer (e.g., molybdenum (Mo) layer 3806, etc.) comprising a metal conductive layer over the capping layer (e.g., one or more exemplary silicon dioxide ($SiO_2$) layers 3402, etc.).

As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form. In addition, the word "coupled" is used herein to mean direct or indirect electrical or mechanical coupling. In addition, the words "example" and/or "exemplary" are used herein to mean serving as an example, instance, or illustration. Any aspect or design described herein as "example" and/or "exemplary" is not necessarily to be construed as preferred or advantageous over other aspects or designs. Rather, use of the word exemplary is intended to present concepts in a concrete fashion.

What has been described above includes examples of the subject disclosure. It is, of course, not possible to describe every conceivable combination of components or methodologies for purposes of describing the subject matter, but it is to be appreciated that many further combinations and permutations of the subject disclosure are possible. Accordingly, the claimed subject matter is intended to embrace all such alterations, modifications, and variations that fall within the spirit and scope of the appended claims.

In particular and in regard to the various functions performed by the above described components, devices, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter.

The aforementioned systems have been described with respect to interaction between several components. It can be appreciated that such systems and/or components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, may be provided to communicatively couple to such sub-components in order to provide integrated functionality. Any components described herein may also interact with one or more other components not specifically described herein.

In addition, while a particular feature of the subject disclosure may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

Reference throughout this specification to "one embodiment," or "an embodiment," means that a particular feature, structure, or characteristic described in connection with the embodiment is included in at least one embodiment. Thus, the appearances of the phrase "in one embodiment," or "in an embodiment," in various places throughout this specification are not necessarily all referring to the same embodiment. Furthermore, the particular features, structures, or characteristics may be combined in any suitable manner in one or more embodiments.

In this regard, while the disclosed subject matter has been described in connection with various embodiments and corresponding figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A microelectromechanical systems (MEMS) device, comprising:
   a MEMS ultrasonic transducer (MUT) structure and a piezoelectric material disposed over a plurality of cavities within the MEMS device comprising a piezoelectric MUT (PMUT) array of a fingerprint sensor adapted to sense a characteristic of a fingerprint placed adjacent to the MUT structure;
   a first metal conductive layer deposited on a first side of the piezoelectric material; and
   a second conductive layer on a second side of the piezoelectric material configured to form electrical connections between the first metal conductive layer, the piezoelectric material, and an active complementary metal oxide semiconductor (CMOS) structure of a CMOS layer, wherein the MUT structure and the CMOS layer are vertically stacked, wherein the PMUT array comprises the MUT structure in an array of MUT structures, and wherein the MUT structure and the array of MUT structures comprise a first two of the array of MUT structures in a rhombus configuration and a second two of the array of MUT structures in a hexagonal configuration arranged as a unit cell.

2. The MEMS device of claim 1, wherein
the first metal conductive layer and the second conductive layer are connected to a plurality of electrodes with the CMOS layer.

3. The MEMS device of claim 2, wherein
the MEMS device is configured to have a voltage applied to the piezoelectric material via the plurality of electrodes.

4. The MEMS device of claim 2, wherein the first metal conductive layer and the second conductive layer comprise at least one of Molybdenum, Aluminum, Ruthenium, Tungsten, or Platinum.

5. The MEMS device of claim 4, wherein the CMOS layer is configured to at least one of transmit or receive signals to or from the MEMS device.

6. The MEMS device of claim 2, further comprising:
   at least one bond pad that connects at least one of the first metal conductive layer and the second conductive layer to the CMOS layer.

7. The MEMS device of claim 1, wherein the piezoelectric material comprises at least one of aluminum nitride, lead zirconate titanate (PZT), zinc oxide, polyvinylidene difluoride (PVDF), lithium niobate (LiNbO$_3$).

8. The MEMS device of claim 1, further comprising:
   a piezoelectric layer comprising an aluminum nitride (AlN) seed layer, disposed between a bottom metal layer, and an aluminum nitride (AlN) layer.

9. The MEMS device of claim 1, wherein the PMUT array is formed integrally to a CMOS wafer comprising the CMOS layer and the active CMOS structure.

10. A microelectromechanical systems (MEMS) device:
    a complementary metal oxide semiconductor (CMOS) device wafer associated with a piezoelectric MEMS ultrasound transducer (PMUT) array of a fingerprint sensor, wherein the CMOS device wafer has a plurality of cavities within the CMOS device wafer and configured in an array;
    a first metal conductive layer disposed over the CMOS device wafer and over the plurality of cavities;
    a piezoelectric material disposed on the first metal conductive layer; and
    a second metal conductive layer, adjacent to the piezoelectric material, electrically coupling the second metal conductive layer and at least one CMOS device wafer electrode, and electrically coupling the first metal conductive layer to at least one other CMOS device wafer electrode, wherein the plurality of cavities, the piezoelectric material, the first metal conductive layer, and the second metal conductive layer are configured as a plurality of PMUT structures, wherein the plurality of PMUT structures comprise a first two of the plurality of PMUT structures in a rhombus configuration and a second two of the plurality of PMUT structures in a hexagonal configuration arranged as a unit cell.

11. The MEMS device of claim 10, wherein the plurality of PMUT structures are formed integrally to a CMOS structure, and wherein the fingerprint sensor is adapted to sense a characteristic of a fingerprint placed adjacent to the PMUT array and opposite the plurality of cavities.

12. The MEMS device of claim 10, wherein the piezoelectric material comprises at least one of aluminum nitride, lead zirconate titanate (PZT), zinc oxide, polyvinylidene difluoride (PVDF), lithium niobate (LiNbO$_3$).

13. The MEMS device of claim 10, further comprising:
at least one bottom electrode electrically coupled to at least one top electrode via the piezoelectric material.

14. The MEMS device of claim 13, further comprising:
an acoustic propagation layer disposed over the at least one top electrode.

* * * * *